(12) United States Patent
Esko et al.

(10) Patent No.: US 9,889,182 B2
(45) Date of Patent: Feb. 13, 2018

(54) ASSISTED ENZYME REPLACEMENT THERAPY

(75) Inventors: Jeffrey D. Esko, San Diego, CA (US); Yitzhak Tor, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 58 days.

(21) Appl. No.: 13/496,180

(22) PCT Filed: Sep. 15, 2010

(86) PCT No.: PCT/US2010/048968
§ 371 (c)(1),
(2), (4) Date: Apr. 18, 2012

(87) PCT Pub. No.: WO2011/034951
PCT Pub. Date: Mar. 24, 2011

(65) Prior Publication Data
US 2012/0189601 A1 Jul. 26, 2012

Related U.S. Application Data

(60) Provisional application No. 61/242,743, filed on Sep. 15, 2009.

(51) Int. Cl.
A61K 38/54 (2006.01)
A61K 38/47 (2006.01)
A61K 47/48 (2006.01)

(52) U.S. Cl.
CPC .......... *A61K 38/47* (2013.01); *A61K 47/4823* (2013.01); *A61K 47/48092* (2013.01); *C12Y 302/01031* (2013.01)

(58) Field of Classification Search
None
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 6,525,182 B1 | 2/2003 | Goodman et al. | |
| 6,537,785 B1 | 3/2003 | Canfield | |
| 8,071,535 B2 | 12/2011 | Tor et al. | |
| 2005/0208090 A1* | 9/2005 | Keimel | A61K 38/1709 424/423 |

OTHER PUBLICATIONS

Kakkis, Expert Opin. Investig. Drugs 11(5): 675-685 (2002).*
Schwab et al., J. Biol. Chem. 282(18): 13585-13591 (2007).*
Elson-Schwab et al., J. Biol. Chem. 282(18): 13585-13591 (2007).*
Rothbard et al., J. Am. Chem. Soc. 126(31): 9506-9507 (2004).*
Brinkley, Bioconjugate Chem. 3: 2-13 (1992).*
Luedtke et al., J. Am. Chem. Soc. 122: 12035-12036 (2000).*

(Continued)

*Primary Examiner* — Erin M Bowers
(74) *Attorney, Agent, or Firm* — Fish & Richardson P.C.

(57) ABSTRACT

Reagents and methods useful for the synthesis of conjugates comprising guanidinylated cyclic acetals are provided. Also provided are methods for increasing the cellular uptake of various therapeutic compounds and treatment modalities using these conjugates.

22 Claims, 19 Drawing Sheets

(56) References Cited

OTHER PUBLICATIONS

Authorized Officer Lee Ye Rie. International Search Report and Written Opinion in International Application PCT/US2010/048968, dated Jun. 28, 2011, 11 pages.
Authorized Officer S. Baharlou. International Preliminary Report on Patentability in International Application PCT/US2010/048968, dated Mar. 20, 2012, 7 pages.
Bai et al., "Chinese Hamster Ovary Cell Mutants Defective in Glycosaminoglycan Assembly and Glucuronosyltransferase I," *J. Biol. Chem.*, 1999, 274:13017-13024.
Baker et al., "Synthesis and Anti-HIV Activity of Guanidinoglycosides," 65:9054-9058 *J. Org. Chem.*, 2000, 65:9054-9058.
Bame et al., "Sulphated and undersulphated heparin sulphate proteojlycans in a Chinese hamster ovary cell mutant defective in N-sulphotransferase," *Biochemical J.*, 1994, 303:81-87.
Blount et al., "A Tale of Two Targets: Differential RNA Selectivity of Nucleobase-Aminoglycoside Conjugates," Chembiochem, 2006, 7:1612-1621.
Caesar et al., "Membrane Interactions of Cell-Penetrating Peptides Probed by Tryptophan Fluorescence and Dichroism Techniques: Correlations of Structure to Cellular Uptake," *Biochemistry*, 2006, 45:7682-7692.
Chung et al., "Dendritic Oligoguanidines as Intracellular Translocators," *Biopolymers*, 2004, 76:83-96.
Desnick, "Enzyme Replacement and Enhancement Therapies for Lysosomal Disease," *J. Inherit. Metab. Dis.*, 2004, 27:385-410.
Deutscher et al., "Translocation across golgi vesicle membranes: A CHO glycosylation mutant deficient in CMP-sialic acid transport," *Cell*, 1984, 39:295-299.
Dietz et al., "Delivery of bioactive molecules into the cell: the Trojan horse approach," *Mol. Cell. Neurosci.*, 2004, 27:85-131.
Dix et al., "Cooperative, Heparan Sulfate-Dependent Cellular Uptake of Dimeric Guanidinoglycosides," *ChemBioChem*, 2010, 11(16):2302-2310.
Elson-Schwab et al., "Guanidinylated Neomycin Delivers Large, Bioactive Cargo into Cells through a Heparan sulfate-dependent Pathway," *J. Biol. Chem.*, 2007, 282(18):13585-13591.
Esko et al., "Order Out of Chaos: Assembly of Ligand Binding Sites in Heparan Sulfate," *Annu. Rev. Biochem.*, 2002, 71:435-471.
Esko et al., "Animal cell mutants defective in glycosaminoglycan biosynthesis," *Proc. Natl. Acad. Sci. U.S.A.*, 1985, 82:3197-3201
Fermindez-Carneado et al., "Highly Efficient, Nonpeptidic Oligoguanidinium Vectors that Selectively Internalize into Mitochondria," *J. Am. Chem. Soc.*, 2005, 127:869-874.
Fillon et al., "Cell Penetrating Agents Based on a Polyproline Helix Scaffold," *J. Am. Chem. Soc.*, 2005, 127:11798-11803.
Flavell, "Saporin Innumotoxins," *Curr. Top Microbiol. Immunol.*, 1998, 234:57-61.
Frankel et al., "Cellular uptake of the tat protein from human immunodeficiency virus," *Cell*, 1988, 55:1189-1193.
Fuchs et al., "Pathway for Polyarginine Entry into Mammalian Cells," *Biochemistry*, 2004, 43:2438-2444.
Futaki et al., "Translocation of Branched-Chain Arginine Peptides through Cell Membranes: Flexibility in the Spatial Disposition of Positive Charges in Membrane-Permeable Peptides," *Biochemistry*, 2002, 41:7925-7930.
Futaki, "Membrane-permeable arginine-rich peptides and the translocation mechanisms," *Adv. Drug. Deliv. Rev.*, 2005, 57:547-558.
Futaki, "Oligoarginine Vectors for Intracellular Delivery: Design and Cellular-Uptake Mechanisms," *Biopolymers Pept. Sci.*, 2006, 84:241-249.
Green et al., "Autonomous functional domains of chemically synthesized human immunodeficiency virus tat trans-activator protein," *Cell*, 1988, 55:1179-1188.
Hitz et al., "Interaction of α-and γ-Oligoarginine-Acids and Amides with Anionic Lipid Vesicles: A Mechanistic and Thermodynamic Study," *Biochemistry*, 2006, 45:5817-5829.
Kaplan et al., "Cationic TAT peptide transduction domain enters cells by macropinocytosis," *J. Controlled Release*, 2005, 102:247-253.
Kirk et al., "Neomycin-Acridine Conjugate: A Potent Inhibitor of Rev-RRE Binding," *J. Am. Chem. Soc.*, 2000, 122:980-981.
Klein et al., "New chemical tools for investigating human mitotic kinesin Eg5," *Bioorg. Med. Chem.* 2007, 15:6474-6488.
Lamaze et al., "The emergence of clathrin-independent pinocytic pathways," *Curr. Opin. Cell Biol.*, 1995, 7:573-580.
Lidholt et al., "A single mutation affects both N-acetylglucosaminyltransferase and glucuronosyltransferase activities in a Chinese hamster ovary cell mutant defective in heparin sulfate biosynthesis," *Proc. Natl. Acad. Sci. U.S.A.*, 1992, 89:2267-2271.
Luedtke et al., "Guanidinoglycosides: A Novel Family of RNA Ligands," *J. Am. Chem. Soc.*, 2000, 122:12035-12036.
Luedtke et al., "Cellular Uptake of Aminoglycosides, Guanidinoglycosides, and Poly-arginine," *J. Am. Chem. Soc.*, 2003, 125:12374-12375.
Mandl et al., "Synthesis of Mono Protected 1, 10-Diaza-18-Crown-6," *Synthetic Commun.* 2004, 19:3573-2578.
Mayer et al., "Design and Synthesis of a Tag-Free Chemical Probe for Photoaffinity Labeling," *Eur. J. Org. Chem.*, 2007, 28:4711-4720.
Michael et al., "Enhanced RNA binding of dimerized aminoglycosides," *Bioorg. Med. Chem.*, 1999, 7:1361-1371.
Rapraeger et al., "Requirement of heparan sulfate for bFGF-mediated fibroblast growth and myoblast differentiation," *Science*, 1991, 252:1705-1708.
Richard et al., "Cellular Uptake of Unconjugated TAT Peptide Involves Clathrin-dependent Endocytosis and Heparan Sulfate Receptors," *J. Biol. Chem.*, 2005, 280:15300-15306.
Rothbard et al., "Adaptive translocation: the role of hydrogen bonding and membrane potential in the uptake of guanidinium-rich transporters into cells," *Adv. Drug. Deliv. Rev.*, 2005, 57:495-504.
Rothbard et al., "Role of Membrane Potential and Hydrogen Bonding in the Mechanism of Translocation of Guanidinium-Rich Peptides into Cells," *J. Am. Chem. Sci.*, 2004, 126:9506-9507.
Ryser, "Uptake of Protein by Mammalian Cells: An Underdeveloped Area: The penetration of foreign proteins into mammalian cells can be measured and their functions explored," *Science*, 1968, 159:390-396.
Sakai et al., "Direct Observation of Anion-Mediated Translocation of Fluorescent Oligoarginine Carriers into and across Bulk Liquid and Anionic Bilayer Membranes," *Chembiochem*, 2005, 6:114-122.
Sarrazin et al., "Guanidinylated Neomycin Mediates Heparan Sulfate-dependent Transport of Active Enzymes to Lysosomes," *Molecular Therapy*, 2010, 18(7):1268-1274.
Schwabacher et al., "Desymmetrization Reactions: Efficient Preparation of Unsymmetrically Substituted Linker Molecules," *J. Org. Chem.* 1998, 63:1727-1729.
Tyagi et al., "Internalization of HIV-1 Tat Requires Cells Surface Heparan Sulfate Proteoglycans," *J. Biol. Chem.* 2001, 276:3254-3261.
Umezawa et al., "Translocation of a β-Peptide Across Cell Membranes," *J. Am. Chem. Soc.*, 2002, 124:368-369.
Wadia et al., "Transmembrane delivery of protein and peptide drugs by TAT-mediated transduction in the treatment of cancer," *Adv. Drug Del. Rev.*, 2005, 57:579-596.
Wang et al., "Dimeric aminoglycosides: Design, synthesis and RNA binding," *Bioorg. Med. Chem. Lett.*, 1997, 7:1951-1956.
Wang et al., "Tobramycin-edta conjugate: A noninnocent affinity-cleaving reagent," *Bioorg. Med. Chem. Lett.*, 1998, 8:3665-3670.
Wang et al., "Electrostatic Interactions in RNA Aminoglycosides Binding," *J. Am. Chem. Soc.*, 1997, 119:8734-8735.
Wang et al., "Synthesis of (S,R,R,R)-α,α'-Iminobis(methylene)bis(6-fluoro-3H,4H-dihydro-2H-1-benzopyran-2-methanol," *Synthesis*, 2007, 1154-1158.
Wei et al., "Formation of HNK-1 Determinants and the Glycosaminoglycan Tetrasaccharide Linkage Region by UDP-GlcUA:Galactose β1, 3-Glucuronosyltransferases," *J. Biol. Chem.*, 1999, 274:7857-7864.

(56) References Cited

OTHER PUBLICATIONS

Wender et al., "The design, synthesis, and evaluation of molecules that enable or enhance cellular uptake: Peptoid molecular transporters," *Proc. Natl. Acad. Sci.*, 2000, 97:13003-13008.

Williams et al., "Cell-surface heparan sulfate proteoglycans: dynamic molecules mediating ligand catabolism," *Curr. Opin. Lipidol.*, 1997, 8:253-262.

Winchester et al., "The Molecular Basis of Lysosomal Storage Diseases and Their Treatment," *Biochem Society Transactions*, 2000, 28(2):150-153.

Yayon et al., "Cell surface, heparin-like molecules are required for binding of basic fibroblast growth factor to its high affinity receptor," *Cell*, 1991, 64:841-848.

Anderson and Orci, "A View of Acidic Intracellular Compartments," J Cell Biol., Mar. 1988, 106:539-543.

Boesze-Battaglia and Schimmel, "Cell membrane lipid composition and distribution: Implications for cell function and lessons learned from photoreceptors and platelets," J Experimental Biol., 1997, 200:2927-2936.

Chambers, "Aminoglycosides," Goodman & Gilman's The Pharmacological Basis of Therapeutics (Brunton, L. L., Lazo, J. S., and Parker, K. L., eds) 11th Ed., 2006, pp. 1155-1171, McGraw-Hill, New York, 19 pages.

Luzio et al., "Membrane dynamics and the biogenesis of lysosomes (Review)," Mol Membrane Biol., Apr.-Jun. 2003, 20:141-154.

\* cited by examiner

ASSISTED ENZYME REPLACEMENT THERAPY

CROSS-REFERENCE TO RELATED APPLICATIONS

This application is a National Stage application under 35 U.S.C. § 371 of International Application No. PCT/US2010/048968, having an International Filing Date of Sep. 15, 2010, which claims priority to U.S. Provisional Application Ser. No. 61/242,743, filed Sep. 15, 2009, which is incorporated by reference in its entirety herein.

STATEMENT AS TO FEDERALLY SPONSORED RESEARCH

This invention was made with government support under AI047673 and GM077471 awarded by National Institutes of Health. The government has certain rights in the invention.

TECHNICAL FIELD

The disclosure relates generally to bioavailability and delivery of therapeutic molecules and, more specifically, to guandinylated cyclic acetals and conjugation of such modified acetals to therapeutic compounds to increase the cellular uptake of the therapeutic compounds. This application hereby incorporates by reference U.S. application Ser. No. 10/571,510, filed Sep. 10, 2004; and U.S. Provisional Application Ser. No. 60/502,385, filed Sep. 12, 2003 in their entireties for all purposes.

BACKGROUND

Charged molecules over 500 Dalton typically exhibit poor bioavailability. This limits the delivery of many therapeutically active molecules to their intended targets. Polycationic molecules provide important exceptions to this generalization. Modification of Bovine Serum Albumin (BSA) with ethylene diamine produces "cationionized BSA", a highly effective antigen carrier. Despite its size (over 66,000 Dalton), cationized BSA efficiently enters cells via an unknown path involving adsorptive uptake. More recently, a number of poly-arginine peptides, peptoids, and peptidomimetics, have been found to exhibit highly efficient uptake into a wide range of mammalian cell types. The conjugation of such poly-Arg peptides to large molecules can facilitate the transduction of peptide, protein, and nucleic acid, conjugates into cells. The mechanism responsible for poly-Arg mediated transport is still unclear, but may involve a receptor mediated, non-endocytotic route. Thus, an opportunity exists for exploiting such a poly-arginine peptide-like transduction mechanism for efficient uptake of therapeutically active molecules by eukaryotic cells.

Current technologies exist for producing high uptake forms of lysosomal enzymes that contain mannose-6-phophate or mannose residues, which are recognized by mannose-6-phosphate or mannose receptors. This method allows delivery of enzymes to lysosomes and is currently being used clinically for treating lysosomal storage diseases with some success. Efficient transport across the blood-brain barrier however, has not been achieved and some enzymes are not efficiently modified and delivered in this way. Another approach, which is under development, is the use of guanidinylated peptidic carriers and non-carbohydrate scaffolds.

SUMMARY

The present disclosure is based on the discovery that guanidineglycoside containing conjugates can exhibit enhanced cellular uptake at target cells, and thus may be useful in the delivery of therapeutic compounds for treatment of variety of diseases and disorders.

In one embodiment, a method of increasing the cellular uptake of a compound is provided which includes conjugation of a compound with a molecule having a modified cyclic acetal. The acetal can be guanidinylated. In one aspect, such an acetal may be polymeric or non-polymeric. In a related aspect, a method of making such conjugates is also envisaged.

In another related aspect, the modified cyclic acetal is a natural or synthetic glycoside and, more particularly includes, but is not limited to, aminoglycosides, cardiac glycosides, disaccharides or other oligosaccharides. Further, primary or secondary alcohol or primary or secondary amines of these glycosides can be reacted with guanidinylating reagents to produce guanidinoglycosides. In one embodiment, such guanidinoglycosides can be covalently bonded to molecules of interest, including therapeutically active molecules.

In a related aspect, guanidinylated cyclic acetal containing compounds include, but are not limited to, amikacin, gentamicin, kanamycin, neomycin, netilmicin, O-2,6-Diamino-2,6-dideoxy-beta-L-idopyranosyl-(1 to 3)-O-beta-D-ribofuranosyl-(1 to 5)-O—[2-amino-2-deoxy-alpha-D-glucopyranosyl-(1 to 4)]-2-deoxystreptamine, streptomycin, tobramycin, pentamycin, paromomycin, ouabain, deslanoside, digoxin, digitoxin, lantoside, gitoxigenin, bufalin and strophanthin.

Further, compounds covalently conjugated to the guanidinoglycosides of the present disclosure may include, but are not limited to, nucleic acids, nucleosides, proteins, peptides, amino acid residues, lipids, carbohydrates, synthetic organic compounds, metals, vitamins, small molecules, dyes, isotopes, antibodies, toxins ligands or any other compound that may need transport into a cell.

In one embodiment, the conjugates include, but are not limited to, a nucleoside, such as a reverse transcriptase inhibitor (RTI). In a related aspect, such nucleosides may include, but are not limited to, 3'-azido-3'-deoxythymidine, 2',3'-dideoxyinosine and 2',3'-dideoxycytidine. In another related aspect, the reverse transcriptase inhibitor is conjugated to a guanidine-modified aminoglycoside, such as guanidino-amikacin, guanidino-gentamicin, guanidino-kanamycin, guanidino-neomycin, guanidino-netilmicin, guanidino-O-2,6-Diamino-2,6-dideoxy-beta-L-idopyranosyl-(1 to 3)-O-beta-D-ribofuranosyl-(1 to 5)-O—[2-amino-2-deoxy-alpha-D-glucopyranosyl-(1 to 4)]-2-deoxystreptamine, guanidino-streptomycin and guanidino-tobramycin.

DETAILED DESCRIPTION

Figure 1:
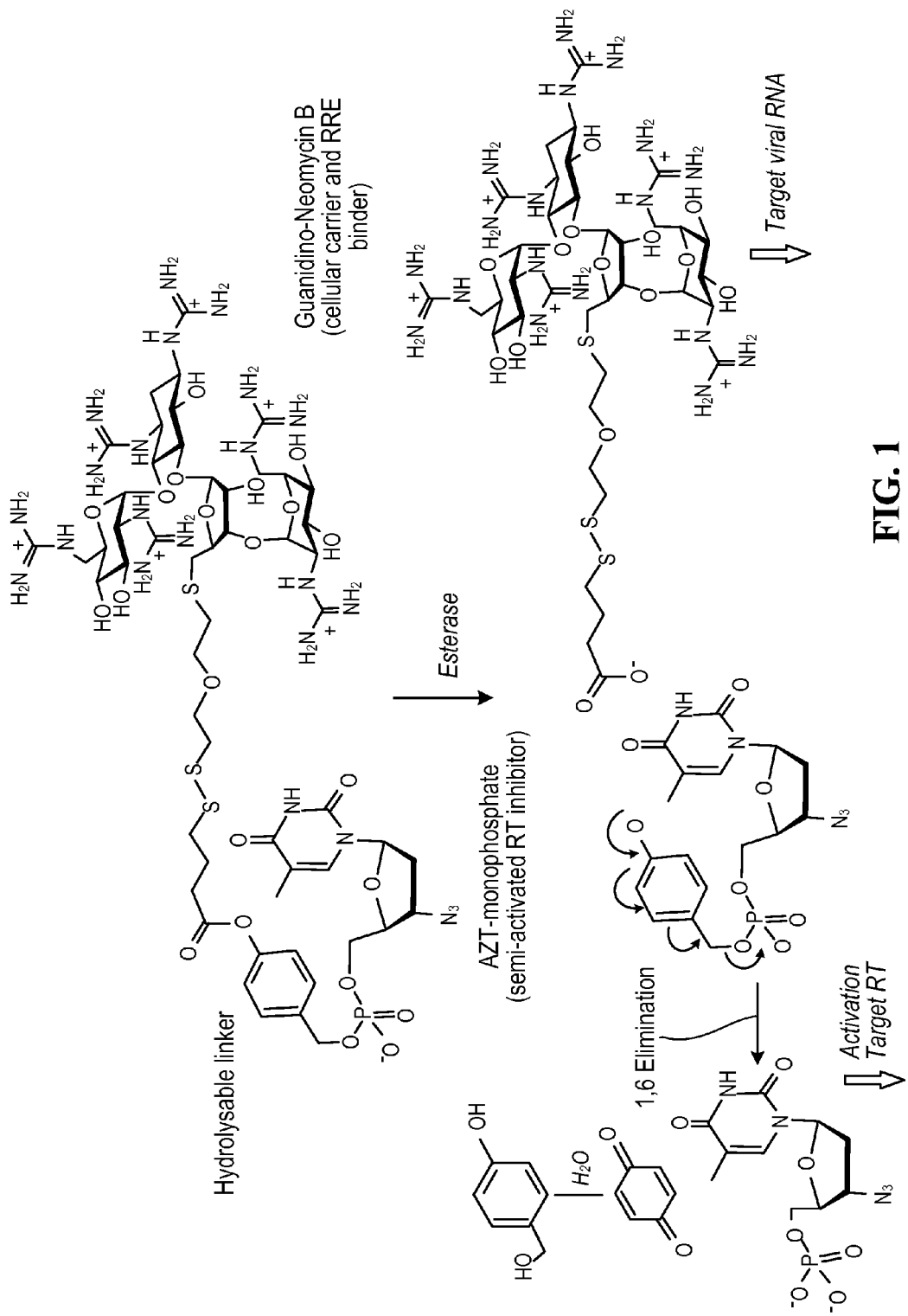
FIG. 1 illustrates a representative structure of a three component conjugate.

The present disclosure provides guanidinoglycoside-containing conjugates which exhibit enhanced cellular uptake at target cells. Such conjugates are useful in the delivery of therapeutic compounds for a number of diseases and disorders including, but not limited to, viral infections (e.g., retroviral infections associated with HIV, HBV, and the like), bacterial infections, and disorders associated with, for example, inappropriate mitogenic signaling, non-insulin-dependent diabetes, and inhibition of enzymes including thrombin, glycosidases, and nitric oxide synthases.

In particular, the present disclosure provides compositions and methods for assisted enzyme replacement therapy. Genetic diseases that result in the absence of essential enzymes (or the presence or defective enzymes) can, in certain cases, be treated by intravenous infusion of the missing protein. Large quantities of enzymes are typically administered with varying level of success. The present disclosure provides new delivery vehicles that upon conjugation to the missing enzymes, facilitate their transport and restore in vivo activity at high efficiency.

The delivery vehicle or carrier comprises covalently conjugating guanidinylated neomycin (or other guanidinylated glycosides) to an enzyme or protein, wherein the carrier transports the enzyme or protein into the interior of the cell by way of proteoglycan receptors on the cell surface. This system has a very high capacity since proteoglycans are much more abundant on cells than other kinds of receptors.

Evidence indicates that the new guanidinylated glycosides act as transporters by binding to cell surface proteoglycan receptors. These receptors are numerous and undergo continuous endocytosis. Thus, enzymes conjugated to a guanidinylated glycoside ("cargo") bind to proteoglycans and "piggy-back" into the cell. During this process some of the cargo appears in the cytoplasm (established), some goes to the lysosome (established), and some may go to other parts of the cell. The precise mechanism for routing the cargo has not been established, but the net result is the appearance of cargo in desirable subcompartments of the cell. Furthermore, the method is highly selective for proteoglycan receptors on the cell, which provides a single portal of entry. High activity at low concentrations suggests minimal adverse effects. We have generated proof of principle, demonstrating the ability of our transporters to deliver, in active form, two enzymes whose absence causes lysosomal storage diseases. We also have demonstrated delivery of an enzyme to the cytoplasm.

Clinical applications include enzyme replacement therapy for disorders in which a cell is missing an enzyme or protein. Specific examples include lysosomal storage diseases, congenital disorders of glycosylation, and metabolic disorders characterized by missing or reduced enzyme activity in the cytoplasm. Non-limiting examples of lysosomal storage diseases include: Activator Deficiency; Alpha-mannosidosis; Aspartylglucosaminuria; Cholesteryl ester storage disease; Chronic Hexosaminidase A Deficiency; Cystinosis; Danon disease; Fabry disease; Farber disease; Fucosidosis; Galactosialidosis; Gaucher disease; GM1 gangliosidosis;

I-Cell disease; Infantile Free Sialic Acid Storage Disease; Juvenile Hexosaminidase A deficiency; Krabbe disease; Metachromatic Leukodystrophy; Mucopolysaccharidoses disorders (e.g., Pseudo-Hurler polydystrophy; Hurler Syndrome; Scheie syndrome; Hurler-Scheie syndrome; Hunter syndrome; Sanfilippo syndrome type A; Sanfilippo syndrome type B; Sanfilippo syndrome type C; Sanfilippo syndrome type D; Morquio type A; Morquio type B; Maroteaux-Lamy; Sly syndrome; and Natowicz syndrome Hyaluronidase deficiency); Multiple sulfatase deficiency; Niemann-Pick disease; Neuronal Ceroid Lipofuscinoses (e.g, CLN6 disease; Batten-Spielmeyer-Vogt/Juvenile NCL/CLN3 disease; Finnish Variant/Late Infantile CLN5; Jansky-Bielschowsky disease/Late infantile CLN2/TPP 1 Disease; Kufs/Adult-onset NCL/CLN4 disease; Northern Epilepsy/variant Late Infantile CLN8; Santavuori-Haltia/Infantile CLN1/PPT disease; and β-mannosidosis); Pompe disease; Pycnodysostosis; Sandhoff disease; Schindler disease; Salla disease; Tay-Sachs; and Wolman disease.

Pharmaceutical applications include treatment of metabolic disorders in which enzymes or structural proteins are missing. For example, a conjugate can include one or two guanidinoglycosides and an enzyme useful in the treatment of a lysosomal storage disease.

In some cases, these enzymes can include: α-D-mannosidase; N-aspartyl-β-glucosaminidase; acid lipase; hexosaminidase A; α-galactosidase A; β-galactosidase; ceramidase; fucosidase; β-glucosidase; N-acetylglucosamine-1-phosphotransferase; galactocerebrosidase; arylsulfatase A; N-acetylglucosamine-1-phosphotransferase; α-L-iduronidase; iduronate sulfatase; heparan sulfamidase; N-acetylglucosaminidase; acetyl-CoA:α-glucosaminide acetyltransferase; N-acetylglucosamine 6-sulfatase; N-acetylgalactosamine-6-sulfate sulfatase; N-acetylgalactosamine-4-sulfatase; β-glucuronidase; hyaluronidase; sialidase; sulfatase; sphingomyelinase; acid α-glucosidase; β-mannosidase; cathepsin K; 3-hexosaminidase A; β-hexosaminidase B; α-N-acetylgalactosaminidase; sialin; and hexosaminidase A. In some embodiments, the enzyme is β-glucosidase or α-iduronidase. Further examples can be found, for example, in The Metabolic and Molecular Bases of Inherited Disease by Scriver, Beudet, Valle, Sly, Childs, Kinzler, and Vogelstein, Vol 3, part 16, chapters 134-154.

Biochemical (academic) applications include use in laboratory environment.

The term "alkyl" used herein refers to a monovalent straight or branched chain radical of from one to ten carbon atoms, including, but not limited to, methyl, ethyl, n-propyl, isopropyl, n-butyl, isobutyl, tert-butyl, n-hexyl, and the like. Alkyl also represents cyclic radicals, including, but not limited to cyclopropyl, cyclobutyl, cyclopentyl, cyclohexyl, and the like.

The term "cationionized" used herein refers to the process of modifying a compound with a molecule such that the surface of the compound is positively charged.

The term "perfluoroalkyl" as used herein refers to a monovalent straight chain radical of from one to four carbon atoms, in which all hydrogen atoms are substituted by fluorine. A typical perfluorinated alkyl group is the trifluoromethyl group.

The term "aryl" when used alone refers to an aromatic radical whether or not fused. Preferred aryl groups include phenyl, naphthyl, biphenyl and the like. Aryl also refers to heteroaromatic groups including, but not limited to, furanyl, pyrrolyl, thienyl, pyrazolyl, thiazolyl, oxazolyl, pyridyl, pyrimidinyl, indolyl, and the like.

The term "substituted aryl" as used herein refers to an aryl group substituted with one, two or three substituents chosen from halogen, cyano, nitro, C1-C10 alkyl, C1-C10-alkoxy, trifluoromethyl, alkoxycarbonyl, and the like. Examples of such groups are 4-chlorophenyl, 2-methylphenyl, and 3-ethoxyphenyl.

The term "arylalkyl" as used herein refers to one, two or three aryl groups having the designated number of carbons, appended to an alkyl chain having the number of carbons designated. A typical arylalkyl group is the benzyl group.

The term "alkenyl" as used herein refers to a straight or branched chain group of from two to ten carbon atoms containing a carbon-carbon double bond, including, but not limited to allyl, vinyl, and the like.

The term "acetal" as used herein is defined an organic compound that is a product of a reaction between an alcohol and an aldehyde. The general structure of an acetal can be illustrated as shown by the structure (I) below.

(I)

The term "cyclic acetal" as used herein is defined as an acetal in which at least one oxygen atom of an acetal is a part of a ring. In one embodiment, the structure of the cyclic acetal that can be used is encompassed by the structure (I) above, where the R1, R2, and/or R3 groups comprise at least two 5- or 6-membered rings that are linked together by at least one acetal-type functional group where R1-R2, and R3 are the carbon atoms of two separate ring systems.

The term "ketal" as used herein is defined an organic compound that is a product of a reaction between an alcohol and ketone. The general structure of a ketal can be illustrated as shown by the structure (II) below, in which each of R and R1 is, independently, hydrogen or alkyl, and each of R2 and R3 is an alkyl.

(II)

The term "dialkoxy compounds" as used herein is defined as compounds having two alkoxy groups attached to the same carbon. Accordingly, the term "dialkoxy compounds" is used herein as inclusive of both acetals illustrated by the formula (I) and ketals illustrated by formula (II) shown above.

The term "guanidine" as used herein is defined as a substance having the general structure (III):

(III)

wherein each of $R_1$, $R_2$ and $R_3$ is, independently, hydrogen or a lower alkyl group, e.g., a $C_1$-$C_3$ alkyl.

Accordingly, wherever the term "guanidine" is used herein, the term is inclusive of unsubstituted guanidine (each of $R_1$, $R_2$ and $R_3$ in structure (III) is hydrogen) and of an alkylguanidine (at least one of $R_1$, $R_2$ and $R_3$ in structure (III) is a lower alkyl group).

The term "guanidine group" or "guanidine moiety" as used herein is defined as a group or moiety derived from either unsubstituted guanidine or from an alkylguanidine, as defined above.

The term "guanidinylated acetal" as used herein is defined as an acetal having a guanidine moiety attached to it. The embodiments of the present disclosure include guanidinylated cyclic acetal reagents as discussed below. These guanidinylated cyclic acetal reagents can be used in the synthesis of conjugates for the transport/uptake of compounds into eucaryotic cells. Guanidinylating reagents and general methods for producing guanidinoglycosides are defined and described in U.S. Pat. No. 6,525,182, the disclosure of which is herein incorporated by reference in its entirety.

The term "guanidinoglycoside" (GG) as used herein refers to derivatives of aminoglycosides in which one or more of the ammonium groups have been converted into guanidinium groups. In some cases, all of the ammonium groups can be converted into guanidinium groups. For example, guanidinylated neomycin (GNeo) contains six positively charged guanidinium groups in place of the naturally occurring amino groups on the three monosaccharide units and the one cyclitol that make up the antibiotic.

The abbreviation "Boc" refers to tert-butyxocarbonyl group.

The term "BODIPY" is a trade name of one of a family of fluorescent dyes available from Molecular Probes, Inc. (Eugene, Oreg.).

The abbreviation "TIPS" refers to 2,4,6-triisopropylbenzenesulfonyl moiety.

The term "parenteral administration" as used herein includes administration by subcutaneous injections, aerosol, intravenous, intramuscular, intrathecal, intracranial, intrasternal injection or infusion techniques.

The term "coupled" as used herein includes both covalent and noncovalent bonding of two or more moieties. In some cases, the term coupled can include covalent or noncovalent bonding which occurs directly between the moieties or optionally via one or more linkers.

Embodiments of the present disclosure are directed to methods of achieving an increased cellular uptake of therapeutically beneficial compounds. The methods include modifying a dialkoxy compound with a substance having a guanidine group, such as guanidine or alkylguanidine, to form an adduct, followed by conjugating a therapeutically beneficial compound to the adduct to form a conjugate, and by delivering the conjugate to a cell. The dialkoxy compounds, which can be modified by guanidine, include acetals and ketals, for example, cyclic acetals.

The conjugates described herein are also directed to methods of increasing the cellular uptake of enzymes useful for the treatment of lysosomal diseases. For example, such an enzyme can be coupled to one or more guanidinoglycosides to form a conjugate. This conjugate can then be delivered to the cell. In some embodiments, the conjugates can be used to increase the lysosomal uptake of an enzyme. The conjugate can be prepared through the coupling of a guanidinoglycoside to an enzyme useful for the treatment of a lysosomal disorder and the conjugate can be delivered to the lysosome. The methods can be used in the treatment of lysosomal storage disorders by providing missing enzymes to the lysosomes of a patient in need.

Some embodiments of the present disclosure relate to compounds covalently conjugated to guanidinoglycosides that exhibit efficient uptake by eukaryotic cell cultures. The mechanism of the uptake may be similar to that exhibited by cationionized peptides. In a related aspect, such conjugated products may share the same uptake mechanism as the TAT and other arginine-containing peptides.

Other embodiments of the present disclosure relate to the conjugates themselves and methods of using such conjugates in treating patients. Such treatments may include, but are not limited to, modalities where delivery of nucleic acids, nucleosides, proteins, peptides, amino acid residues, lipids, carbohydrates, synthetic organic compounds, metals, vitamins, small molecules, dyes, isotopes, antibodies, toxins ligands or any other compound that may need transport into a cell is required. In one embodiment, conjugates may be administered to patients having bacterial or viral infections, including administering conjugates comprising guanidinoglycosides in amounts sufficient to inhibit or prevent such infections. In a related aspect, conjugates containing reverse transcriptase (RT) inhibitors (RTI) for the treatment of HIV are also envisaged.

In one embodiment, the efficacy of cellular uptake for molecules conjugated to the guanidinoglycosides of the present disclosure can be enhanced for anti-HIV of nucleoside based RTIs. In a related aspect, efficacy for such RTIs can be enhanced by covalently conjugating their monophosphates to guanidinoglycosides. In another embodiment, where RT inhibitors can be actively transported into the cell and then released in a semi-active (and potentially fully activated) form, the necessary monophosphorylation step can be circumvented. In one embodiment, essential regulatory events involving viral specific protein RNA interactions (e.g., Rev RRE) are inhibited. Thus, in a related aspect, two distinct stages in the life cycle of the virus are targeted with one anti-HIV agent. An example of this strategy is illustrated in FIG. 1 discussed below.

In one embodiment, the affinity of guanidinoglycosides to viral RNA sequences and their cellular uptake features have resulted in the formulation of a strategy where hybrid molecules containing a nucleotide analog conjugated to a guanidinoglycoside are proposed as "double warhead" anti-HIV agents.

In one related aspect, the disclosure can be used to enhance the therapeutic factor of clinically proven nucleoside reverse transcriptase inhibitors (NRTIs) by reducing the number of metabolic activation steps needed, including but not limited to, increasing negatively charged nucleotide residence in the cell. In another aspect, NRTIs that have failed to be metabolically activated may be given new clinical applications as novel formulations. Such new and effective anti-HIV agents may be produced at low cost and low market price.

In another embodiment, the conjugates described herein can be used to treat a lysosomal storage disease in a mammal (e.g., a human). For example, a therapeutically effective amount of a conjugate comprising one or more guanidinoglycosides and an enzyme useful for treating a lysosomal storage disease can be administered to the mammal.

Examples of cyclic acetals that can be used include the generic structures (IV) and (V) shown below.

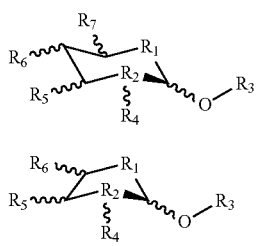

(IV)

(V)

In the structures (IV) and (V), two or more rings are linked by at least one cyclic acetal, where $R_1$ and $R_2$ must be either carbon or oxygen atoms that compose a natural or synthetic glycoside (cyclic acetal), including, but not limited to, aminoglycosides, cardiac glycosides, disaccharides, or other oligosaccharides.

In one embodiment, R3 is a 5 or 6-membered ring (or series of rings linked by acetal linkages) that is either an additional glycosidic unit(s), or alternatively, a substituted hexane or pentane ring (where both the R1 and R2 groups are carbon atoms). One or more of the carbon atoms that compose these 5- or 6-membered rings are directly substituted with one or more basic groups, where R4-R7 is an amine, guanidine, methylene, or alternatively, an acetal linkage to another ring system(s) that contains one or more of these functional groups.

In one embodiment, such substituted aminoglycosides are conjugated to therapeutic compounds. A representative retrosynthetic Scheme showing one synthetic route of conjugation is illustrated below (Scheme I).

Scheme I

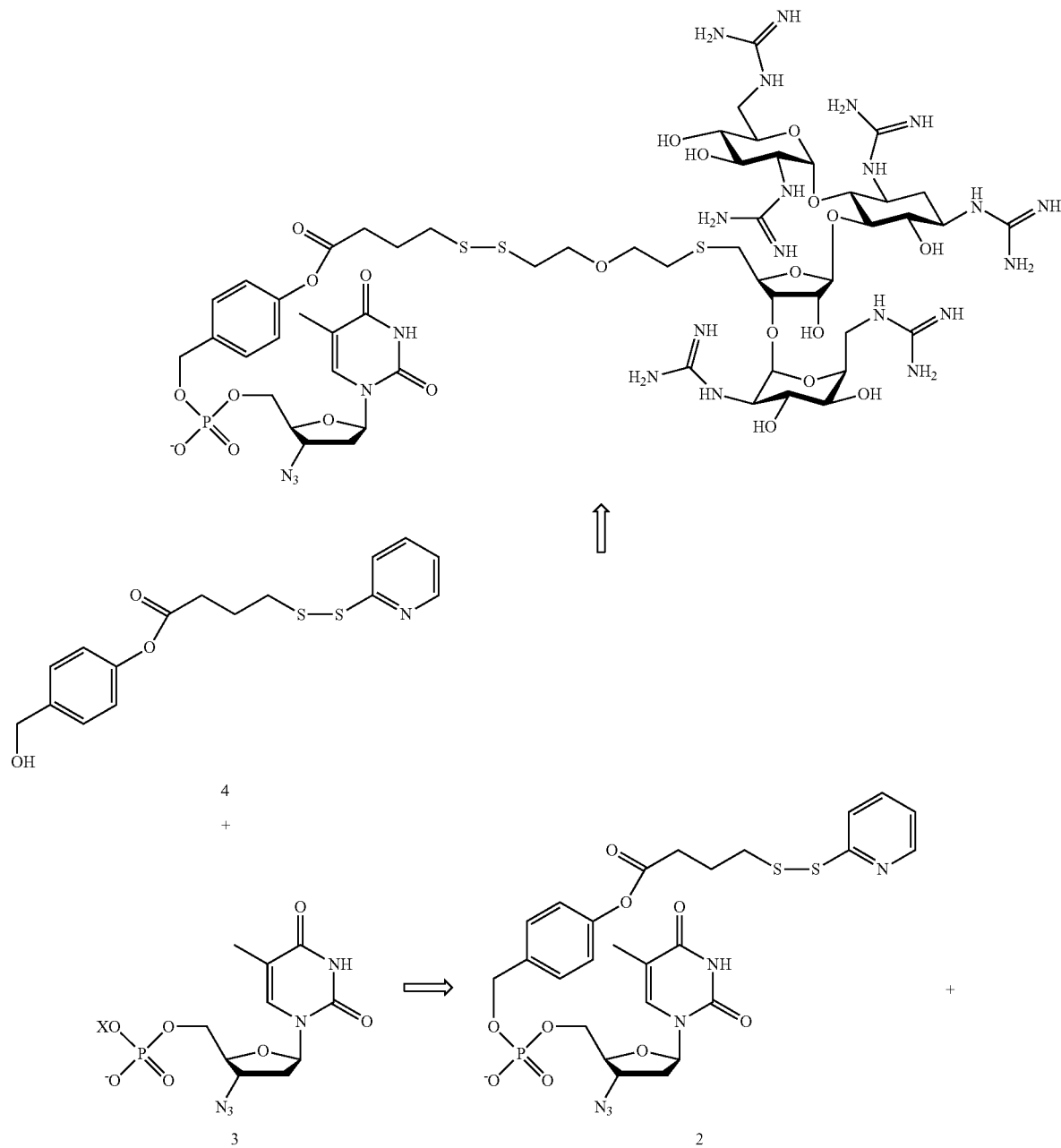

-continued

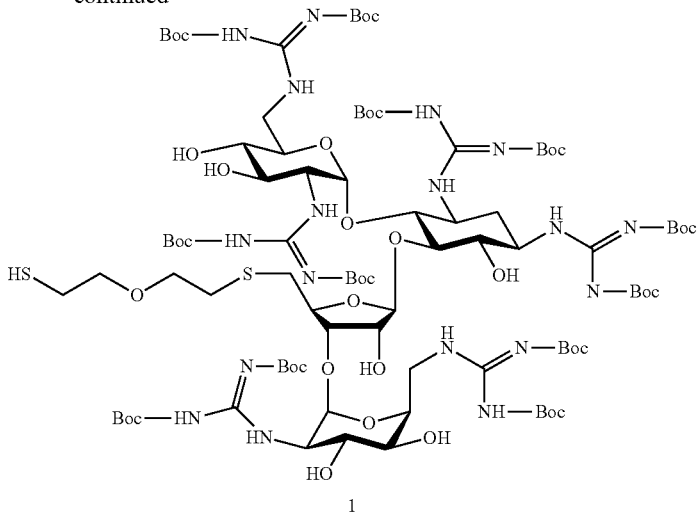

1

As shown by Scheme I, a fully-Boc protected guanidino-neomycin B (1) bearing a long thiol-containing linker can be conjugated via an effective thiol-exchange reaction with the extended AZT-linker conjugate (2). This "extended" AZT can be obtained by condensing the activated AZT-monophosphate (3) with the linker (4), which in turn can be obtained from commercially available building blocks via standard chemistry (e.g., SIGMA Chemical Co., St. Louis, Mo.). Synthesis of the various modified aminoglycosides, guanidinoglycosides and their conjugates is known in the art (see, e.g., U.S. Pat. No. 6,525,182; Wang et al., J. Am. Chem. Soc. (1997) 119:8734-8735; Wang et al., Bioorg. Med. Chem. Lett. (1997) 7:1951-1956; Kirk et al., J. Am. Chem. Soc. (2000) 122:980-981; Wang et al., Bioorg. Med. Chem. Lett. (1998) 8:3665-3670; Luedtke et al., J. Am. Chem. Soc. (2000) 122:12035-12036; and Baker et al., J. Org. Chem. (2000) 65:9054-9058). Several alternative building blocks are discussed below.

In some cases, the guanidinoglycoside comprises an aminoglycoside antibiotic. For example, the guanidinoglycoside can be selected from the group consisting of: guanidino-amikacin, guanidino-gentamicin, guanidino-kanamycin, guanidino-neomycin, guanidino-netilmicin, guanidino-O-2,6-diamino-2,6-dideoxy-beta-L-idopyranosyl-(1 to 3)-O-beta-D-ribofuranosyl-(1 to 5)-O—[2-amino-2-deoxy-alpha-D-glucopyranosyl-(1 to 4)]-2-deoxystreptamine, guanidine-paramycin, guanidino-streptomycin, and guanidino-tobramycin.

A linker can be any physiologically compatible chemical group that does not interfere with the functions of the guanidinoglycoside or the therapeutically active group (e.g., an enzyme). Preferred linkers are synthetically easy to incorporate into the conjugates. They are also not so unduly large as to manifest an undesired biological function or targeting influence onto the conjugate. Preferably, the length of the linker is between 1 and 50 angstroms, more preferably 1 and 10 angstroms. For example, a linker can include an N-hydroxysuccinimide moiety or a polyethylene glycol moiety.

In one embodiment, the conjugate design facilitates a modular synthesis where the various components can be separately synthesized and then coupled together in advanced stages. In a related aspect, this allows mixing-and-matching of various carriers/RRE binders with a variety of linkers and NRTI monophosphates.

The modular design of the proposed conjugates translates into significant flexibility in the synthetic approach. Numerous reagents and reaction conditions are available for each coupling step. The formation of the phosphodiester linkage between AZT monophosphate (3) and the linker (4), for example, can be facilitated by, but is not limited to, carbonyldiimidazole or via DMAP-catalyzed carbodiimide condensation.

In one embodiment, a conjugate can include three key functional components as shown by FIG. 1. The three components shown by FIG. 1 are (1) guanidine-neomycin B (cellular carrier); (2) AZT monophosphate; and (3) a releasable linker.

For example, for nucleoside-based RT inhibitor, as HIV reverse transcriptase (RT) is a low-fidelity DNA polymerase, it can be inhibited by nucleoside analogs that mimic deoxyribonucleoside triphosphates (dNTP), its natural substrates. In a related aspect, well-established inhibitors, such as 3'-azido-2',3'-dideoxythymidine (AZT) in their semi-activated form are envisaged as conjugated compounds.

In a further related aspect, to effectively release the semi-activated NRTI from its carrier/RRE binder, a hydrolysable linker may be employed. For example, an esterase-induced hydrolysis followed by a facile 1,6-elimination reaction that releases the NRTI-monophosphate in its intact form can be used (see e.g., FIG. 1).

In one embodiment, an RRE binder/membrane translocation vehicle is contemplated. The Rev-Response-Element (RRE) serves as the Rev-binding site responsible for the active export of unspliced and singly spliced HIV genomic RNA from the nucleus. Small organic molecules that target such unique viral RNA sites can prevent the formation of a key regulatory RNA-protein complex and interfere with viral replication. In a related aspect, the use of guanidino-neomycin B and guanidino-tobramycin is contemplated. These two derivatives have substantial affinity to the RRE (see, e.g., U.S. Pat. No. 6,525,182) and very effective cellular uptake profiles (see below).

In a related aspect, any NRTI-monophosphate can potentially be employed. Similarly, various linkers with different degradation mechanisms will be readily appreciated by one of skill in the art. Additionally, numerous guanidinoglycosides can be utilized. For example, natural or synthetic guandino-sugars, or guanidinylated aminoglycoside derivatives can also be used. In one embodiment, the guanidinylated forms of dimeric aminoglycosides or the guanidylated products of aminoglycoside decomposition fragments and/or simple oligomers of these units are envisaged. In addition, modification of other (common) forms of saccharides including di-, tri-, and tetra-saccharides may also be suitable scaffolds for the presentation of guanidine groups. In one embodiment, for guanidinoglycosides, such modified forms may include, but are not limited to, guanidino-amikacin, guanidino-gentamicin, guanidino-kanamycin, guanidino-neomycin, guanidino-netilmicin, guanidino-O-2, 6-Diamino-2,6-dideoxy-beta-L-idopyranosyl-(1 to 3)-O-beta-D-ribofuranosyl-(1 to 5)-O-[2-amino-2-deoxy-alpha-D-glucopyranosyl-(1 to 4)]-2-deoxystreptamine, guanidino-streptomycin and guanidino-tobramycin.

In another embodiment, for cardiac glycosides, such modified forms may include but are not limited to, guanidino-ouabain, guanidino-deslanoside, guanidino-digoxin, guanidino-digitoxin, guanidino-lantoside, guanidino-gitoxigenin, guanidino-bufalin and guanidino-strophanthin.

In some cases, a conjugate can comprise two guanidino-glycosides and a therapeutically active compound.

For amines, a typical reaction Scheme can be as follows (Scheme II):

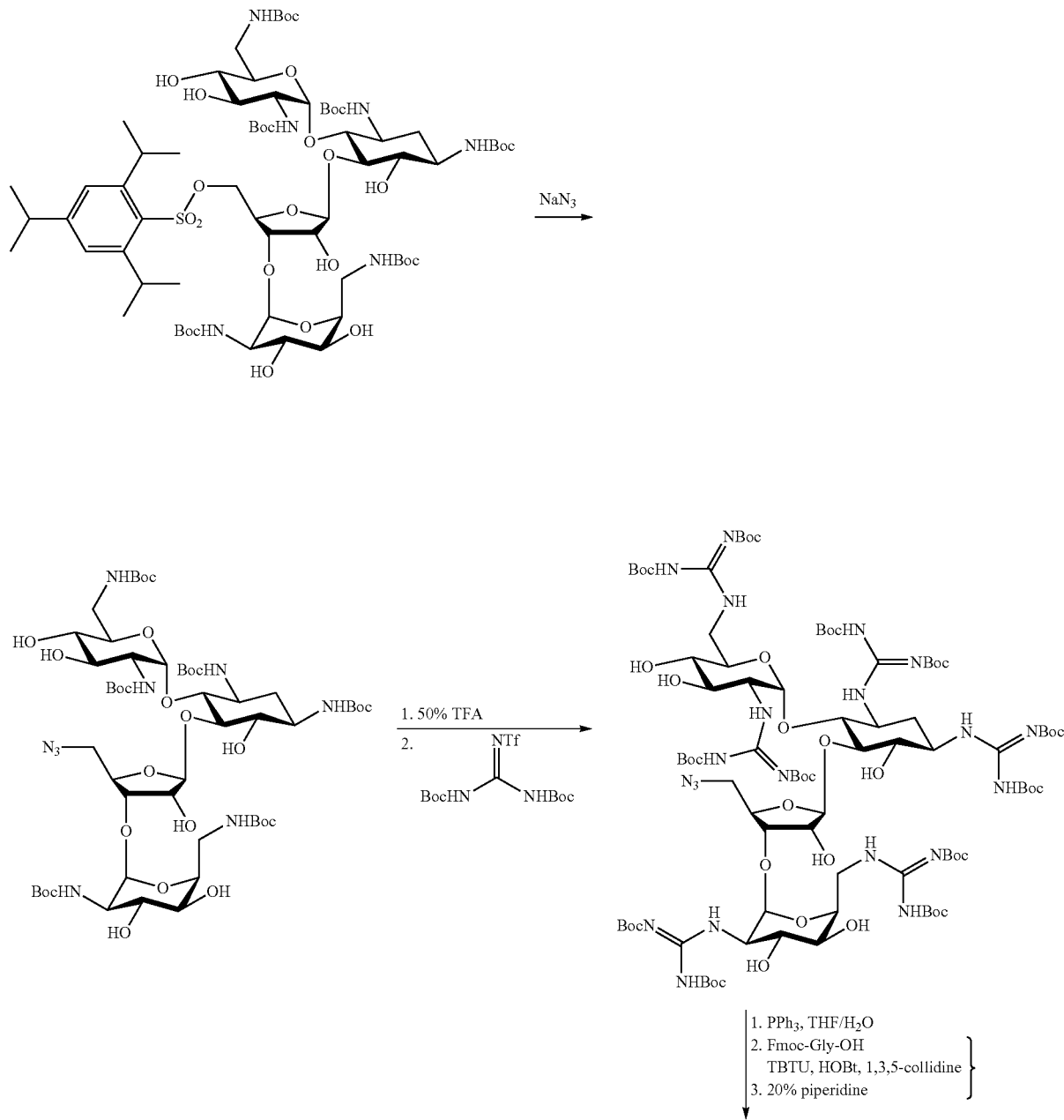

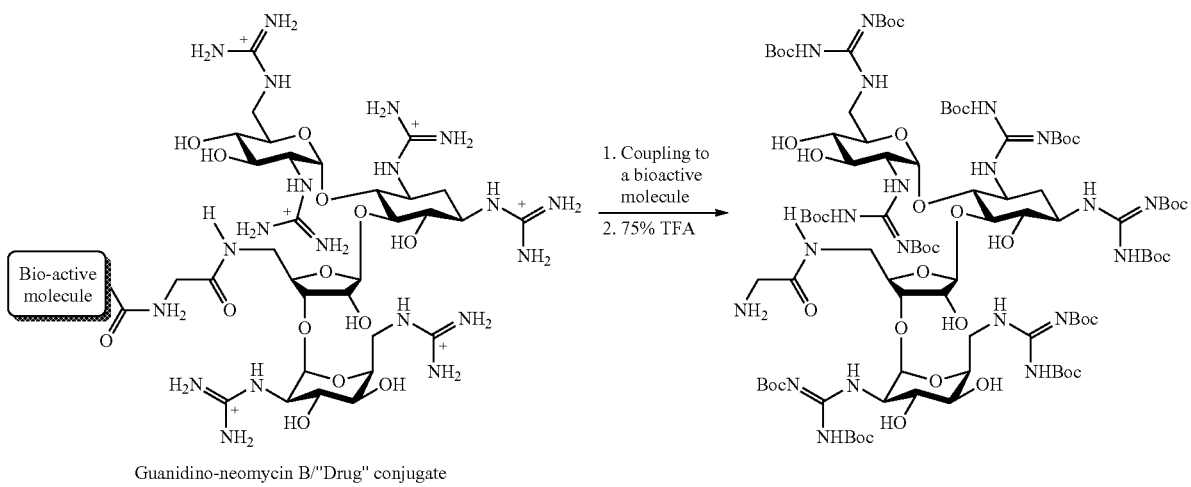

Guanidino-neomycin B/"Drug" conjugate

In one embodiment, the coupling of a bioactive molecule to a guanidinylated glycoside can be accomplished through an amino acid linker. In a related aspect, a 5"-TIPS activated Boc-protected neomycin B derivative can be reacted with sodium azide. The Boc groups can be then removed and the free amines can be reacted with a Boc-protected guanidinylating reagent (see, e.g., U.S. Pat. No. 6,525,182). Triphenol phosphine is then used to reduce the azido group into an amine. To this amine any bioactive molecule can be conjugated, with or without the use of a linker (e.g., nucleic acids, nucleosides, proteins, peptides, amino acid residues, lipids, carbohydrates, synthetic organic compounds, metals, vitamins, small molecules, dyes, isotopes, antibodies, toxins ligands or any other compound that may need transport into a cell). In some cases, the bioactive molecule can be a therapeutically active molecule such as a protein (e.g., an enzyme). In one embodiment, the amino acid glycine can be used as a linker between the bioactive molecule and the guanidinylated glycoside. Those having ordinary skill in the art would recognize that other amino acids may be substituted.

For thiols, a typical reaction Scheme can be as follows (Scheme III):

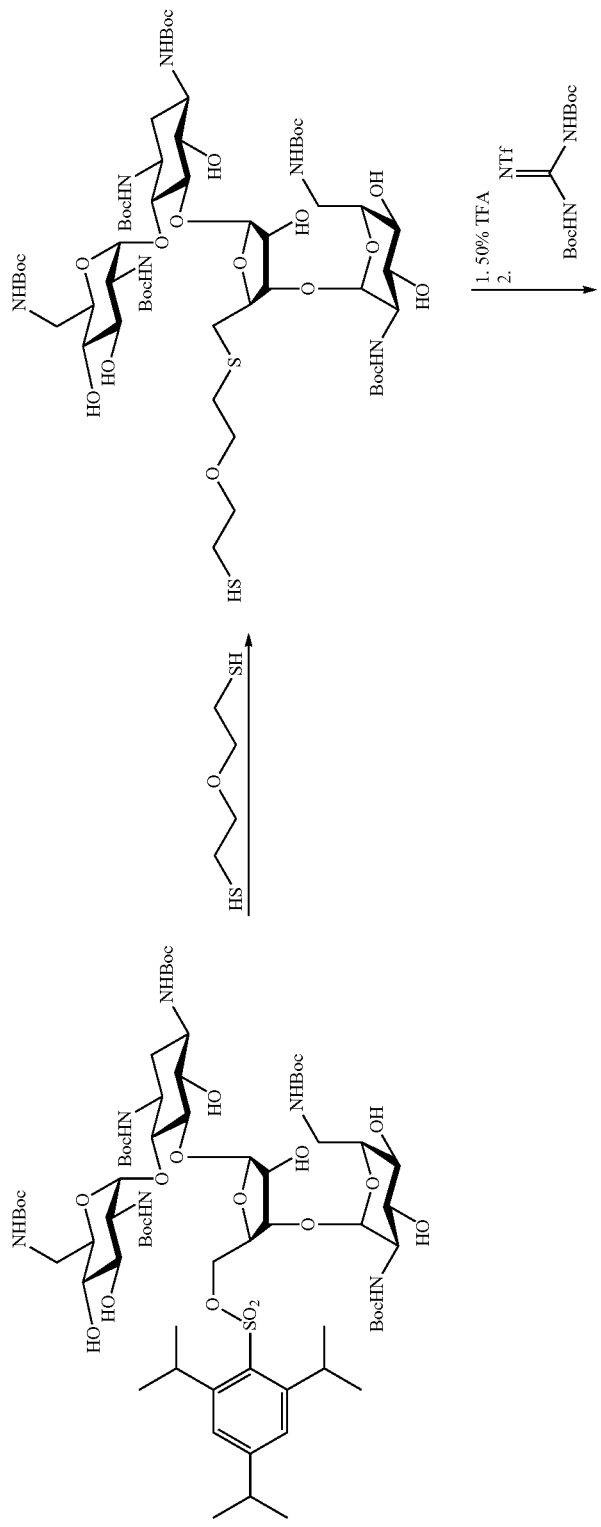

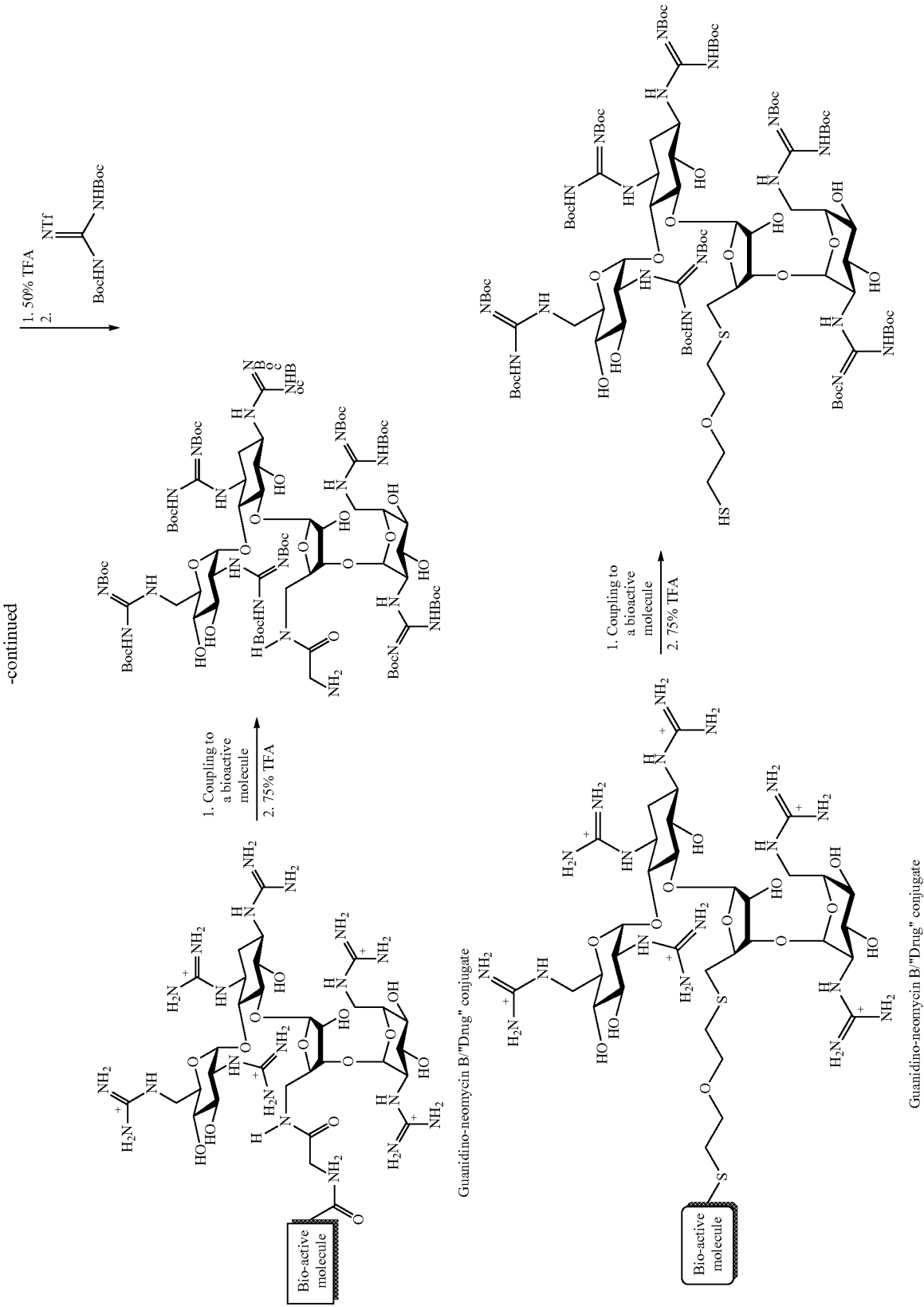

In one embodiment, the coupling of a bioactive compound to a guanidinylated glycoside can be accomplished through a thiol linker. In one aspect, a 5"-TIPS activated, Boc-protected neomycin derivative can be reacted with a dithiol. In one embodiment, the dithiol can be B-mercaptoethylether, but those having ordinary skill in the art would recognize that other similar dithiols may be used instead. The Boc groups can be then removed and the free amines are reacted with a Boc-protected guanidinylating reagent (see, e.g., U.S. Pat. No. 6,525,182). The coupling of the bioactive molecule through the free thiol can be performed either before or after the removal of the protecting groups (in the Scheme above, Boc) from the guanidine groups. This allows for the coupling reaction to be conducted under aqueous or non-aqueous conditions (e.g., depending on the solubility and reactivity of the bioactive molecule).

In some embodiments, a conjugate can be prepared comprising a guanidinoglycoside and an enzyme useful for the treatment of a lysosomal disorder. In some cases, the guanidinoglycoside can be covalently bound to the enzyme. The covalent bond between the moieties can be direct or can optionally include a linker. The conjugate can have the following structure:

GG-linker-enzyme wherein GG is a guanidinoglycoside.

For example, a guanidinoglycoside can be conjugated to the enzyme through a linker containing a terminal N-hydroxysuccinimide (NHS) activated ester conjugated to the guanidinoglycoside. This relatively reactive derivative can be prepared using a 2+3 cycloaddition reaction (commonly referred to as a Click reaction) between an NHS-activated azido carboxylic acid and an alkyne-linked guanidinoglycoside derivative (see Example 15). The necessary building blocks, including the singly modified aminoglycoside core, were prepared according to previously published procedures. Enzyme conjugates can then prepared by reacting the enzyme with GG-NHS at various ratios (e.g., ten-, 50-, and 100-fold molar excess of the NHS derivative). A high molar excess (>50-fold) can be used to achieve conjugation levels that enable binding to heparin-Sepharose. The following scheme illustrates the conjugation of guanidinoneomycin (GNeo) to NHS.

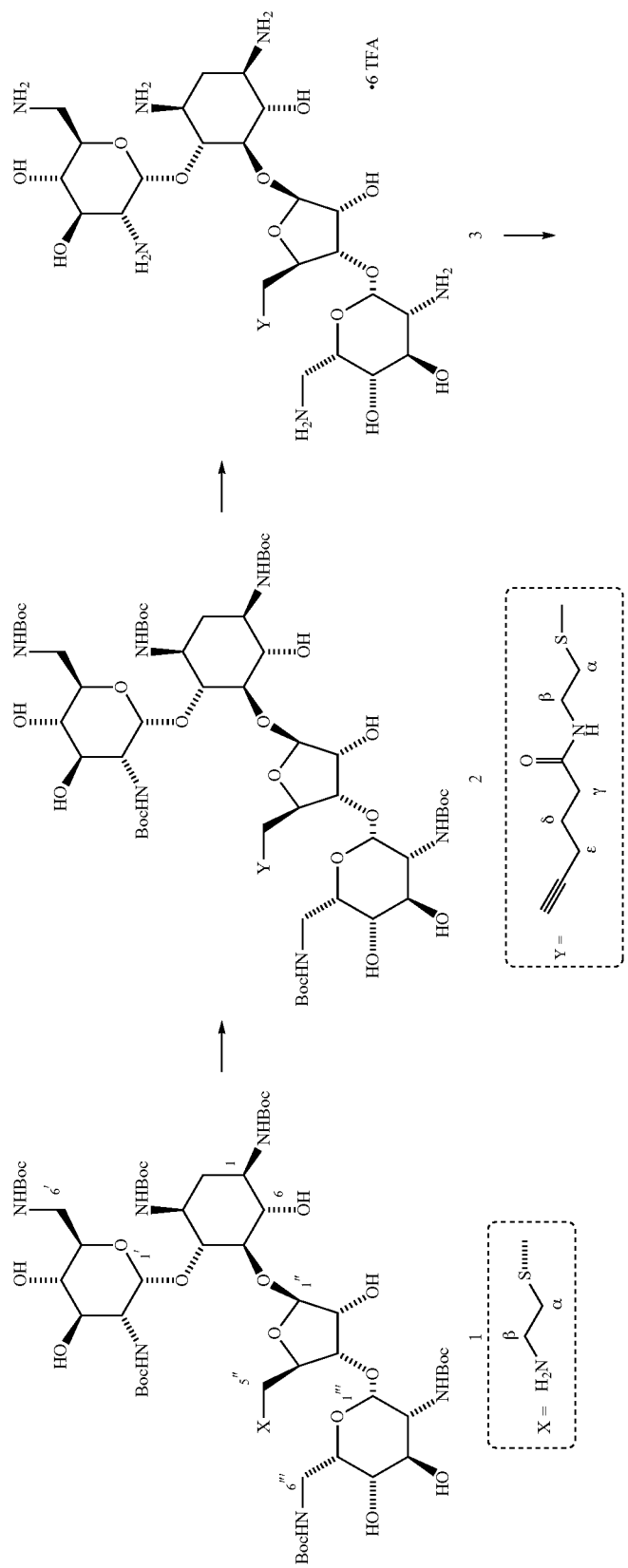

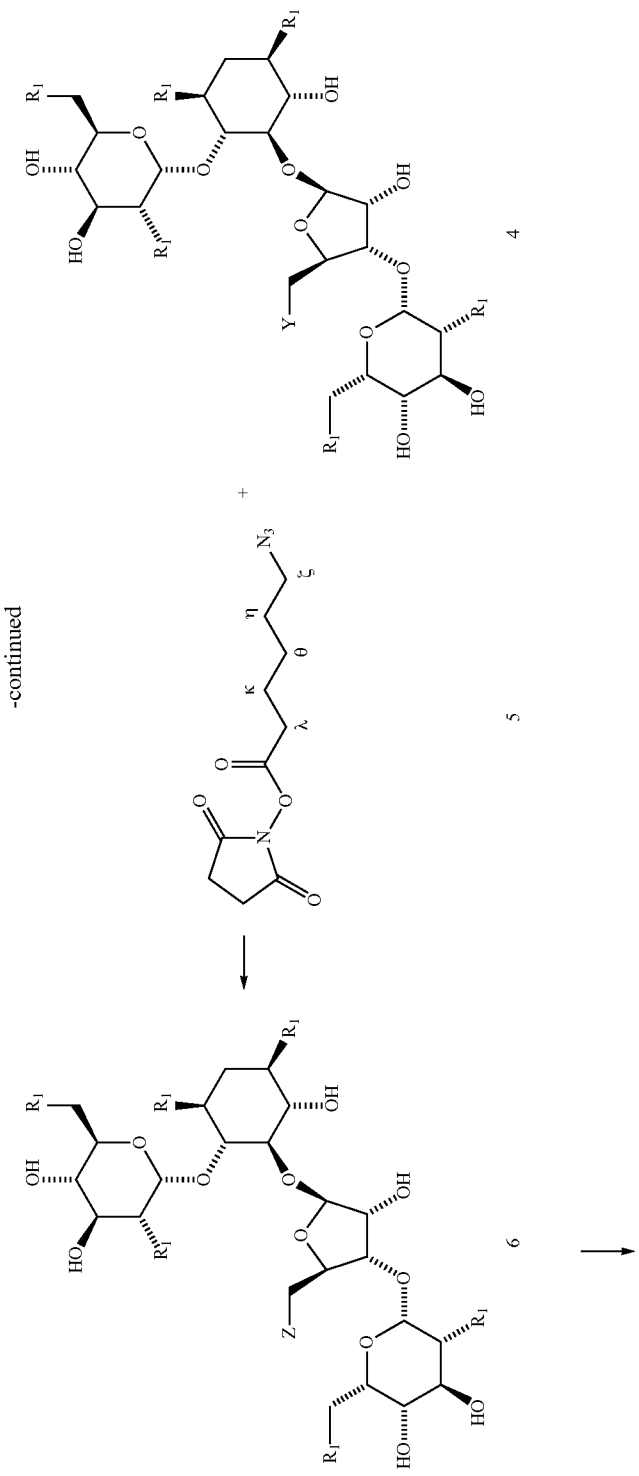

-continued
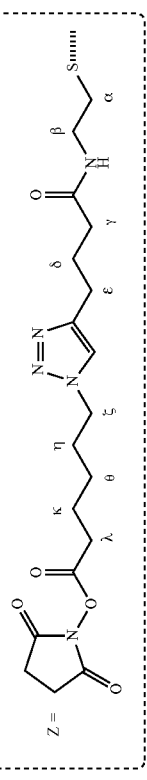
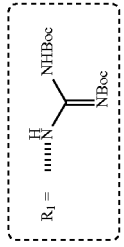
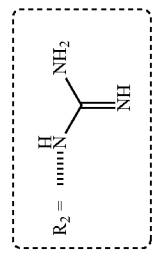
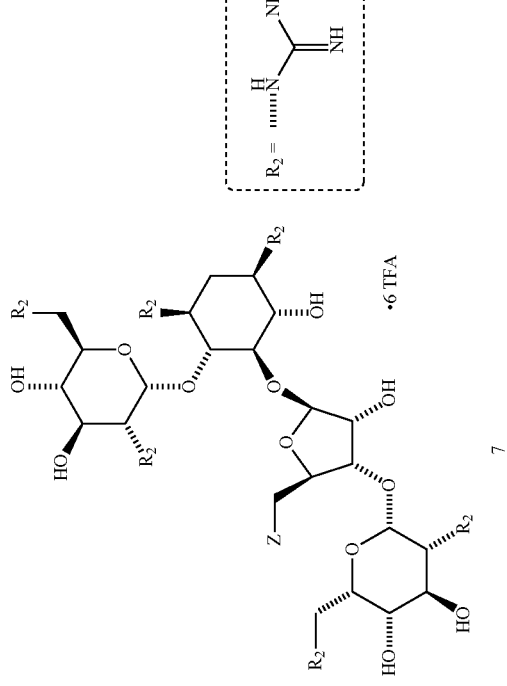

In some cases, the conjugates comprising an NHS linker can be represented by the following structure:

GG-NHS-enzyme wherein GG is a guanidinoglycoside, NHS is a linker comprising an N-hydroxysuccinimide moiety; and enzyme is an enzyme useful for the treatment of a lysosomal storage disease.

In another embodiment, a guanidinoglycoside can be noncovalently bound to the enzyme through a high affinity binding pair. As used herein, a "high affinity binding pair system" is a pair of reagents where a first member of the high affinity binding pair system binds to the second member of the high affinity binding pair system with a functional affinity (or avidity) sufficiently strong to allow stable aggregation of the guanidinoglycoside and the enzyme. A high affinity binding pair system typically exhibits an affinity between the first and second members of the high affinity binding pair of at least about $K\sim10^{-10}$. Suitable high affinity binding pairs include avidin and biotin, any protein that binds an immunoglobulin, and a ligand-receptor pair. Avidin includes avidin, modified avidin (such as deglycosylated avidin, neutravidin), streptavidin, and derivatives thereof, which bind biotin or its derivatives with high affinity. Proteins that bind an immunoglobulin include protein A, protein G, and protein L, and can be selected for their immunoglobulin specificity. Examples of ligand-receptor pairs that can serve as a high affinity binding pair include a small molecule and a macromolecule that binds the small molecule (for example, folic acid and a folate binding protein), and an antigen-antibody pair or hapten-antibody pair (for example, dinitrophenol, pyridoxal, or fluorescein and an appropriate anti-hapten antibody).

The guanidinoglycoside or the enzyme can be linked to either the first or second member of a high affinity binding pair. The guanidinoglycoside and the enzyme may be independently linked to the member of the high affinity binding pair directly or through a linker. In one example, biotin can be covalently linked to the guanidinoglycoside through a linker; the enzyme can then be non-covalently conjugated to the guanidinoglycoside via a covalent linkage of the enzyme to avidin, streptavidin, or neutravidin. Such a conjugate can have the following structure:

GG-biotin-streptavidin-enzyme.

In some cases, both the guanidinoglycoside and the enzyme are coupled (e.g., covalently linked) to the first member of a high affinity binding pair (e.g., biotin); the moieties are then conjugated through the second member of the binding pair. For example, the conjugate can have the following structure:

GG-biotin-streptavidin-biotin-enzyme.

Also provided herein is a conjugate comprising two or more guanidinoglycosides and a therapeutically active compound. In some cases, two guanidinoglycosides can be used. The guanidinoglycosides can be covalently bound to the enzyme (e.g., directly or optionally through a linker, such as polyethylene glycol, as described herein) or the guanidinoglycosides can be noncovalently bound to the enzyme through a high affinity binding pair. See, for example, Dix, A. V. et al., *Cooperative, Heparan Sulfate-Dependent Cellular Uptake of Dimeric Guanidinoglycosides*, ChemBioChem (2010) (in press) which is incorporated by reference in its entirety herein.

The following structures represent guanidinoglycosides bound to a linker moiety prior to coupling to an enzyme:

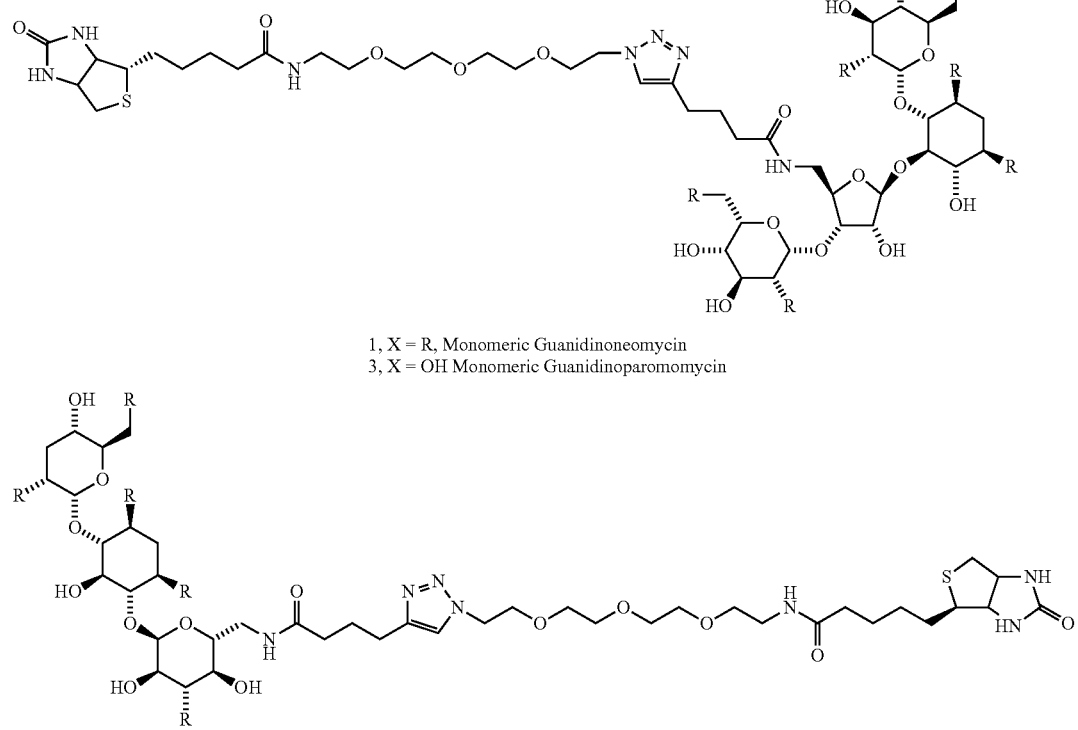

1, X = R, Monomeric Guanidinoneomycin
3, X = OH Monomeric Guanidinoparomomycin

5, Monomeric Guanidinotobramycin

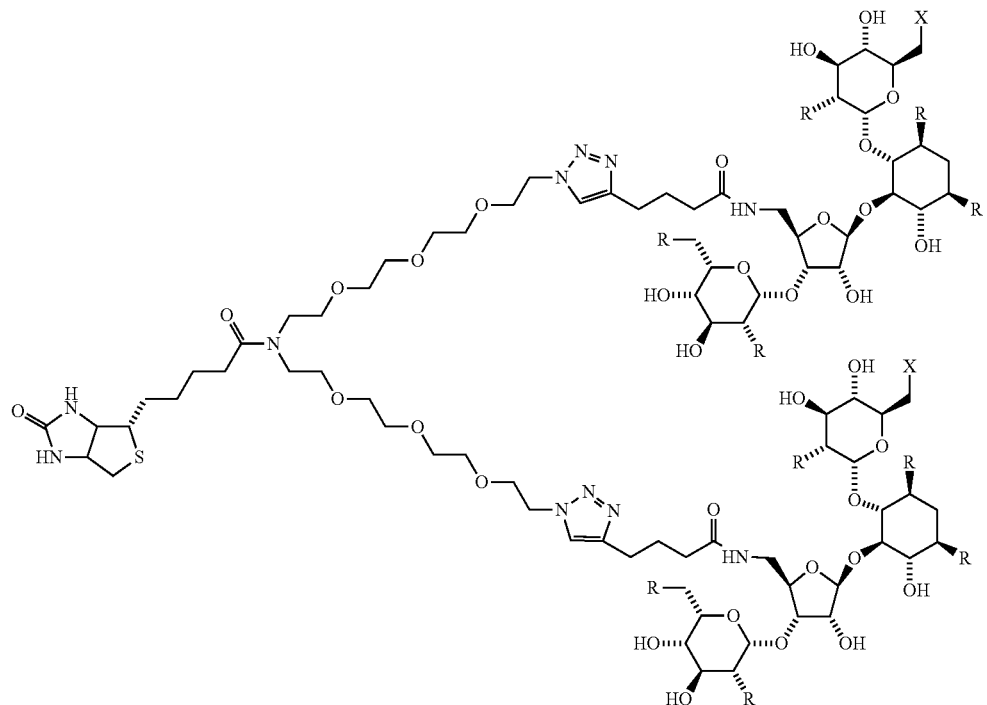
2, X = R, Dimeric Guanidinoneomycin
4, X = OH Dimeric Guanidinoparomomycin
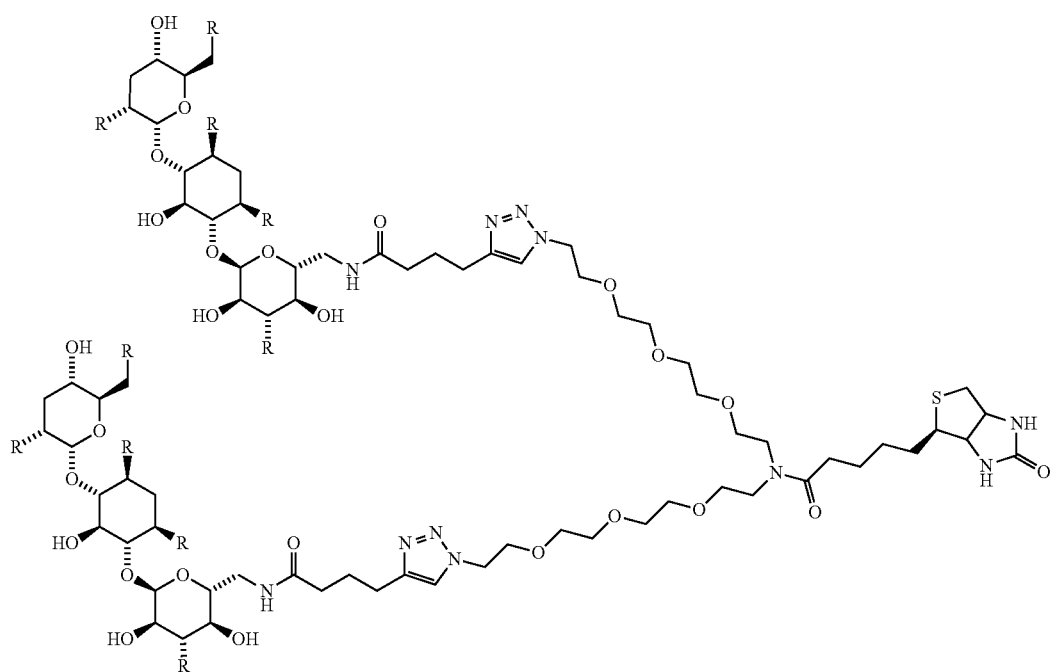
6, Dimeric Guanidinotobramycin
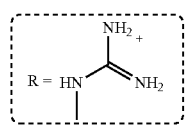

In one embodiment, a reversed phase HPLC can be used for purifying the final product (for example, the presence of the useful thymidine chromophore for UV-detection can be utilized). In another example the conjugates can be purified by chromatography on an heparin-sepharose column. In a related aspect, to facilitate the purification of intermediates, the guanidinoglycoside core can be maintained in its Boc-protected form. Such building blocks can be purified by normal phase chromatography.

As mentioned above, each functional component can be replaced by an alternative building block. In a related aspect, the parameters to be considered for advanced stages include the ability to tune the cellular uptake by using different guanidinoglycosides, the ability to tune the linker cleavage rate by substituting the benzene core in 4,9 or use other linkers with different release mechanisms, and the ability incorporate alternative nucleoside analogs.

In one embodiment, a method for treating a subject having a bacterial or viral infection or treating a subject susceptible to infection with a bacteria or virus is provided. The method includes administering a guanidinoglycoside-conjugate of the disclosure, an analogue, derivative, or salt thereof, prior to, simultaneously with, or subsequent to infection by a bacteria or viral organism.

In another embodiment, the disclosure provides a method of inhibiting or modulating the progression of viral infections (e.g., retroviral infections associated with HIV, HBV, and the like), bacterial infections, and disorders associated with, for example, inappropriate mitogenic signaling, non-insulin-dependent diabetes, and inhibition of disorders associated with thrombin, glycosidases, and nitric oxide synthases.

Thus, the guanidinoglycosides-containing conjugates of the present disclosure, as well as analogues, derivatives, or salts thereof are useful in the treatment of various maladies in general, either separately or in combination with other therapeutically active compounds. These compounds may be administered orally, topically or parenterally in dosage unit formulations containing conventional non-toxic pharmaceutically acceptable carriers, adjuvants, and vehicles.

The present disclosure also provides suitable topical, oral, and parenteral pharmaceutical formulations for use in the treatment of various illnesses. The compounds of the present disclosure may be administered orally as tablets, aqueous or oily suspensions, lozenges, troches, powders, granules, emulsions, capsules, syrups or elixirs. The composition for oral use may contain one or more agents selected from the group of sweetening agents, flavoring agents, coloring agents and preserving agents in order to produce pharmaceutically elegant and palatable preparations. The tablets contain the active ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The guanidinoglycoside-conjugates of the disclosure (including analogues, derivatives, or salts thereof) can be administered, for in vivo application, parenterally by injection or by gradual perfusion over time independently or together. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

The labels in the present disclosure can be primary labels (where the label comprises an element which is detected directly) or secondary labels (where the detected label binds to a primary label, e.g., as is common in immunological labeling). Primary and secondary labels can include undetected elements as well as detected elements. Useful primary and secondary labels in the present disclosure can include spectral labels such as fluorescent dyes (e.g., fluorescein and derivatives such as fluorescein isothiocyanate (FITC) and Oregon Green™ rhodamine and derivatives (e.g., Texas red, tetrarhodintine isothiocynate (TRITC), and the like), dixogenin, biotin, phycoerythrin, AMCA, CyDyes™, and the like), radiolabels (e.g., $^3$H, $^{125}$I, $^{35}$S, $^{14}$C, $^{32}$P, $^{33}$P, and the like), enzymes (e.g., horse-radish peroxidase, alkaline phosphatase, and the like) spectral calorimetric labels such as colloidal gold or colored glass or plastic (e.g., polystyrene, polypropylene, latex, and the like) beads. The label may be coupled directly or indirectly to Rev according to methods well known in the art. As indicated above, a wide variety of labels may be used, with the choice of label depending on sensitivity required, ease of conjugation with the compound, stability requirements, available instrumentation, and disposal provisions. In general, a detector is adapted to the particular label which is used. Typical detectors include X-ray machines, CAT scanners, NMR, spectrophotometers, phototubes and photodiodes, microscopes, scintillation counters, cameras, film and the like, as well as combinations thereof. Examples of suitable detectors are widely available from a variety of commercial sources known to persons of skill.

The examples of the labels that can be used include those which utilize (1) chemiluminescence (using horseradish peroxidase and/or alkaline phosphatase with substrates that produce photons as breakdown products) with kits being available, e.g., from Molecular Probes, Amersham, Boehringer-Mannhiem and Life Technologies/Gibco BRL; (2) color production (using both horseradish peroxidase and/or alkaline phosphatase with substrates that produce a colored precipitate; kits available from Life Technologies/Gibco BRL, and Boehringer-Mannheim); (3) hemifluorescence using, e.g., alkaline phosphatase and the substrate AttoPhos (Amersham) or other substrates that produce fluorescent products, (4) fluorescence (e.g., using Cy-5 (Amersham), fluorescein, and other fluorescent tags); and (5) radioactivity. Other methods for labeling and detection will be readily apparent to one skilled in the art.

The fluorescent labels that can be used are typically characterized by one or more of the following: high sensitivity, high stability, low background, low environmental sensitivity and high specificity in labeling. Fluorescent moieties, which can be incorporated into the labels of the disclosure include BODIPY, Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from various commercial sources, including Sigma Chemical Co. (St. Louis, Mo.), Molecular Probes, R&D systems (Minneapolis, Minn.), Pharmacia LKB Biotechnology (Piscataway, N.J.), Clontech Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.).

The following non-limiting examples are intended to further illustrate embodiments of the disclosure.

EXAMPLES

Figure 2:
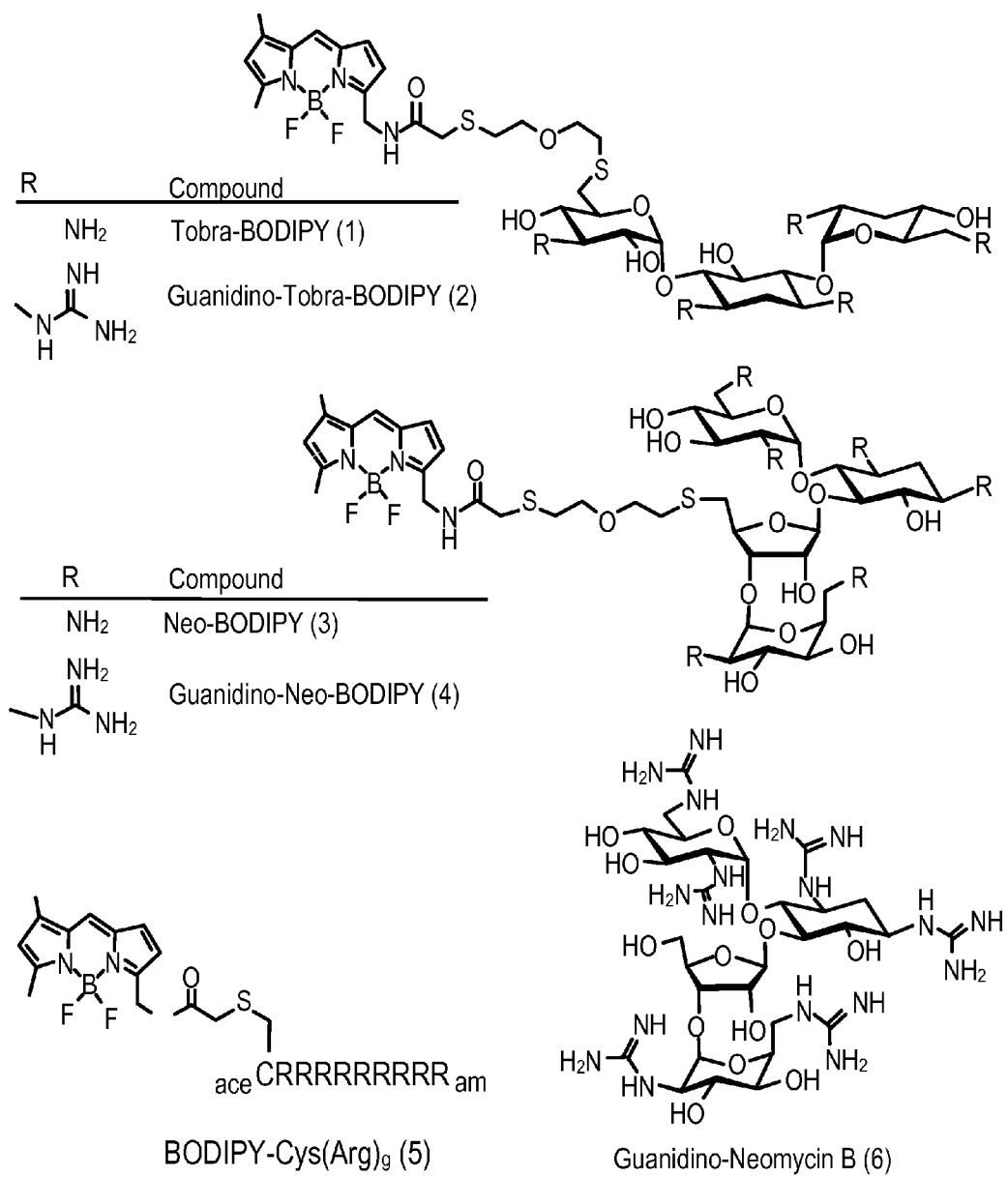
FIG. 2 illustrates the structures for the aminoglycosides and guanidinoglycosides conjugates used to evaluate cellular uptake.

To examine how the cellular uptake of conjugated compounds is affected by guanidinylation, a series of BODIPY-tagged aminoglycosides and guanidinoglycosides were synthesized based upon tobramycin and neomycin B (see, e.g., FIG. 2). The fluorescence of BODIPY is relatively insensitive to changes in the local environment. By using fluorescein as a reference ($\varphi$=0.93 at pH 9.0), the emission quantum efficiently ($\varphi$) of all five BODIPY conjugates described below is equal to 1.0 at pH 7.5.

Example 1

Synthesis and Characterization of Tobra-BODIPY

A general Scheme for synthesizing tobra-BODIPY is shown below (Scheme IV):

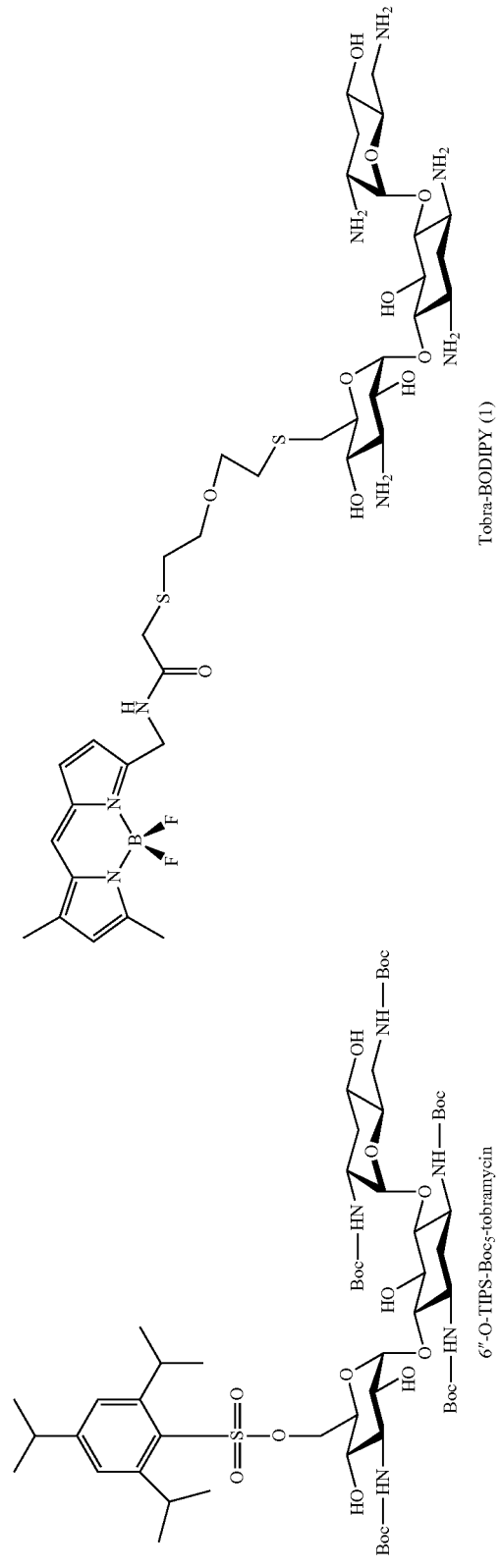

-continued
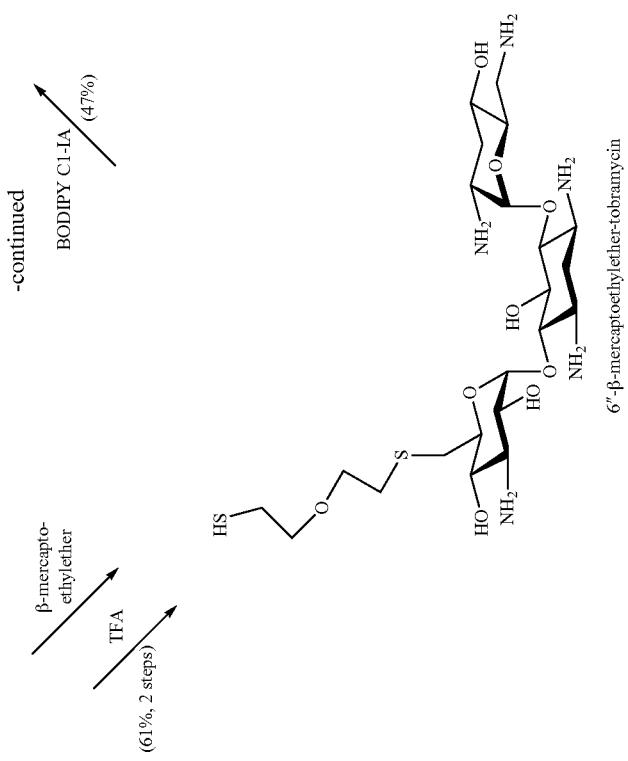

As a first step of the synthesis of tobra-BODIPY, 6"-O-TIPS-Boc$_5$-tobramycin was synthesized, as shown by the reaction Scheme V:

Scheme V

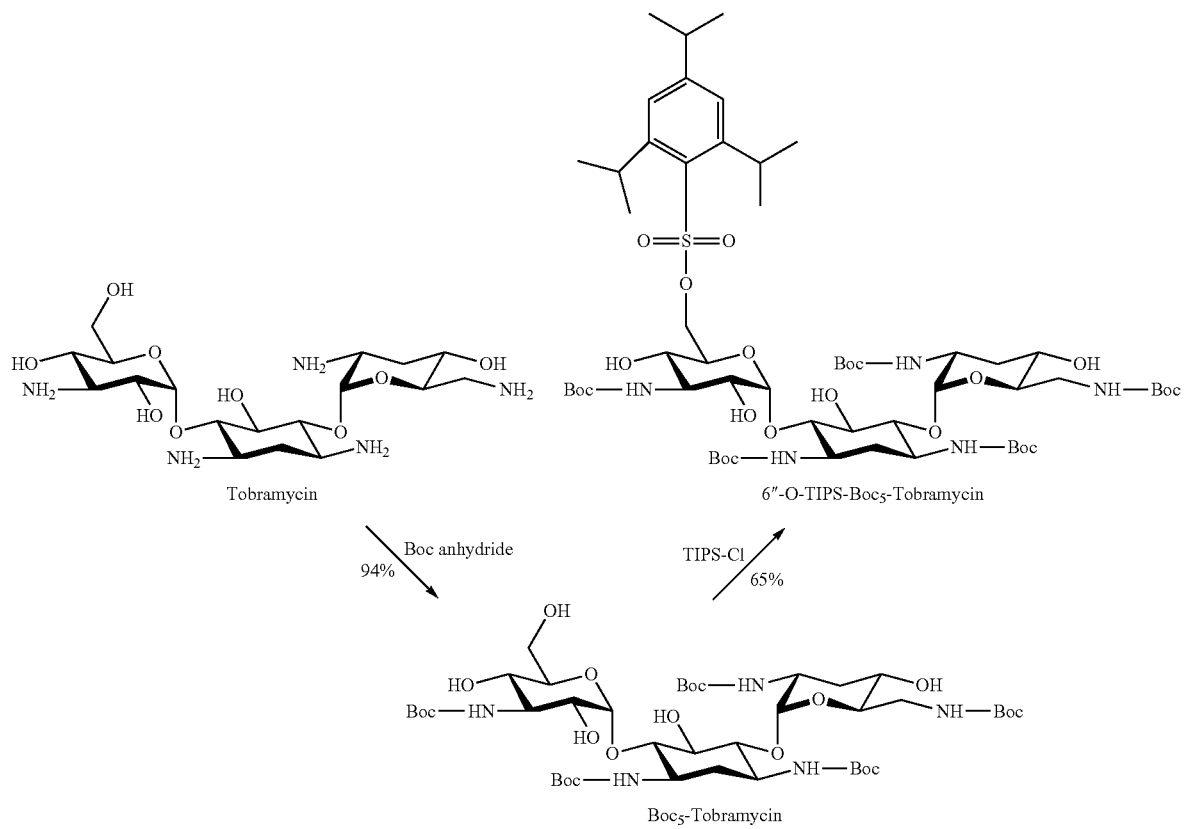

As shown by Scheme V, the first step of the synthesis of 6"-O-TIPS-Boc$_5$-tobramycin was the synthesis of Boc$_5$-tobramycin. To prepare Boc$_5$-tobramycin, a solution of tobramycin (0.5 g, 1.070 mmol) in 14 mL aqueous DMSO (DMSO: water=6:1) was treated with di-tert-butyldicarbonate (1.4 g, 6.420 mmol, 6.0 equiv). The solution was heated at 60° C. for 4 hours, then cooled to 23° C. A solution of 30% aqueous ammonia (5 mL) was added dropwise to the mixture. The precipitated solid was filtered, washed with water (3×200 mL), and dried in vacuo (970 mg, 94%): Rf 0.31, 7.5% methanol-dichloromethane; $^1$H NMR (500 MHz, methanol-$d_4$) 5.10 (br, 1H), δ 5.07 (br, 1H), δ 3.93 (m, 1H), δ 3.78 (m, 1H), δ 3.70 (m, 2H), δ 3.60 (m, 3H), δ 3.30-3.50 (m, 9H), δ 2.11 (m, 1H), δ 1.99 (m, 1H), δ 1.64 (q 1H, J=12.5 Hz), δ 1.42-1.48 (m, 46H); HRMS (FAB) m/z calcd for C$_{43}$H$_{77}$NaN$_5$O$_{19}$ [M+Na]+990.5110, found 990.5102.

To complete the synthesis of 6"-O-TIPS-Boc$_5$-tobramycin, a solution of Boc$_5$-tobramycin (0.3 g, 0.310 mmol) in pyridine (5 mL) was treated with 2,4,6-triisopropylbenzenesulfonyl chloride (0.66 g, 2.180 mmol, 7.0 equivalent). Boc$_5$-tobramycin was made as described above. The reaction mixture was stirred at 23° C. for 12 hours. It was neutralized by adding hydrochloric acid (1.0 N), and partitioned between water (300 mL) and ethyl acetate (600 mL). The aqueous layer was separated and extracted with ethyl acetate (2×250 mL). The combined organic layer was washed with brine, dried over Na$_2$SO$_4$, and concentrated in vacuum. Flash chromatography (2.3% methanol-dichloromethane) afforded the desired product as a white solid (240 mg, 65%): Rf 0.33, 7.5% methanol-dichloromethane; $^1$H NMR (500 MHz, methanol-$d_4$) 7.28 (s, 2H), δ 5.09 (br, 2H), δ 4.40 (m, 1H), δ 4.27 (m, 1H), δ 4.14 (m, 3H), δ 3.72 (t, 1H, J=10.4 Hz), δ 3.40-3.60 (m, 12H), δ 2.94 (m, 1H), δ 2.04 (m, 2H), δ 1.64 (q, 1H, J=12.0 Hz), δ 1.42-1.48 (m, 46H), δ 1.26 (m, 18H), HRMS (FAB) m/z calcd for C$_{58}$H$_{99}$NaN$_5$O$_{21}$S [M+Na]+1256.6451, found 1256.6487.

Next, 6"-β-mercaptoethylether-tobramycin trifluoroacetic acid was synthesized. To synthesize 6"-β-mercaptoethylether-tobramycin trifluoroacetic acid, 6"-O-TIPS-Boc$_5$-tobramycin (40 mg, 32 mmoles) made as described above was stirred under argon, for 2 hours, at 30° C. together with Cs$_2$CO$_3$ (21 mg, 64 mmoles), dry dimethylformamide (3 mL), and 2-mercaptoethylether (34 μl, 274 mmoles, 8.6 equiv), followed by dilution with ethyl acetate (100 mL), washing with water (4×50 mL) and brine (50 mL), and drying over sodium sulfate. The organic layer was then concentrated under to an oil reduced pressure, and kept under a high vacuum for 40 min. The crude product was dissolved in CH$_2$Cl$_2$ (2 mL), 1,2-ethanedithiol (15 μL), triisopropysilane (15 μL), and trifluoroacetic acid (3 mL), and stirred at room temperature for 15 min. The product was then diluted with toluene (50 mL) and concentrated to a solid at 50° C. under reduced pressure. The dilution and concentration procedure was performed twice. The white solid was then dissolved in water and (100 mL) and washed with CHCl3 (4×50 mL). The aqueous layer was concentrated under reduced pressure and twice lyophilized from 0.1%

TFA (3 mL in water) to yield 25 mg of a white powder (61% yield, two steps). $^{1}$H-NMR (400 MHz, D2O) δ 5.59 (d, J=3.6 Hz, 1H), δ 4.85 (d, J=4.0 Hz, 1H), δ 3.3-3.8 (m, 17H), δ 3.05 (d,d J1=13.6 Hz, J2=7.2 Hz, 1H), δ 2.94 (d,d J1=11.6 Hz, J2=2.4 Hz, 1H), δ 2.65-2.71 (m, 3H), δ 2.57 (t, J=6.4 Hz, 2H), δ 2.40 (d,t J1=12.8 Hz, J2=4.0 Hz, 1H), δ 2.14 (d, t J1=12.4 Hz, J2=4.4 Hz, 1H), δ 1.87 (q, J=11.2 Hz, 1H), δ 1.78 (q, J=12.8 Hz, 1H). ESI MS calculated for $C_{22}H_{45}N_5O_9S_2$: 587.3. found 588.2 [M+H]+.

The final product, tobra-BODIPY hydrochloride, shown as (1) on Scheme IV was then synthesized. 6"-β-mercapto-ethylether-tobramycin trifluoroacetic acid made as described above (5 mg, 4.3 mmoles) was dissolved in a degassed aqueous buffer (1 mL of 150 mM NaCl, 10 mM sodium phosphate pH 7.5, Ar sparged). Separately, BODIPY Cl-IA (2.5 mg, 6 mmoles, 1.4 equivalent Molecular Probes) was dissolved in dimethylsulfoxide (0.75 mL), and added, dropwise, to the tobramycin solution. The reaction was kept in the dark for 2 hours at room temperature, then diluted with water (8 mL) and loaded onto an activated C-18 reversed-phase cartridge (Waters, Sep-pack). The column was activated with 10 mL acetonitrile, 10 mL of water, the crude reaction was then loaded, washed with 1M NaCl (5 mL) and pure water (5 mL), then a 0-30% acetonitrile/water gradient was applied, and the fractions between 5-15% acetonitrile/water were collected and lyophilized to yield 2.2 mg (47%) of a red powder. All BODIPY-glycoside conjugates are slightly to moderately hygroscopic, therefore the absorption at 502 nm of each compound (in methanol) is used to confirm the yield of the conjugation reaction (taking ε502 nm=76,000 cm-1M-1). $^{1}$H-NMR (400 MHz, D$_2$O) δ 7.39 (s, 1H), δ 6.91 (d, J=4.0 Hz, 1H), δ 6.30 (d, J=4.0 Hz, 1H), δ 6.22 (s, 1H), δ 5.55 (d, J=3.6 Hz, 1H), δ 4.94 (d, J=4.0 Hz, 1H), δ 4.49 (s, 2H), δ 3.25-3.90 (m, 19H), δ 3.05 (d, d J1=13.6 Hz, J2=7.2 Hz, 1H), δ 2.93 (d,d J1=11.6 Hz, J2=2.4 Hz, 1H), δ 2.60-2.67 (m, 5H), δ 2.40 (s, 3H), δ 2.29 (d, t J1=12.4 Hz, J2=3.6 Hz, 1H), δ 2.10-2.14 (m, 4H), δ 1.84 (q, J=11.6 Hz, 1H), δ 1.66 (q, J=12.8 Hz, 1H). MALDI TOF MS calculated for $C_{36}H_{59}BF_2N_8O_{10}S_2$: 876.3 found 877.4 [M+H]+, found 899.3 [M+Na]+ found 915.4 [M+K]+.

Example 2

Synthesis and Characterization of Guanidino-Tobra-BODIPY

A Scheme for synthesizing guanidino-tobra-BODIPY is shown below (Scheme VI):

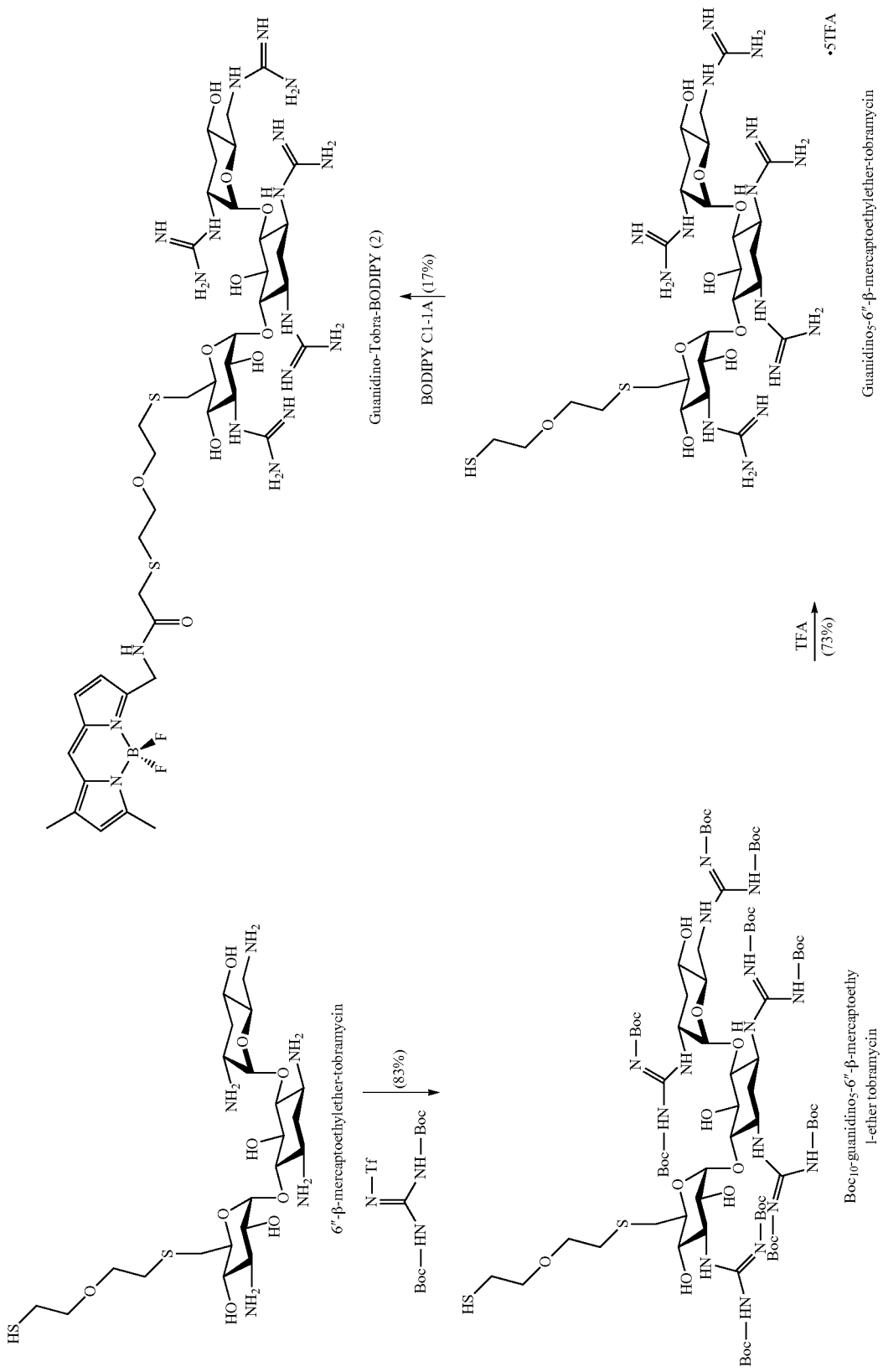

As shown by Scheme VI, the first step of the synthesis of guanidino-tobra-BODIPY was the synthesis of Boc$_{10}$-guanidino$_5$-6"-β-mercaptoethylether-tobramycin. To prepare Boc$_{10}$-guanidino$_5$-6"-β-mercaptoethylether-tobramycin, 6"-β-mercaptoethylether tobramycin trifluoroacetic acid made as described in Example 1 (70 mg, 60 μmoles), was dissolved in methanol (4 mL) and treated with N,N'-di-Boc-N"-triflylguanidine (420 mg, 1.08 mmoles, 17.9 equivalent), dithiothreitol (42 mg, 272 μmoles), and triethylamine (210 μL, 1.5 mmoles, 25 equivalent) for 26 hours at room temperature under argon. The product was then diluted by 150 mL of CHCl$_3$ and washed with 0.1M citric acid (three times, 50 mL each time) and brine (50 mL), then dried over sodium sulfate. The organic layer was concentrated to a solid and purified on silica gel using flash chromatography and 0-2% methanol in CH$_2$Cl$_2$ to afford 90 mg of an off-white solid (83% yield). $^1$H-NMR (400 MHz, CDCl$_3$) δ 11.50 (s, 1H), δ 11.47 (s, overlapping, 2H), δ 11.45 (s, 1H), δ 11.38 (s, 1H), δ 8.86 (d, J=3.6 Hz, 1H), δ 8.55 (d, J=9.0 Hz, 1H), δ 8.46 (t, J=6.3 Hz, 1H), δ 8.17 (d, J=8.7 Hz, 1H), δ 5.30-5.40 (m, 2H), δ 4.97 (d, J=3.9 Hz, 1H), δ 4.02 (br d, d=12 Hz, J$_2$=8.4 Hz, 1H), δ 3.78-3.94 (m, 2H), δ 3.31-3.72 (m, 10H), δ 3.18 (br d, d j$_1$=11.4 Hz, 2H), δ 2.95-3.03 (m, 2H), δ 2.61-2.73 (m, 8H), δ 2.36 (s, 1H), δ 2.02 (s, 1H), δ 1.93 (s, 1H), δ 1.62-1.69 (m, 18H), δ 1.42-1.51 (m, 18H), δ 1.28 (s, 1H). ESI MS calculated for C$_{77}$H$_{135}$N$_{15}$O$_{29}$S$_2$: 1797.8, found 1798.3 [M+H]$^+$, found 899.7 [M+2H]$^{2+}$.

Guanidino$_5$-6"-β-mercaptoethylether-tobramycin trifluoroacetic acid was then prepared by dissolving Boc$_{10}$-guanidino$_5$-6"-β-mercaptoethyelther-tobramycin (41 mg, 23 μmoles) in CHCl$_3$ (1 mL) and treating the solution with triisopropysilane (30 μL, 146 μmoles), 1,2-ethanedithiol (30 μL, 358 μmoles), and trifluoroacetic acid (1.5 mL) for 3 hours at room temperature. The product was then diluted with water (100 mL) and washed with CHCl$_3$ (twice, 30 mL each time) and diethyl ether (twice, 30 mL each time). The aqueous layer was concentrated to a solid under vacuum, then dissolved in 0.1% trifluoroacetic acid in water (2 mL) and lyophilized to yield 22 mg of a white solid (73% yield). $^1$H-NMR (400 MHz, d$_6$-MeOD) δ 5.65 (d, J=3.6 Hz, 1H), δ 5.06 (d, J=3.6 Hz, 1H), δ 4.10 (t, J=6.4 Hz, 1H), δ 3.45-3.88 (m, 17H), δ 3.04 (d,d J$_1$=13.6 Hz, J$_2$=2.8 Hz, 1H), δ 2.62-2.78 (m, 5H), δ 2.11-2.19 (m, 2H), δ 1.68-1.78 (m, 2H). MALDI TOF MS calculated for C$_{27}$H$_{55}$N$_{15}$O$_9$S$_2$: 797.37, found 820.32 [M+Na]$^+$.

The final product, guanidino-tobra-BODIPY hydrochloride shown as (2) on Scheme VI was then synthesized. Guanidino$_5$-6"-β-mercaptoethylether-tobramycin trifluoroacetic acid obtained as described above (10 mg, 4.3 μmoles) was added to an aqueous degassed buffer (2 mL of 50 mM sodium phosphate pH 7.5, Ar sparged). Separately, BODIPY Cl-IA (2.5 mg, 6 μmoles, 1.4 equivalent, Molecular Probes) was dissolved in dimethylsulfoxide (0.75 mL), and added, dropwise, to the tobramycin solution. The resulting precipitation of guanidino-tobramycin was partially reversed upon addition of NaCl (150 mM final concentration). The reaction was then kept in the dark for 2 hours at room temperature and diluted into 5% acetonitrile in water (15 mL, containing 100 mM NaCl) and loaded onto an activated C-18 reversed-phase cartridge (Waters, Sep-pack). The column was then washed with 5 mL of water and the product was eluted with 25% acetonitrile/water and lyophilized to yield 1.3 mg (17% yield) of a red powder. All BODIPY-glycoside conjugates are slightly to moderately hygroscopic, the absorption at 502 nm (in methanol) was used to calculate the yield of the conjugation reaction (taking ε502 nm=76,000 cm$^{-1}$M$^{-1}$). The low yield of this particular reaction was attributed to the solubility problems of the guanidino-tobramycin starting material in 50 mM phosphate/25% DMSO in water (its solubility in 10 mM sodium phosphate pH 7.5, 250 mM NaCl, 25% DMSO is, however, significantly better). $^1$H-NMR (400 MHz, D$_2$O) δ 7.41 (s, 1H), δ 6.92 (d, J=3.6 Hz, 1H), δ 6.31 (d, J=3.6 Hz, 1H), δ 6.24 (s, 1H), δ 5.40 (d, J=3.6 Hz, 1H), δ 4.98 (s, 1H), δ 4.51 (s, 2H), δ 4.03 (t, J=6.8 Hz, 1H), δ 3.79 (t, J=8.4 Hz, 1H), δ 3.27-3.64 (m, 18H), δ 2.90 (d, J=13.2 Hz, 1H), δ 2.55-2.67 (m, 5H), δ 2.41 (s, 3H), δ 2.02-2.15 (m, 5H), δ 1.54-1.62 (m, 2H). MALDI TOF calculated for C$_{41}$H$_{69}$BF$_2$N$_{18}$O$_{10}$S$_2$:1086.49, found 1087.36 [M+H]$^+$, found 1109.30 [M+Na]$^+$.

Example 3

Synthesis and Characterization of neo-BODIPY

A Scheme for synthesizing neo-BODIPY is shown below (Scheme VII):

As shown by Scheme VII, the first step of the synthesis of neo-BODIPY was the synthesis of 5"-O-TIPS-Boc$_6$-neomycin B. To prepare 5"-O-TIPS-Boc$_6$-neomycin B, Scheme VII

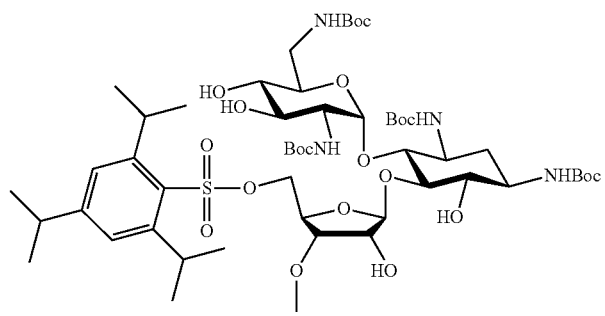

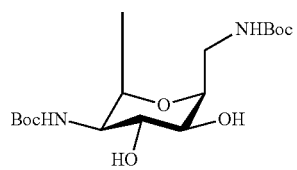
5″-O-TIPS-Boc$_6$-neomycin B
1) β-mercaptoethyl ether, DMF, Cs$_2$CO$_3$
2) TFA cocktail
(79%, 2 steps)
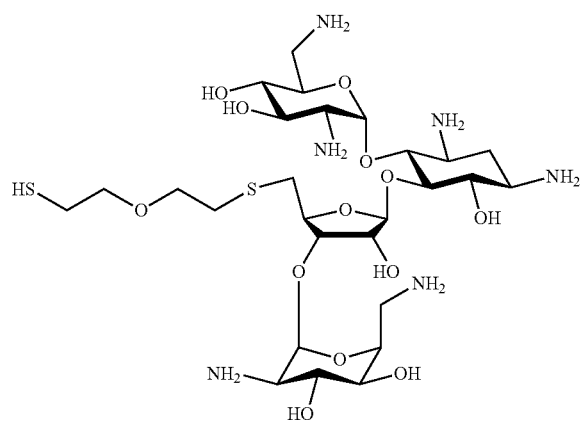
5″-β-mercaptoethylether-neomycin B
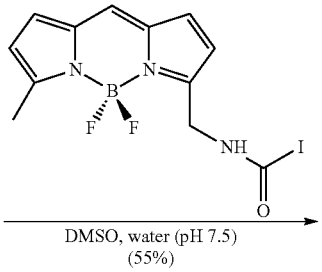
DMSO, water (pH 7.5)
(55%)
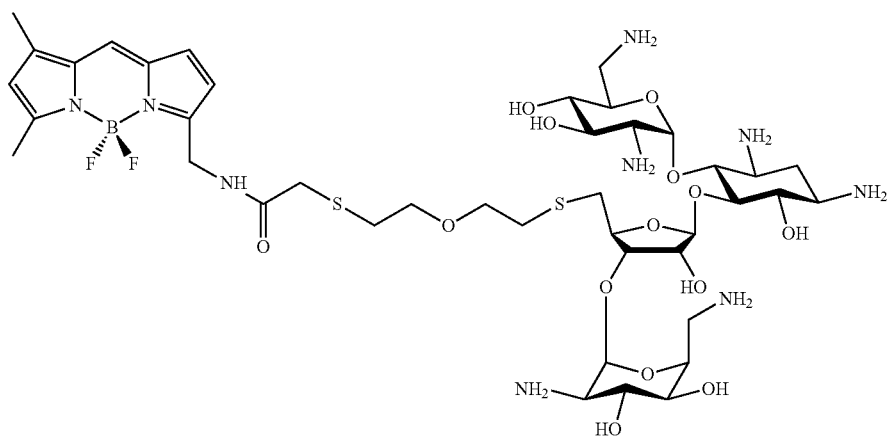
Neo-BODIPY
(3)

Scheme VIII

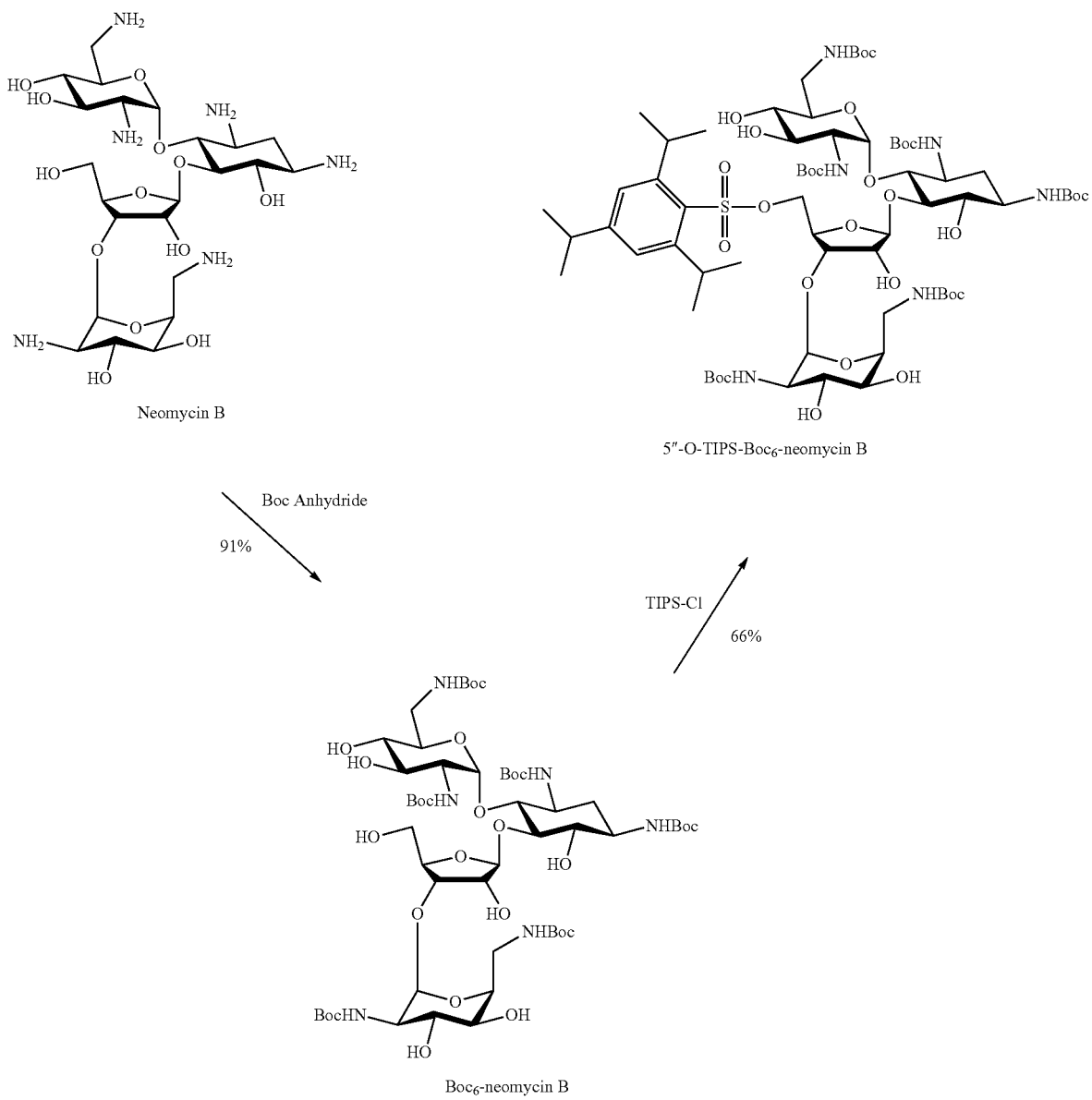

As shown by Scheme VIII, to prepare 5"-O-TIPS-Boc$_6$-neomycin B, Boc$_6$-neomycin B was made first. To prepare Boc$_6$-neomycin B, a solution of neomycin B (1.0 g, 1.626 mmol) in a mixture of diethylformamide (20 mL), water (4 mL) and triethylamine (2 mL) was treated with di-tert-butylcarbonate (2.1 g, 9.756 mmol, 6.0 equivalent). The reaction solution was heated to 60° C. for 5 hours, then cooled to 23° C. The volatile compounds were removed in vacuum. The residue was partitioned between water (300 mL) and ethyl acetate (600 mL). The aqueous layer was separated and extracted with ethyl acetate (twice, 250 mL each time). The combined organic layer was washed with brine, dried over Na$_2$SO$_4$, and concentrated in vacuum. Flash column chromatography (4.3% methanol-dichloromethane) afforded the desired product as a white solid (1.8 g, 91%): Rf 0.36, 10% methanol-dichloromethane; $^1$H NMR (500 MHz, methanol-$d_4$) 5.28 (br, 1H), 5.16 (s, 1H), 4.90 (s, 1H), 4.18 (s, 1H), 3.96 (s, 1H), 3.82-3.90 (m, 3H), 3.76 (s, 1H), 3.64-3.72 (m, 4H), 3.48 (m, 6H), 3.19-3.30 (m, 5H), 1.94 (m, 1H), 1.56 (m, 1H), 1.38-1.46 (m, 54H); HRMS (FAB) m/z calcd for C$_{54}$H$_{94}$NaN$_6$O$_{25}$[M+Na]+1237.6166 found 1237.6141.

Boc$_6$-neomycin B prepared as described above was then used to synthesize 5"-O-TIPS-Boc$_6$-neomycin B. A solution of Boc$_6$-neomycin B (1.0 g, 0.823 mmol) in pyridine (20 mL) was treated with 2,4,6-triisopropylbenzenesulfonyl chloride (8 g, 26.4 mmol, 32.0 equivalent). The reaction mixture was stirred at 23° C. for 12 hours. It was neutralized by adding hydrochloric acid (1.0; N) and partitioned between water (300 mL) and ethyl acetate (600 mL). The aqueous layer was separated and extracted with ethyl acetate (twice, 250 mL each time). The combined organic layer was washed with brine, dried over Na$_2$SO$_4$, and concentrated in vacuum. Flash chromatography (3.3% methanol-dichloromethane) afforded the desired product as a white solid (0.8 g, 66%): Rf 0.40, 10% methanol-dichloromethane; $^1$H NMR (500 MHz, methanol-$d_4$) 7.32 (2, 2H), 5.45 (br, 1H), 5.18 (br, 1H), 4.60 (br, 1H), 4.25 (m, 1H), 4.26 (m, 2H), 4.15 (m, 4H), 3.88 (s, 1H), 3.78 (m, 1H), 3.73 (m, 2H), 3.60 (m, 1H), 3.50 (m, 4H), 3.36-3.42 (m, 4H), 3.20 (m, 2H), 2.96 (m, 1H), 1.95 (m, 1H), 1.56 (m, 1H), 1.38-1.46 (m, 54H), 1.27 (m, 18H); HRMS (FAB) m/z calcd for $C_{68}H_{116}NaN_6O_{27}S$ [M+Na]+ 1503.7507, found 1503.7498.

5"-O-TIPS-Boc$_6$-neomycin B prepared as described above was then used to synthesize 5"-β-mercaptoethylether-neomycin trifluoroacetic acid. 5"-O-TIPS-Boc$_6$-neomycin B (40 mg, 27 μmoles) was dissolved in dimethylformamide (1.5 mL) and treated with $Cs_2CO_3$ (100 mg, 307 μmoles) and 2-mercaptoethylether (125 μL, 1 mmoles, 37 equiv). The reaction was kept under argon for 7 hours at 30° C., and the product was diluted with ethyl acetate (150 mL), washed with 0.1M citric acid (50 mL), water (three times, 50 mL each time), brine (50 mL), and dried over sodium sulfate. The organic layer was concentrated under reduced pressure and kept under a high vacuum overnight. The crude product was dissolved in $CH_2Cl_2$ (4 mL) and treated with 1,2-ethanedithiol (20 μL), triisopropysilane (20 μL), and trifluoroacetic acid (5 mL) for 15 min. at room temperature. The product was diluted with toluene (50 mL), concentrated under vacuum at 50° C. (twice) and kept under high-vacuum for 6 hours. The solid was then dissolved in 0.1% trifluoroacetic acid in water (3 mL), filtered through glass wool, and lyophilized to afford 30 mg of a white solid (79% yield, two steps). $^1$H-NMR (400 MHz, $D_2O$) δ 5.88 (d, J=4.0 Hz, 1H), δ 5.23 (d, J=3.2 Hz, 1H), δ 5.12 (s, 1H), δ 4.21-4.24 (m, 2H), δ 4.13-4.18 (m, 2H), δ 4.04 (s, 1H), δ 3.91 (t, J=10 Hz, 1H), δ 3.82 (t, J=9.6 Hz, 1H), δ 3.71-3.75 (m, 2H), δ 3.64 (s, 1H), δ 3.48-3.57 (m, 4H), δ 3.17-3.41 (m, 8H), δ 3.11 (d, d $J_1$=13.6 Hz, $J_2$=9.6 Hz, 1H), δ2.97 (d, d $J_1$=13.2 Hz, $J_2$=3.6 Hz, 1H), δ 2.65-2.74 (m, 4H), δ 2.55 (t, J=6.0 Hz, 2H), δ2.30 (d, t $J_1$=12.4 Hz, $J_2$=4.4 Hz, 1H), δ 1.71 (q, J=12.4 Hz, 1H). ESI MS calculated for $C_{27}H_{54}N_6O_{13}S_2$: 734.3, found 735.3 [M+H]$^+$.

5"-β-mercaptoethylether-neomycin trifluoroacetic acid prepared as described above was then used to synthesize the final product, neo-BODIPY hydrochloride, shown as (3) on Scheme VII. 5"-β-mercaptoethylether-neomycin B trifluoroacetic acid (10 mg, 7 μmoles), was dissolved in an aqueous buffer (1.5 mL of 10 mM sodium phosphate, 150 mM NaCl, pH 7.5, Ar sparged). Separately, BODIPY C1-IA (1.8 mg, 4.3 μmoles, 0.61 equivalent, Molecular Probes) was dissolved in dimethylsulfoxide (1.5 mL), and added, dropwise, to the neomycin solution and allowed to react in the dark for 2 hours at room temperature. The product was then diluted with water (8 mL) and loaded onto an activated C-18 reversed-phase cartridge (Waters, Sep-pack), the column was then washed with 5% acetonitrile (5 mL, containing 100 mM NaCl in water) and then pure water (1 mL). The product eluted between 0-15% acetonitrile (in water) and was lyophilized to yield 2.9 mg (55% yield) of a red powder. All BODIPY-glycoside conjugates are slightly to moderately hygroscopic, therefore the absorption at 502 nm of each compound (in methanol) is used to confirm the yield of the conjugation reaction (taking ε502 nm=76,000 cm$^{-1}$M$^{-1}$). $^1$H-NMR (400 MHz, $D_2O$) δ 7.41 (s, 1H), δ 6.92 (d, J=4.0 Hz, 1H), δ 6.30 (d, J=4.0 Hz, 1H), δ 6.24 (s, 1H), δ 5.89 (d, J=4.0 Hz, 1H), δ 5.27 (d, J=3.6 Hz, 1H), δ 5.15 (s, 1H), δ 4.50 (s, 2H), δ 4.26-4.32 (m, 2H), δ 4.21 (p, J=4.0 Hz, 1H), δ 4.15 (t, J=4.4 Hz, 1H), δ 4.07 (t, J=3.2 Hz, 1H), δ 3.83-3.88 (m, 3H), δ 3.77 (t, J=9.2 Hz, 1H), δ 3.67 (s, 1H), δ 3.53-3.59 (m, 4H), δ 3.45 (s, 1H), δ 3.40 (d, d $J_1$=11.2 Hz, $J_2$=4.0 Hz, 1H), δ 3.67 (s, 1H), δ 3.20-3.35 (m, 5H), δ 3.09 (d d, $J_1$=13.2 Hz, $J_2$=7.6 Hz, 1H), δ 2.98 (d d, $J_1$=13.6 Hz, $J_2$=4.4 Hz, 1H), δ 2.67-2.77 (m, 5H), δ 2.41 (s, 3H), δ 2.25 (d t, $J_1$=12.4 Hz, $J_2$=4.4 Hz, 1H), δ 2.15 (s, 3H), δ 1.65 (q, J=12.8 Hz, 1H). MALDI TOF MS calculated for $C_{41}H_{68}BF_2N_9O_{14}S_2$: 1023.44, observed 1024.42 [M+H]$^+$, observed 1046.43 [M+Na]$^+$, observed 1062.54 [M+K]$^+$.

Example 4

Synthesis and Characterization of Guanidine-neo-BODIPY

A Scheme for synthesizing guanidino-neo-BODIPY is shown below (Scheme IX):

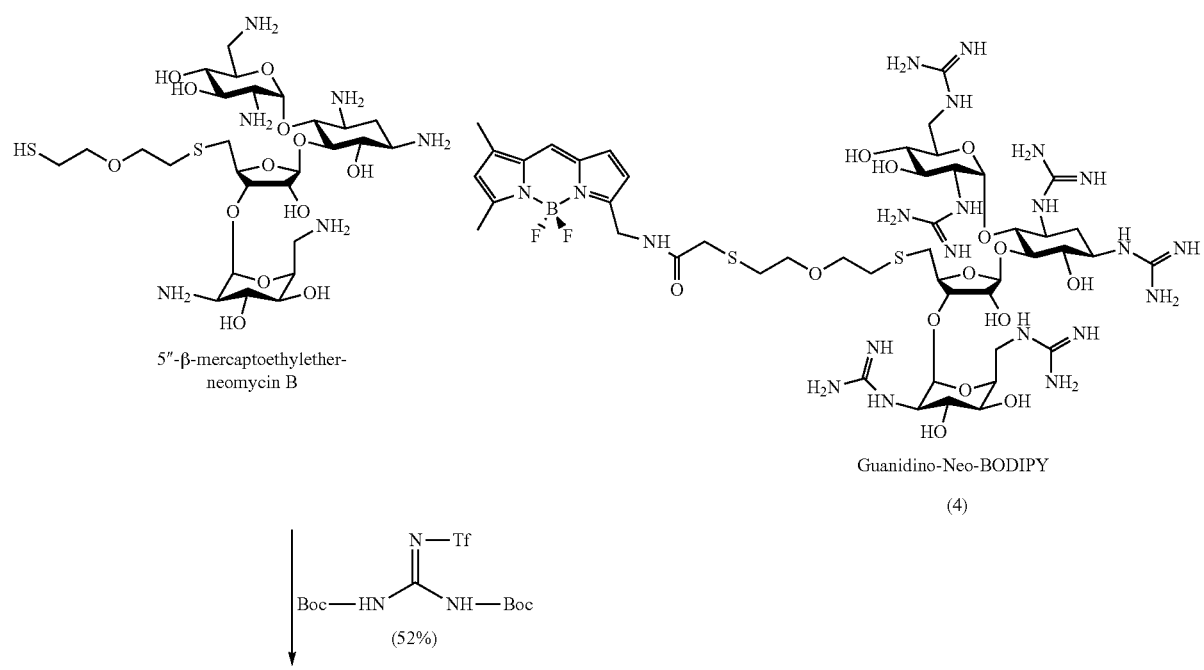

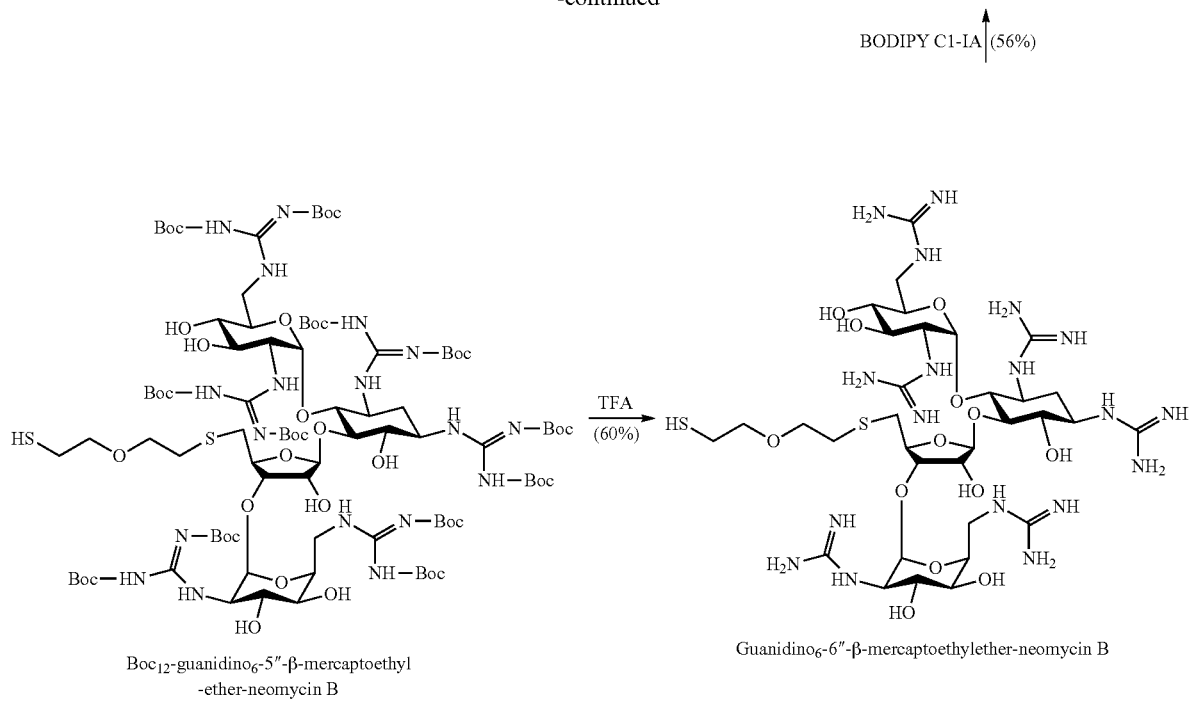

Boc$_{12}$-guanidino$_6$-5"-β-mercaptoethyl-ether-neomycin B

Guanidino$_6$-6"-β-mercaptoethylether-neomycin B

To prepare guanidino-neo-BODIPY, Boc$_{12}$-guanidino$_6$-5"-β-mercaptoethylether-neomycin B was made first. To prepare Boc$_{u}$-guanidino$_6$-5"-β-mercaptoethylether-neomycin B, 5"-β-mercaptoethylether-neomycin B trifluoroacetate synthesized as described in Example 3 (90 mg, 63 μmoles), was dissolved in methanol (5 mL), CHCl$_3$ (3 mL), and treated with N,N'-di-Boc-N"-triflylguanidine (530 mg, 1.35 mmoles, 21 equivalent), dithiothreitol (50 mg, 324 μmoles), and triethylamine (530 μL, 3.8 mmoles, 60 eqiv.) for 96 hours at room temperature under argon. The product was then diluted with CHCl$_3$ (200 mL) and washed twice with 0.1M citric acid (100 mL each time), brine (50 mL) and dried over sodium sulfate. The organic layer was then concentrated to a solid under reduced pressure and purified on silica gel using flash chromatography (0-1% methanol in CHCl$_3$ to afford 71 mg of an off-white solid (52% yield). $^1$H-NMR (300 MHz, CDCl$_3$) δ 11.41 (s, 2H, overlapping), δ 11.40 (s, 1H), δ 11.38 (s, 1H), δ 11.33 (s, 1H), δ 11.30 (s, 1H), δ 9.34 (d, J=8.1 Hz, 1H), δ 8.92 (d, J=7.2 Hz, 1H), δ 8.47 (t, J=5.4 Hz, 1H), δ 8.41 (t, J=5.4 Hz, 1H), δ 8.34 (d, J=6.6 Hz, 1H), δ 8.18 (d, J=9.0 Hz, 1H), δ 5.94 (d, J=4.4 Hz, 1H), δ 5.62 (d, J=4.2 Hz, 1H), δ 5.01 (d, J=4.8 Hz, 1H), δ 4.91-4.94 (m, 2H), δ 4.38-4.95 (m, 3H), 4.05-4.22 (m, 4H), δ 3.79-3.92 (m, 3H), δ 3.66-3.74 (m, 2H), δ 3.55-3.59 (m, 4H), δ 3.25-3.42 (m, 4H), δ 2.54-2.74 (m, 5H), δ 2.44 (d t, J$_1$=12.4 Hz, J$_2$=4.4 Hz, 1H), δ 1.22-1.60 (m, 109H). ESI MS calculated for C$_{94}$H$_{163}$N$_{17}$O$_{37}$S$_2$: 2186.1, found 1094.2 [M+2H]$^{2+}$.

Using Boc$_{12}$-guanidino$_6$-5"-β-mercaptoethylether-neomycin B made as described above, guanidino$_6$-5"-β-mercaptoethylether-neomycin B trifluoroacetic acid was then made. Boc$_{12}$-guanidino$_6$-5"-β-mercaptoethylether-neomycin B (65 mg, 30 μmoles) was dissolved in CHCl$_3$ (1.5 mL) and treated with triisopropylsilane (80 μL, 390 μmoles), 1,2-ethanedithiol (30 μL, 955 μmoles), and trifluoroacetic acid (3 mL) for 3 hours at room temperature. The product was then diluted into water (200 mL) and washed twice with CHCl$_3$ (100 mL each time) and twice with diethyl ether (50 mL each time). The aqueous layer was then concentrated to a solid under reduced pressure, dissolved in 0.1% trifluoroacetic acid in water (2 mL) and lyophilized to yield 30 mg of a white solid (60% yield). $^1$H-NMR (400 MHz, D$_2$O) δ 5.83 (d, J=3.2 Hz, 1H), δ 5.05 (s, 1H), δ 4.94 (s, 1H), δ 4.23-4.26 (m, 2H), δ 3.93-4.03 (m, 3H), δ 3.25-3.69 (m, 20H), δ 2.87 (d, d J$_1$=14.4 Hz, J$_2$=4.4 Hz, 1H), δ 2.55-2.67 (m, 5H), δ 2.08 (d t, J$_1$=12.0 Hz, J$_2$=4.4 Hz, 1H), δ 1.71 (q, J=12.0 Hz, 1H). MALDI TOF MS calculated for C$_{33}$H$_{66}$N$_{18}$O$_{13}$S$_2$: 986.45, found 987.49 [M+H]$^+$.

The final product, guanidino-Neo-BODIPY hydrochloride, shown as (4) on Scheme IX was then synthesized. Guanidino$_6$-5"-β-mercaptoethylether-neomycin B trifluoroacetic acid made as described above (9 mg, 5.4 mmoles) was dissolved in an aqueous buffer (3.0 mL of 10 mM sodium phosphate pH 7.5, 150 mM NaCl, Ar sparged). Separately BODIPY Cl-IA (1.7 mg, 4.1 mmoles, 0.76 equivalent, Molecular Probes) was dissolved in DMSO (1.5 mL), and added, dropwise, to the neomycin solution and allowed to react in the dark for 2 hours at room temperature. The product was then diluted with water (8 mL) and loaded onto an activated C-18 reversed-phase cartridge (Waters, Seppack). The column was washed with 5% acetonitrile (5 mL containing 100 mM NaCl in water) and pure water (1 mL). The product eluted between 0-20% acetonitrile (in water), and was lyophilized to yield 4.5 mg (56% yield) of a red powder. All BODIPY-glycoside conjugates are slightly to moderately hygroscopic, therefore the absorption at 502 nm of each compound (in methanol) is used to confirm the yield of the conjugation reaction (taking ε502 nm=76,000 cm$^{-1}$M$^{-1}$). $^1$H-NMR (400 MHz, D$_2$O) δ 7.40 (s, 1H), δ 6.92 (d, J=4.0 Hz, 1H), δ 6.31 (d, J=4.0 Hz, 1H), δ 6.24 (s, 1H), δ 5.84 (d, J=3.6 Hz, 1H), δ 5.07 (s, 1H), δ 4.91 (s, 1H), δ 4.51 (s, 2H), δ 4.21-4.24 (m, 2H), δ 3.93-4.00 (m, 3H), δ 3.80 (t, J=8.4 Hz, 1H), δ 3.66-3.71 (m, 2H), δ 3.25-3.55 (m, 15H), δ 2.80 (d, d J$_1$=14.4 Hz, J$_2$=4.4 Hz, 1H), δ 2.50-2.67

(m, 6H), δ 2.41 (s, 3H), δ 2.15 (s, 3H), δ 2.08 (d t, $J_1$=12.0 Hz, $J_2$=4.4 Hz, 1H), δ 1.57 (q, J=12.0 Hz, 1H). MALDI TOF MS calculated for $C_{47}H_{80}BF_2N_{210}O_{14}S_2$: 1275.57, found 1276.57 $[M+H]^+$.

Example 5

Synthesis and Characterization of BODIPY-Cys(Arg)$_9$

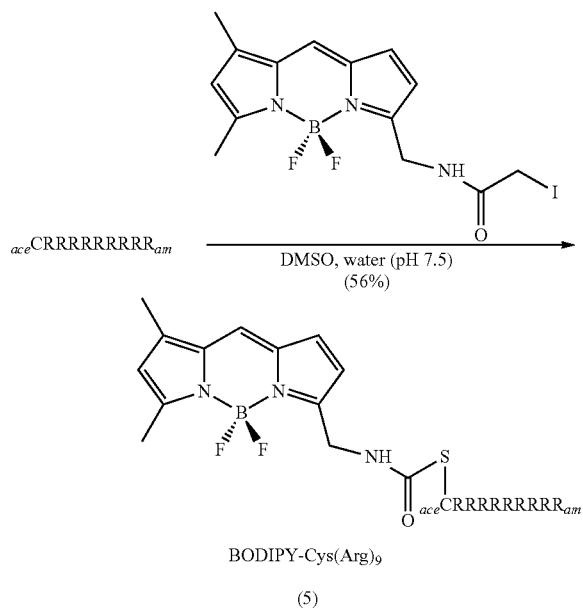

BODIPY-Cys(Arg)$_9$ (5)

A Scheme for synthesizing BODIPY-Cys(Arg)$_9$ is shown below (Scheme X):

total (as above). The final coupling reaction utilized Fmoc-Cys(Trt)-OH (264 mg, 0.45 mmoles), TBTU (145 mg, 0.45 mmoles), HOBt (46 mg, 0.45 mmoles), 2,4,6 collidine (0.6 mL, 4.5 mmoles), in DMF (7 mL) and lasted for 2 hours at room temperature on a shaker. Following de-protection and washes (as above), the terminus was acylated using HOBt (80 mg, 0.78 mmoles), diisopropylethylamine (0.9 mL), acetic anhydride (1.9 mL) in dimethylformamide (5 mL) for 1 hour at room temperature on a shaker. The resin was then washed three times with dimethylformamide (7 mL each time), twice with diethyl ether (7 mL each time), and four times with $CHCl_3$ (7 mL each time). The peptide was de-protected and cleaved from the resin using TFA (9 mL) in the presence of triisopropysilane (400 μl, 2 mmoles) and 1,2-ethanedithiol (0.2 mL, 6.4 mmoles) for 2.5 hours at room temperature on a shaker. The solution was drained into 1% acetic acid/water (180 mL), and washed three times with $CHCl_3$ (80 mL each time) and three times with diethyl ether (80 mL each time). The aqueous layer was then concentrated to a solid and lyophilized from 0.1% TFA in water. The crude peptide was purified using a 9% acetonitrile/water (0.1% TFA) isocratic mixture on a C-18 reversed phase HPLC column (3 mL/min, retention time 10-12 min) and lyophilized to yield a white solid (40 mg, 10%). MALDI TOF MS calculated for $C_{59}H_{118}N_{38}O_{115}$: 1566.96, found 1567.82 $[M+H]^+$.

Using the purified peptide ace-CRRRRRRRRR-am trifluoroacetic acid made as described above, the final product BODIPY-Cys(Arg)$_9$ hydrochloride shown as (5) on Scheme X, was then prepared. The purified peptide ace-CRRRRRRRRR-am trifluoroacetic acid (10 mg, 3.86 umoles) was dissolved in an aqueous degassed buffer (1 mL of 100 mM NaCl, 10 mM phosphate pH 7.5, Ar sparged) and treated (dropwise) with a solution of BODIPY C1-IA (1.3 mg, 3.1 μmoles, 0.81 equivalent, Molecular Probes) that was pre-dissolved in DMSO (1.25 mL). The reaction was allowed to react in the dark for 1 h at room temperature, the product was then diluted with 8 mL of water and loaded onto Scheme X

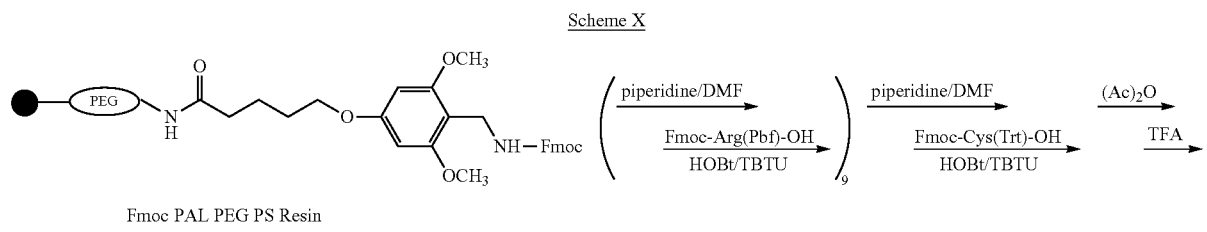

To synthesize BODIPY-Cys(Arg)$_9$, ace-CRRRRRRRRR-am trifluoroacetatic acid. To make ace-CRRRRRRRRR-am trifluoroacetatic acid, standard Fmoc solid-phase synthesis was used. Fmoc PAL PEG PS resin (1 g, 0.15 mmole, PerSeptive Biosystems), was de-protected using 20% piperidine in dimethylformamide for 20 minutes at room temperature, washed three times with dimethylformamide (7 mL each time), twice with diethyl ether (7 mL each time), and again three times with dimethylformamide (7 mL each time). The resin was then treated with TBTU (97 mg, 0.3 mmoles), Fmoc Arg (Pbf)-OH (195 mg, 0.3 mmoles), HOBt (46 mg, 0.3 mmoles), 2,4,6 collidine (0.4 mL, 3.0 mmoles), in DMF (7 mL), for at least 1 hour at room temperature on a shaker. The resin was then washed as above. The de-protection and coupling processes were repeated nine times an activated C-18 reversed-phase cartridge (Waters, Seppack). The column was washed with 5% acetonitrile (5 mL containing 100 mM of NaCl in water) and 1 mL pure water. The product eluted between 0-20% acetonitrile (in water) and was lyophilized to yield 3.8 mg (56% yield) of a red powder. All BODIPY-glycoside conjugates are slightly to moderately hygroscopic, therefore the absorption at 502 nm (in methanol) of each compound was used to confirm the yield of the conjugation reaction (taking ε502 nm=76,000 $cm^{-1}M^{-1}$). $^1$H-NMR (400 MHz, $D_2O$) δ 7.43 (s, 1H), δ 6.91 (d, J=3.6 Hz, 1H), δ 6.29 (d, J=3.6 Hz, 1H), δ 6.25 (s, 1H), δ 4.53 (s, 2H), δ 4.32 (t, J=7.2 Hz, 1H), δ 4.13-4.23 (m, 10H), δ 3.34 (s, 2H), δ 2.96-3.08 (m, 18H), δ 2.86 (d, J=6.8 Hz, 2H), δ 2.42 (s, 3H), δ 2.17 (s, 3H), δ 1.89 (s, 3H), δ 1.50-1.71 (m, 36H). The $^1$H NMR suggests better than 95% purity for this, and all other compounds evaluated. MALDI TOF MS calculated for $C_{23}H_{132}BF_2N_{41}O_{12}S$: 1856, found 1857 $[M+H]^+$.

Example 6

Synthesis and Characterization of tris-BODIPY

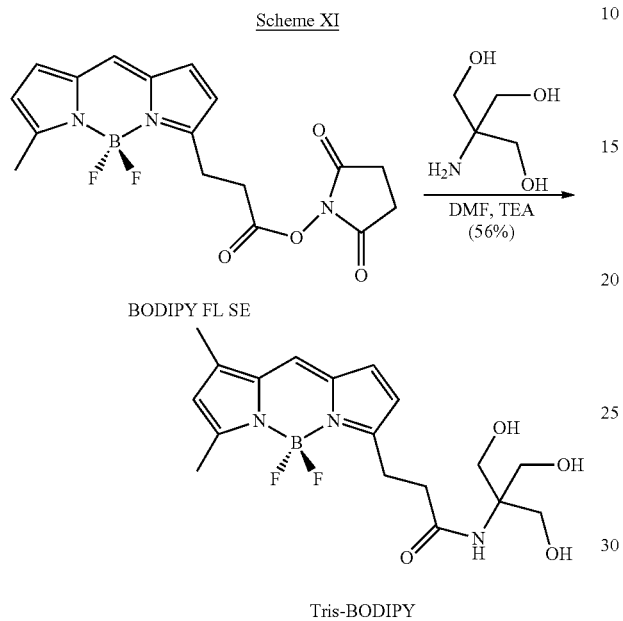

A Scheme for synthesizing tris-BODIPY is shown below (Scheme XI):

To synthesize tris-BODIPY, the following procedure was used. BODIPY FL SE (Molecular Probes) (~0.4 mg, ~1 µmoles) was dissolved in dimethylformamide (1 ml), and treated with Trisma base (10 mg, 126 µmoles) and triethylamine (10 µl, 72 µmoles) for 1 hour at room temperature in the dark. The product was diluted with 8 ml of 50 mM phosphate (pH=7.5) and loaded onto an activated C-18 reversed-phase cartridge (Waters, Sep-pack). The column was washed with 5 ml of pure water. The desired product eluted with 30% acetonitrile (in water), and was lyophilized to yield ~0.2 mg (56% yield) of a red powder. All BODIPY-glycoside conjugates are slightly to moderately hygroscopic, therefore the absorbance at 502 nm (in methanol) of each compound is used to calculate the yield of the conjugation reaction (taking $\epsilon 502$ nm=76,000 $cm^{-1}M^{-1}$). $^1$H-NMR (400 MHz, MeOD) δ 7.43 (s, 1H), δ 7.00 (d, J=4.0 Hz, 1H), δ 6.35 (d, J=4.0 Hz, 1H), δ 6.21 (s, 1H), δ 3.71 (s, 6H), δ 3.21 (t, J=8.0 Hz, 2H), δ 2.68 (t, J=8.0 Hz, 2H), δ 2.50 (s, 3H), δ2.28 (s, 3H), ESI MS calculated for $C_{18}H_{24}BF_2N_3O_4$: 395.2, found 418.3 $[M+Na]^+$

Example 7

Synthesis and Characterization of Amino-Tobra-Fluorescein

A Scheme for synthesizing amino-tobra-fluorescein is shown below (Scheme XII):

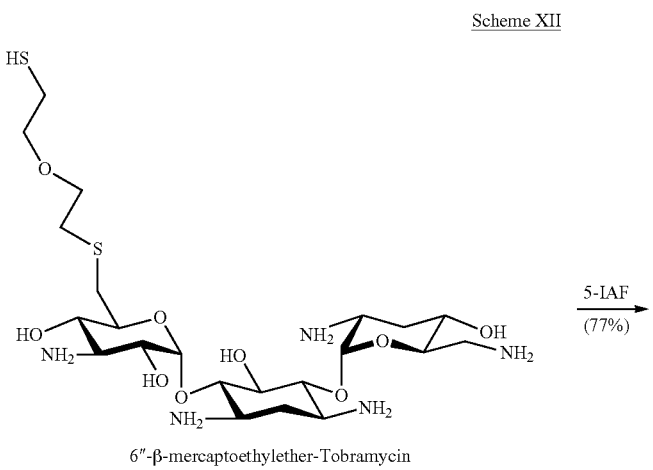

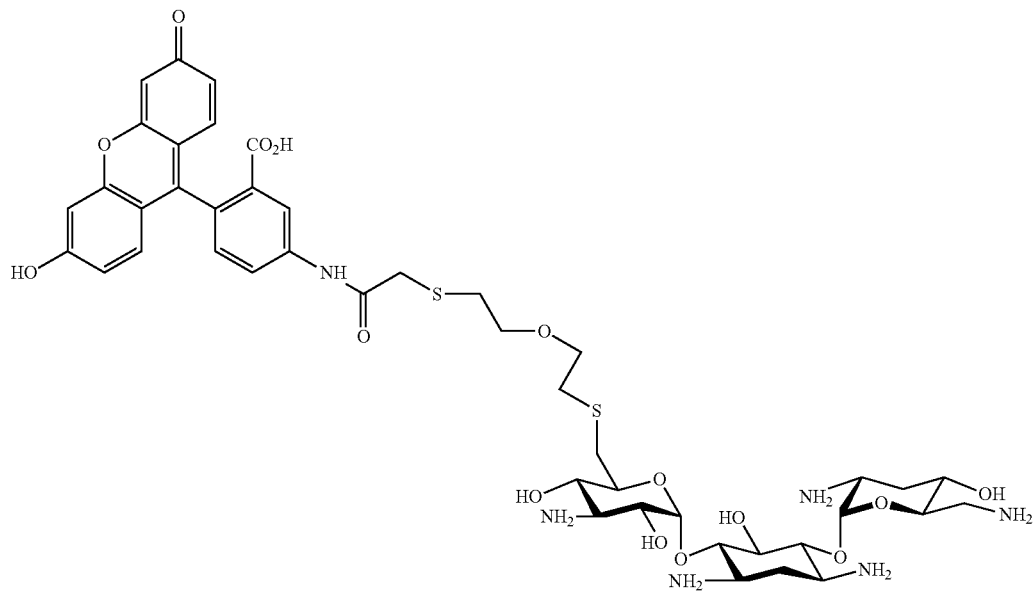

Amino Tobra-Fluorescein

6''-β-mercaptoethyl ether tobramycin.trifluoroacetic acid, prepared as described in Example 1 (3 mg, 2.6 μmoles), was dissolved in an aqueous degassed buffer (2 mL of 400 mM NaCl, 25 mM sodium phosphate, pH=7.5, Ar sparged), separately 5-iodo-acetamido-fluorescein (5-IAF) (3.0 mg, 5.8 μmoles, 2.0 equivalent, Molecular Probes) was dissolved in dimethylsulfoxide (1 mL), and added, dropwise, to the tobramycin solution and allowed to react in the dark for 2 h at room temperature, followed by adding 0.1M HCl, until the solution turned from orange to yellow. The product was then diluted with water (8 mL) and loaded onto an activated C-18 reversed-phase cartridge (Waters, Sep-pack), the column was then washed with pure water (10 mL), and the product was eluted with 20% acetonitrile/water, lyophilized, and found to be >95% pure by HLPC. The product was purified further using a C-18 reversed phase HPLC column with an isocratic mixture of 20% acetonitrile (0.1% TFA) in water (0.1% TFA) (3 mL/min) (Rt=8.5 min) to yield 3.3 mg (77%) of an orange solid. All fluorescein-glycoside conjugates are slightly to moderately hygroscopic, therefore the absorption at 496 nm (in aqueous buffer pH 9.0) of each compound is used to confirm the yield of the conjugation reaction (taking $\epsilon_{502\ nm}$=77,000 cm$^{-1}$M$^{-1}$). $^1$H-NMR (400 MHz, D$_2$O) 8.13 (d, J=2.0 Hz, 1H), 7.67 (d,d J$_1$=8.4 Hz, J$_2$=1.6 Hz, 1H), 7.15-7.22 (m, 3H), 6.93 (d, J=2.4 Hz, 2H), 6.77-6.80 (m, 2H), 5.53 (d, J=2.8 Hz, 1H), 4.85 (d, J=3.6 Hz, 1H), 3.22-3.83 (m, 21H), 3.05 (d,d J$_1$=13.2 Hz, J$_2$=7.2 Hz, 1H), 2.87 (d,d J$_1$=11.6 Hz, J$_2$=2.0 Hz, 1H), 2.77 (t, J=5.8 Hz, 2H), δ 2.57-2.65 (m, 3H), δ 2.36 (d,t J$_1$=12.0 Hz, J$_2$=3.6 Hz, 1H), 2.09 (d,t J$_1$=12.4 Hz, J$_2$=3.6 Hz, 1H), 1.83 (q, J=11.6 Hz, 1H), 1.74 (q, J=12.4 Hz, 1H). MALDI TOF MS calculated for C$_{44}$H$_{58}$N$_6$O$_{15}$S$_2$: 974.34 found 975.42 [M+H]$^+$. found 997.43 [M+Na]$^+$ found 1013.41 [M+K]$^+$.

Example 8

Synthesis and Characterization of GuanidinoTobra-Fluorescein

A Scheme for synthesizing guanidino-tobra-fluorescein is shown below (Scheme XIII):

Scheme XIII

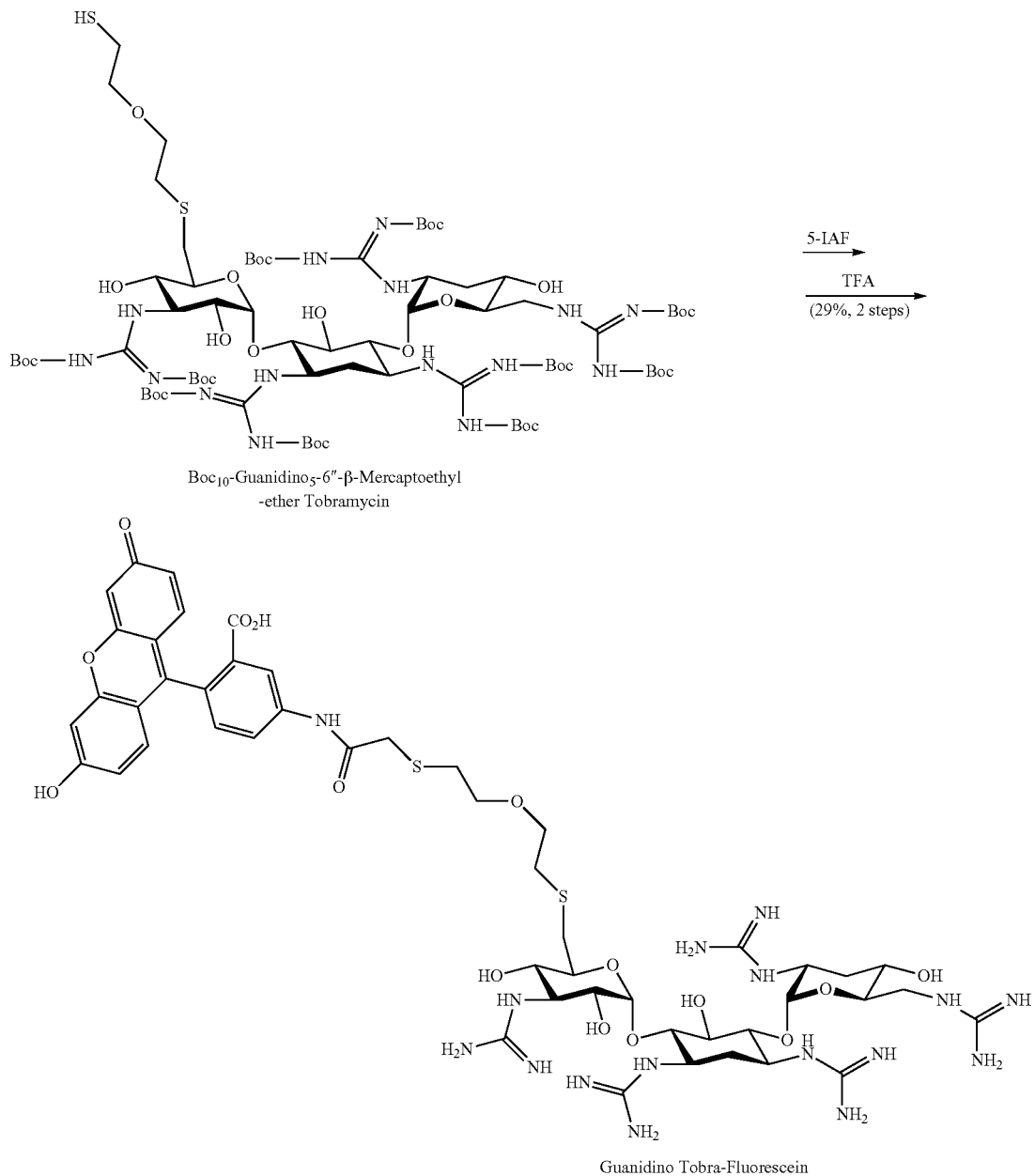

Boc$_{10}$-Guanidino$_5$-6''-β-Mercaptoethyl-ether Tobramycin

Guanidino Tobra-Fluorescein

Boc$_{10}$-guanidino$_5$-6''-β-mercaptoethylether tobramycin synthesized as described in Example 2 (10 mg, 5.6 μmoles), dimethylformamide (3 mL), Cs$_2$CO$_3$ (30 mg), and 5-iodo-acetamido-fluorescein (5-IAF) (5 mg, 9.7 mmoles, 1.7 equivalent, Molecular Probes) were stirred at room temperature in the dark for 2 hours, then diluted with ethyl acetate (150 mL) and twice washed with 1M Na$_2$CO$_3$ (50 mL each time), twice with 0.1M citric acid (50 mL each time), brine (50 mL), dried over sodium sulfate then concentrated under reduced pressure to a solid. The product was then deprotected using triisopropyl silane (0.15 mL) and trifluoroacetic acid (3 mL), in CHCl$_3$ (1 mL) for 2.5 hours at room temperature. Excess anhydrous toluene was then added and all volatile products were removed at 50° C. under reduced pressure. The product was then diluted with water (8 mL) and loaded onto an activated C-18 reversed-phase cartridge (Waters, Sep-pack), the column was then washed with pure water (10 mL), and the product eluted at 20% acetonitrile/water, lyophilized, and found to be >95% pure (by HLPC). The final product was purified further using a C-18 reversed phase HPLC column with an isocratic mixture of 20% acetonitrile (0.1% trifluoroacetic acid) in water (0.1% trifluoroacetic) (3 mL/min) (Rt=11.5 min) to yield 2.3 mg (29%, 2 steps) of an orange solid. All fluorescein-glycoside conjugates are slightly to moderately hygroscopic, therefore the absorption at 496 nm (in aqueous buffer having pH=9.0) was used to confirm the yield of the conjugation reaction (taking $\epsilon_{502\ nm}$=77,000 cm$^{-1}$M$^{-1}$). $^1$H-NMR (400 MHz, D$_2$O) 8.17 (d, J=2.0 Hz, 1H), 7.70 (d,d J$_1$=10 Hz, J$_2$=1.6 Hz, 1H), 7.15-7.20 (m, 3H), 6.97 (d, J=1.6 Hz, 2H), 6.79-6.80 (m, 2H), 5.19 (d, J=3.2 Hz, 1H), 4.91 (d, J=2.8 Hz, 1H), 3.95 (t, J=6.8 Hz, 1H), 3.20-3.60 (m, 23H), 2.80 (d,d J$_1$=11.2 Hz, $J_2$=2.4 Hz, 1H), 2.77 (t, J=5.8 Hz, 2H), δ 2.51-2.60 (m, 4H), δ 1.97-2.07 (m, $^2$H), 1.48-1.53 (m, 2H). MALDI TOF MS calculated for $C_{49}H_{68}N_{16}O_{15}S_2$: 1184.45 found 1185.63 [M+H]$^+$, found 1207.60 [M+Na]$^+$.

Example 9

Synthesis and Characterization of Guanidino-Neo-Fluorescein

A Scheme for synthesizing guanidino-neo-fluorescein is shown below (Scheme XIV):

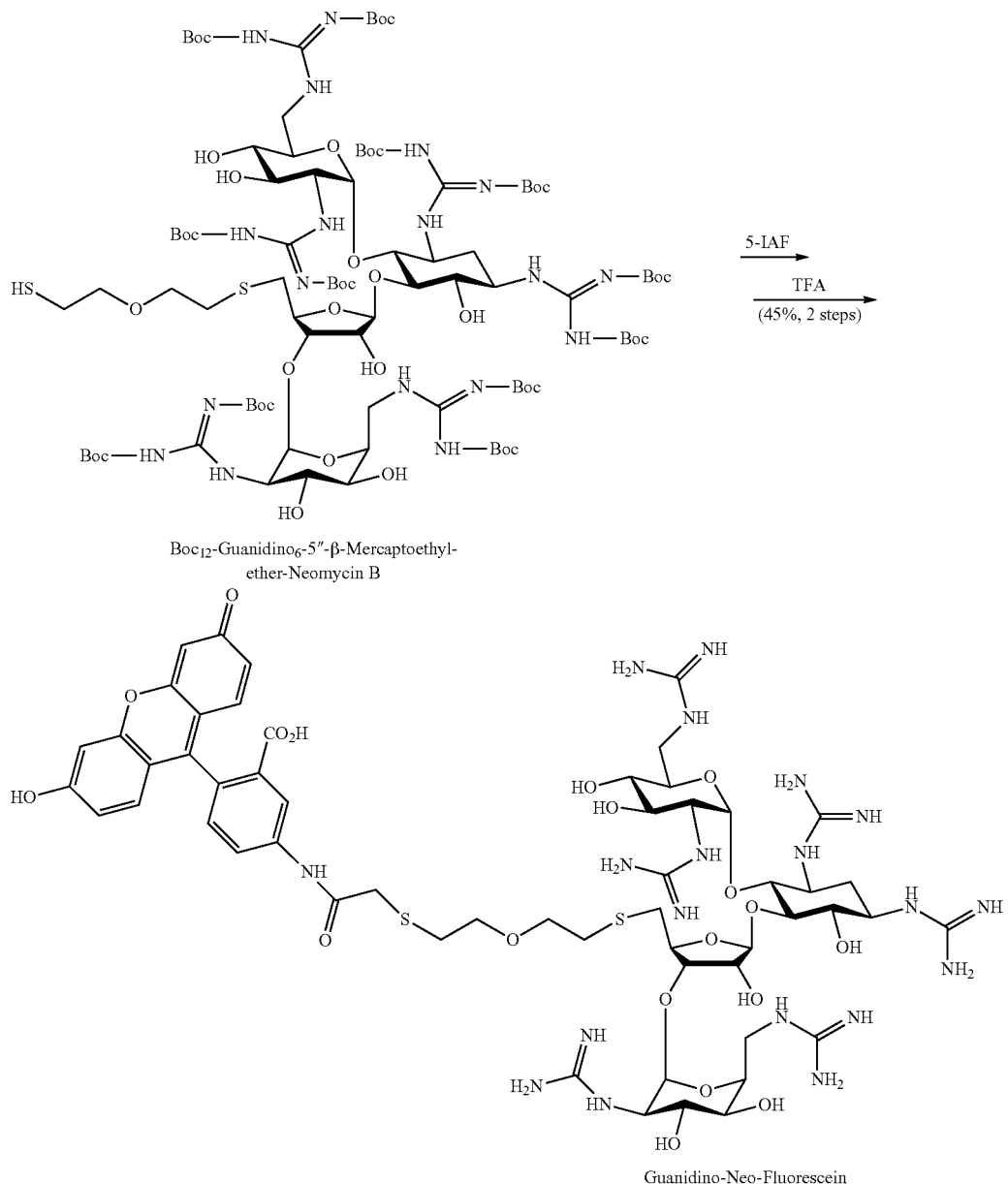

Boc$_{12}$-guanidino$_6$-5″-β-mercaptoethylether neomycin B prepared as described in Example 4 (3 mg, 1.4 μmoles), dimethylformamide (0.5 mL), 5-iodo-acetamido-fluorescein (5-IAF) (5 mg, 9.7 μmoles, 1.7 equivalent, Molecular Probes), and triethyl amine (20 μL) were stirred at room temperature in the dark for 2 hours, then diluted with ethyl acetate (150 mL) and washed four times with 1M $Na_2CO_3$ (50 mL each time), twice with 0.1M citric acid (50 mL each time), and brine (50 mL), dried over sodium sulfate then concentrated under reduced pressure to a solid. All of this product was then de-protected using triisopropyl silane (0.05 mL) and trifluoroacetic acid (5 mL), in $CHCl_3$ (3 mL) for 3.5 hours at room temperature. Excess anhydrous toluene was then added and all volatile products were removed at 50° C. under reduced pressure. The product was then diluted with water (8 mL, 300 mM NaCl) and loaded onto an activated C-18 reversed-phase cartridge (Waters, Sep-pack), the column was then washed with pure water (10 mL), and the product eluted between 5-20% acetonitrile/water (0.001M HCl), lyophilized, and found to be >85% pure (by HLPC).

The product was purified further using a C-18 reversed phase HPLC column with an isocratic mixture of 20% acetonitrile (0.1% trifluoroacetic acid) in water (0.1% trifluoroacetic acid) (3 mL/min) (Rt=9.3 min) to yield 1.3 mg (45%, 2 steps) of an orange solid. All fluorescein-glycoside conjugates are slightly to moderately hygroscopic, therefore the absorption at 496 nm (in aqueous buffer pH 9.0) was used to confirm the yield of the conjugation reaction (taking $\epsilon_{502\ nm}$=77,000 cm$^{-1}$M$^{-1}$). $^1$H-NMR (400 MHz, D$_2$O): 8.12 (d, J=2.0 Hz, 1H), 7.72 (d,d J$_1$=8.8 Hz, J$_2$=1.6 Hz, 1H), 7.22 (d, J=8.8 Hz, 1H), 7.11 (d, J=9.2 Hz, 2H), 6.92 (d, J=2.4 Hz, 2H), 6.76 (d,d J$_1$=8.8 Hz, J$_2$=2.4 Hz, 1H), 5.69 (d, J=4.0 Hz, 1H), 4.98 (s, 1H), 4.87 (s, 1H), 4.18-4.24 (m, 2H), 3.85-3.88 (m, 3H), 3.16-3.62 (m, 18H), 2.71-2.78 (m, 4H), 2.42-2.52 (m, 4H), 2.01 (d t, J$_1$=12.0 Hz, J$_2$=4.4 Hz, 1H), 1.48 (q, J=12.0 Hz, 1H). MALDI TOF MS calculated for C$_{55}$H$_{79}$N$_{19}$O$_{19}$S$_2$:1373.53, found 1374.72 [M+H]$^+$.

Example 10

Study of Cellular Uptake

10T1/2 cells, an adherent non-transformed mouse fibroblast cell line, and HeLa cells, a common human cancer cell line, were purchased from ATCC and used before their 20th passage. Both cell lines were cultured in Dulbecco's modified eagle medium containing 10% fetal bovine serum at 37° C. in an 8% CO$_2$ environment. For each experiment, cells were seeded onto 4 cm tissue culture plates (Nunc) and allowed to grow overnight to ~80% confluency.

Compounds 1-5 identified in Table 1, below (0.5-1 µM), were added to each dish and incubated at 37° C./8% CO$_2$ for 0.5-1 hr. Cells were then washed once in PBS, trypsinized with 500 µl ATV solution (Gibco) for 3 minutes, pelleted in a fixed angle centrifuge for 5 minutes at 5,000×G, then brought up in 1 mL PBS. Each sample was quickly (within 5 minutes) analyzed on a FACS VantageSE cell sorter (Becton-Dickinson) using the 488 nm argon/krypton laser line and a 530 nm band pass emission filter. 2,000-10,000 cells were counted per sample.

The uptake of BODIPY-containing glycosides by two different eukaryotic cell lines was also studied using fluorescence microscopy.

TABLE 1

Summary of the Mean Fluorescence Intensities of Treated Cells According to FACS[a]

| Compound | 10T1/2[b] | HeLa[c] |
| --- | --- | --- |
| None (auto-fluorescence) | ~40[d] | 830 |
| Tobra-BODIPY (1) | 60 | 1,000 |
| Guanidino-Tobra-BODIPY (2) | 240 | 2,100 |
| Neo-BODIPY (3) | 60 | ~1,400[e] |
| Guanidino-Neo-BODIPY (4) | 430 | 7,900 |
| BODIPY-Cys (Arg)$_9$ (5) | 280 | 2,000 |
| BODIPY-Cys(arg)$_9$ (5) + 10 µM (6) | 110 | n.d.[f] |
| BODIPY-Cys(arg)$_9$ (5) + 50 µM (6) | 90 | n.d. |
| BODIPY-Cys(arg)$_9$ (5) + 200 µM (6) | 70 | n.d. |

[a]The data between cell types are not directly comparable, as a higher instrumental gain (about 10-fold) was used for the HeLa experiments.
[b]Average intensity of 10,000 individual cells treated with 0.5 µM of each compound for 1 hr.
[c]Average intensity of 2,000 individual cells treated with 1 µM of each compound for 0.5 hr. Under these conditions a "free" BODIPY dye molecule Tris-BODIPY shows poor uptake into HeLa cells (similar to Tobra-BODIPY).
[d]Estimate based upon data set collected at a higher instrument gain.
[e]Estimate based upon data set collected at a lower instrument gain.
[f]n.d. = not determined.

Figure 3:
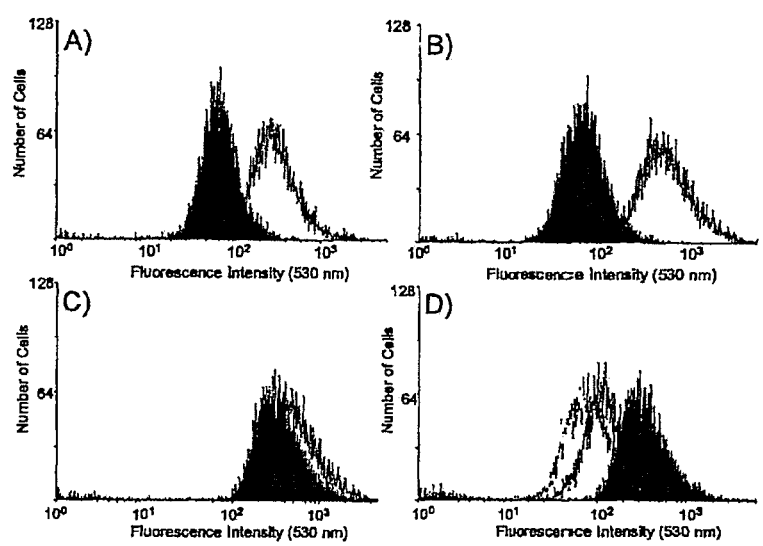
FIG. 3 presents FACS histograms showing the fluorescence intensity versus cell count.

Examples of FACS histograms are presented in FIG. 3, which illustrates the fluorescence intensity versus cell count for 10,000 individual 10T1/2 cells following a 1 hour incubation with 0.5 µM of: (A) tobra-BODIPY (Red) and guanidine-tobra-BODIPY (White); (B) neo-BODIPY (Red) and guanidine-neo-BODIPY (White); (C) BODIPY-Cys (Arg)$_9$ (Red), or guanidine-neo-BODIPY (White); and (D) uptake of BODIPY-Cys(Arg)$_9$ inhibited by guanidine-neomycin B (6) at 0 µM (Red), 10 µM (Black), 200 µM (Green).

Some microscopy images are shown in FIGS. 4, 6, 7 and 8. In a typical experiment, cell cultures were treated with 0.5-5 µM of each compound for 0.5-1 hr, washed twice with buffer, cleaved with trypsin, and quantified for fluorescence at 530 nm.

Figure 4:
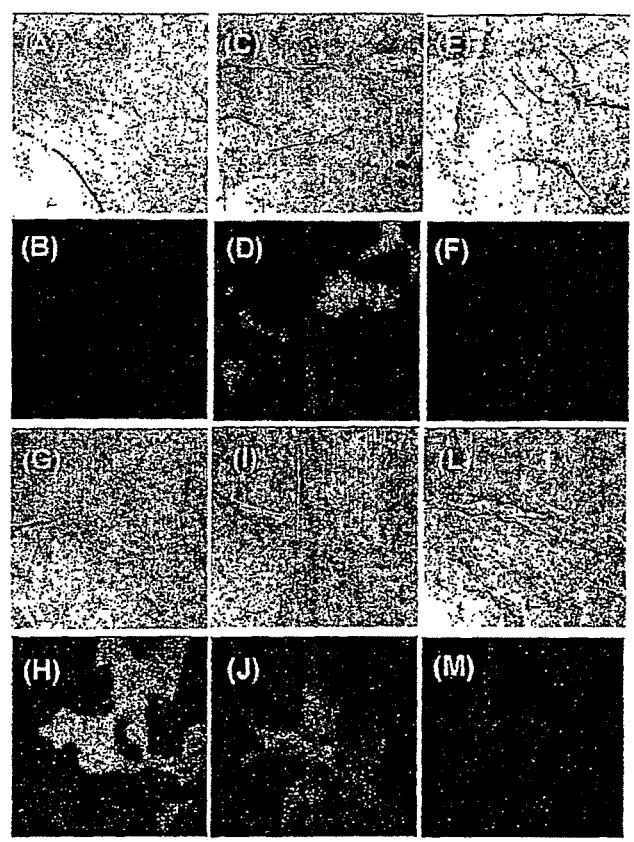
FIG. 4 illustrates cellular uptake of the fluorescein-labeled aminoglycosides and guanidinoglycosides into 10T1/2 cells that are adhered to culture plates.

FIG. 4 illustrates cellular uptake of the fluorescein-labeled aminoglycosides and guanidinoglycosides into 10T1/2 cells that are adhered to culture plates. For each sample, both fluorescence emission (B, D, F, H, J, M) and white light differential interference contrast (A, C, E, G, I, L) are shown. Each sample is treated with 1 µM of each compound for 1 hr, washed two times with buffer and imaged as described above. Shown are: amino tobra-mycinfluorescein (A and B), guanidine-tobra-fluorescein (C and D), amino-neo-BODIPY (E and F), guanidine-neo-fluorescein (G and H), fluorescein-CR$_9$ (I and J) and the control dye "βMe-fluorescein" (L and M).

Figure 6:
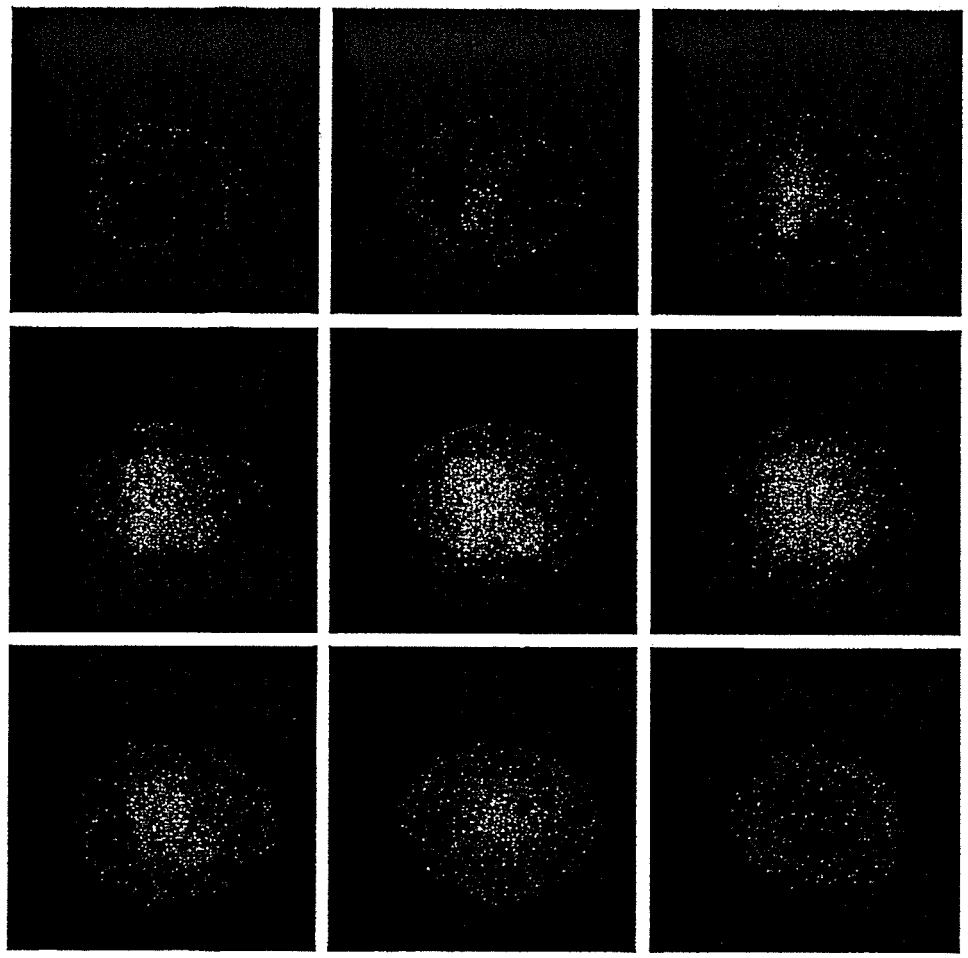
FIG. 6 shows an example of distribution type 1 (diffuse cytoplasmic, nuclear and nucleolar localization).

FIG. 6 shows an example of distribution type 1 (diffuse cytoplasmic, nuclear and nucleolar localization). 0.5 µm cross-sectional images of a single HeLa cell in solution are shown.

Figure 7:
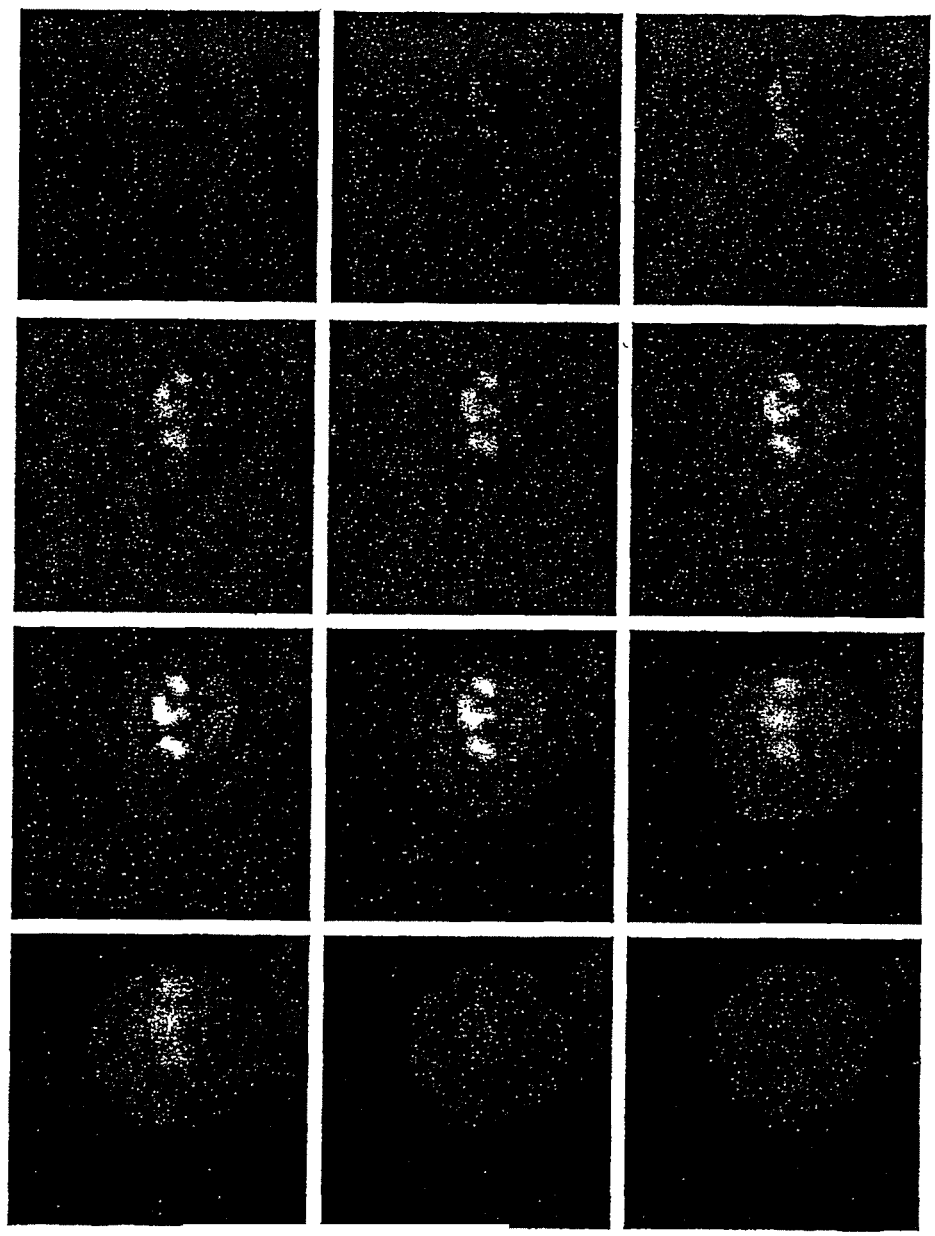
FIG. 7 shows an example of distribution type 2 (mainly nuclear and nucleolar localization).

FIG. 7 shows an example of distribution type 2 (mainly nuclear and nucleolar localization). 0.5 µm cross-sectional images of a single HeLa cell in solution are shown.

Figure 8:
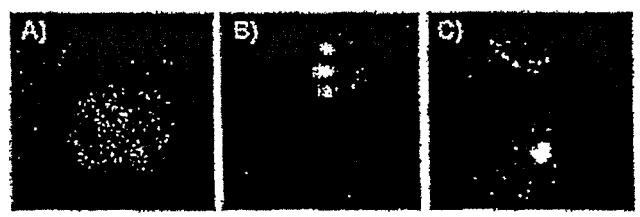
FIG. 8 shows microscopy experiments for fluorescein- and BODIPY-labeled guanidinoglycosides.
Figure 9:
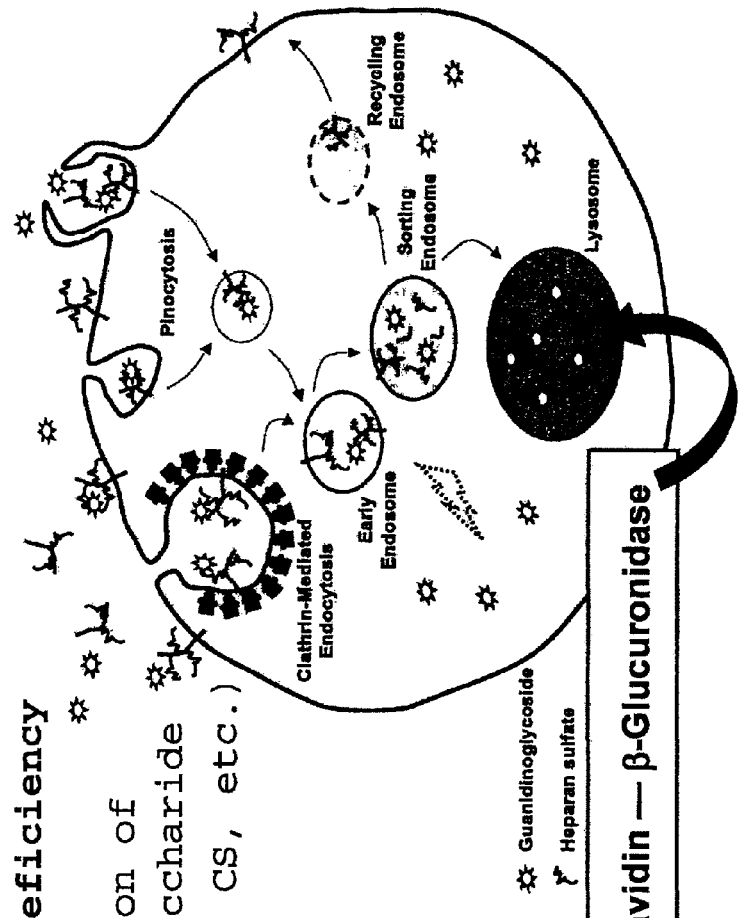
FIG. 9 shows an example of protein replacement therapy: β-glucuronidase deficiency in MPS (mucopolysaccharidoses) VII (Sly disease); HS (heparan sulfate), CS (chondroitin sulfate).
Figure 10:
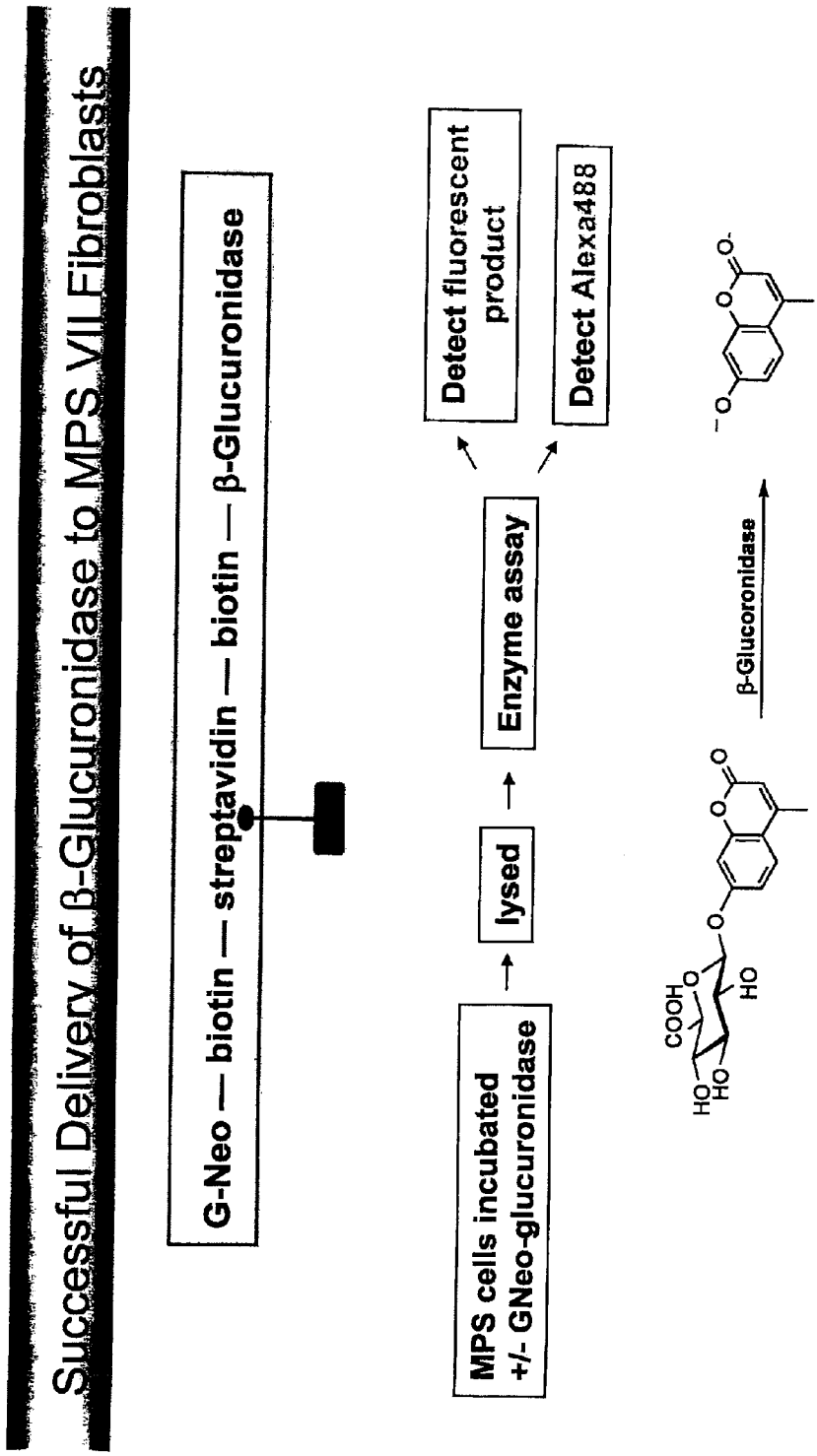
FIG. 10 shows any assay to measure successful delivery of β-glucuronidase to MPS VII fibroblasts.
Figure 11:
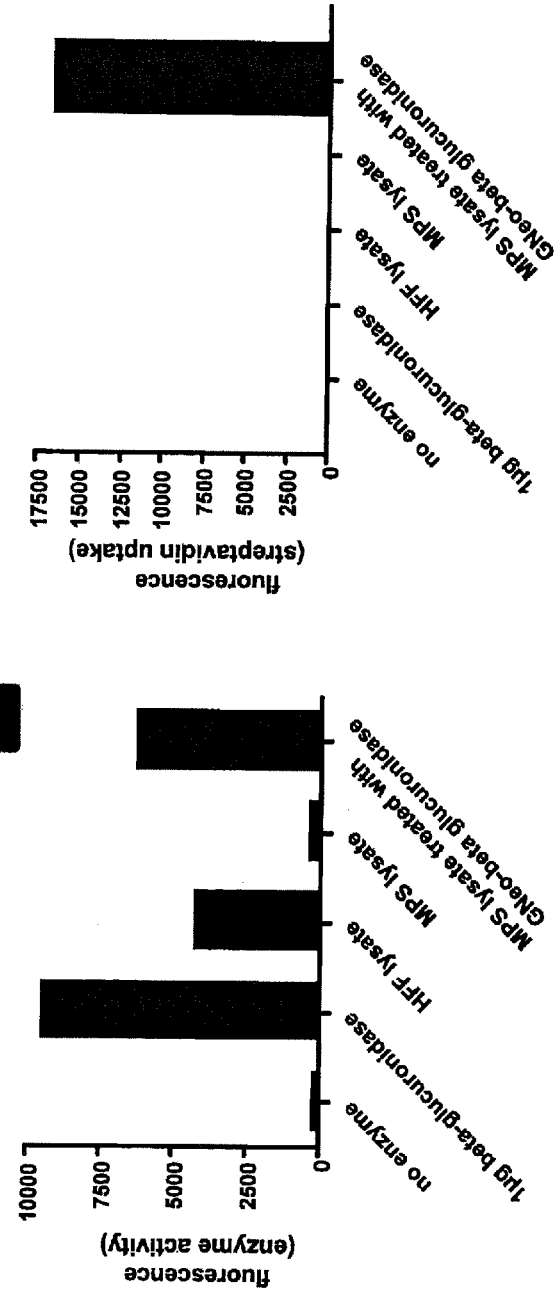
FIG. 11 shows the successful delivery of β-glucuronidase to MPS VII fibroblasts; HS (heparan sulfate), CS (chondroitin sulfate).

FIG. 8 shows microscopy experiments for fluorescein- and BODIPY-labeled guanidinoglycosides. (A) and (B) show cross-sectional images of two individual HeLa cells in solution following a 30 minute treatment with 5 µM of guanidine-neo-BODIPY and cleavage with trypsin. (C) shows two neighboring 10T1/2 cells growing on a culture plate following a 1 hr exposure to 1 µM of 4.

As can be seen, both fluorescent aminoglycosides (1 and 3, see FIG. 3) display poor cellular uptakes (slightly above the autofluorescence of the cell itself) (Table 1).

Upon guanidinylation, the cellular uptake of tobramycin is enhanced by approximately 10-fold (relative to autofluorescence), and the enhancement for neomycin B is approximately 20-fold (see, FIG. 3, (A) and (B) and Table 1). The type of molecular scaffold used for the display of guanidinium groups has a profound impact on the efficiency of uptake.

Compared to a common poly-Arg transduction peptide, the guanidinoglycosides show the same, or even better cellular uptake efficiencies. Guanidino-tobra-BODIPY (2 in Table 1) has 4 fewer guanidinium groups as BODIPY-Cys (Arg) (5 in Table 1), but shows approximately the same transport efficiency. Importantly, guanidine-neo-BODIPY (4 in Table 1) consistently has a better cellular uptake as compared to the poly-Arg peptide BODIPY-Cys(Arg) (5 in Table 1) (FIG. 3 (C), Table 1). This suggests that the semi-rigid pre-organization of the guanidinium groups on the glycoside core may better facilitate translocation across the cell membrane. In contrast to the results obtained for a family of poly-Arg peptoids, the flexible amphipathic properties usually provided by the methylene chains of poly(Arg) residues do not appear essential for membrane transport of guanidinoglycosides. To address the possibility that guanidine-neomycin B enters cells through a different mechanism than poly-Arg, a competition experiment was conducted between BODIPY-Cys(Arg) (5 in Table 1 and the unlabeled guanidine-neomycin B (6, see FIG. 2). FACS analysis shows that guanidine-neomycin B (6, see FIG. 2) effectively inhibits the transport of BODIPY-Cys(Arg) into cells (FIG. 3 (D) and Table 1), suggesting a common pathway responsible for the uptake of both compounds.

Microscopy experiments have been conducted using both fluorescein-labeled and BODIPY-labeled guanidinoglycosides. The relative intensities of individual cells, following treatment with either fluorescent aminoglycosides or guanidinoglycosides are consistent with the trends from FACS experiments. Optical cross sectioning using scanning confocal fluorescence microscopy indicates that guanidinoglycosides are found inside of living cells (FIG. 8). Interestingly, two distinct types of cellular localization of guanidino-neo-BODIPY are observed (FIG. 8). Approximately half of the cells exhibit a highly diffuse, cytoplasmic and nuclear distribution (FIG. 6), while the other half exhibit more localized nucleolar staining, similar to that reported for poly-Arg peptides (FIG. 7). Similar results were observed with fluorescein-labeled conjugates, as well as 10T½ cells (FIG. 8). Taken together, this suggests that the relative uptake efficiencies and cellular localization of these compounds are not highly dependent on cell type or dye molecules used.

In summary, unlike aminoglycosides, guanidinoglycosides exhibit highly efficient uptake by eukaryotic cell cultures via a similar mechanism as a poly-arginine peptide.

Example 11

Evaluation of HIV-1 Inhibitory Activity

The analytically pure and fully characterized conjugates will be tested for their ability to inhibit HIV replication in HIV-1 infected CD44 HeLa cells by following their inhibition of plaque formation. The decrease in viral load in infected human peripheral blood monocytes (determined by standard p24 ELISA) will also be carried.

The performance of the AZT-guanidino-neomycin B conjugate, for example, can be evaluated against the individual components. These controls include: 1) AZT alone, 2) linker alone, 3) guanidino-neomycin B alone, 4) AZT+ guanidino-neomycin B, 5) AZT-monophosphate alone, and 6) AZT-monophosphate+ guanidine-neomycin B. In each case dose-dependent curves will be generated in triplicates.

Example 12

Guanidinylated Neomycin Delivers Large, Bioactive Cargo into Cells through a Heparin Sulfate-dependent Pathway The Journal of Biological Chemistry article by Elson-Schwab, Lev et al., titled "Guanidinylated Neomycin Delivers Large, Bioactive Cargo into Cells through a Heparin Sulfate-dependent Pathway" (May 4, 2007, Vol. 282, No. 18, pp 13585-13591) is hereby incorporated by reference in its entirety for all purposes. The figure and table references below refer to the above-referenced paper.

Facilitating the uptake of molecules into living cells is of substantial interest for basic research and drug delivery applications. Arginine-rich peptides have been shown to facilitate uptake of high molecular mass cargos into cells, but the mechanism of uptake is complex and may involve multiple receptors. In this report, we show that a derivative of the aminoglycoside antibiotic neomycin, in which all of the ammonium groups have been converted into guanidinium groups, can carry large (>300 kDa) bioactive molecules across cell membranes. Delivery occurs at nanomolar transporter concentrations and under these conditions depends entirely on cell surface heparan sulfate proteoglycans. Conjugation of guanidinoneomycin to the plant toxin saporin, a ribosome-inactivating agent, results in proteoglycan-dependent cell toxicity. In contrast, an arginine-rich peptide shows both heparan sulfate-dependent and -independent cellular uptake. The high selectivity of guanidinoneomycin for heparan sulfate suggests the possibility of exploiting differences in proteoglycan compositions to target delivery to different cell types.

Advances in genomics and proteomics have identified high molecular mass biomolecules and their analogs as potential therapeutic agents. The ability of a cell to take up a high molecular mass drug and to release it into the cytoplasm in an active form represents, however, a major obstacle for the development of these agents. For biological macromolecules effective delivery entails minimal exposure to conditions that may denature or otherwise disrupt activity. Numerous approaches for the physical control of drug localization and release significantly improve the pharmacokinetic features of bioactive molecules, but they typically do not address the inherent challenge of transport of the therapeutic agent across cell membranes. Delivery procedures based on passive diffusion encounter problems due to charged groups, and carriers that exploit endogenous membrane transporters limit the size of potential drug candidates.

Certain polybasic proteins have been shown to enhance the cellular uptake of biomolecules (1). Over the past 15 years, tremendous progress has been made in advancing the basic science, applications, and preclinical evaluation of these and other cationic cell transduction domains (2, 3). In 1988, the human immunodeficiency virus 1 Tat protein was shown to cross lipid bilayers and enter the nucleus (4, 5). Subsequently, numerous other naturally occurring and chimeric peptides have been found to exhibit efficient translocation properties. A data base search, inspired by Tat, identified a number of membrane-permeable peptides that contain clustered arginine residues (6,7). Further exploration of stereochemistry and composition identified D-Tat and $Arg_9$ as competent transporters (6, 7). Additionally, significant activity was observed for branched arginine-rich oligomers (8). These observations suggested that the presence of guanidinium moieties represents the critical feature responsible for efficient cell membrane permeability. In fact, guanidinium-containing peptoids (9) and β-peptides exhibit useful cell uptake properties (10). Short polyproline-based helices appended with guanidinium groups (11), highly branched guanidinium-rich dendritic oligomers (12), and heterocyclic guanidinium vectors also serve as cell transporters (13).

The mechanistic understanding of the cellular uptake and internalization of arginine-rich peptides and their analogs has yet to be fully elucidated. Endocytosis-based mechanisms have been both supported and questioned, but some of the early studies may have suffered from artifacts generated by cell fixation. Electrostatic interactions of the positively charged peptides with membrane phospholipids have been proposed as the first step in the transduction process (14-17). An alternative model that has recently been gaining support is the interaction of the positively charged peptides with negatively charged cell surface proteoglycan receptors (18-20).

Recently, we described a new family of synthetic RNA ligands, coined "guanidinoglycosides" (FIG. 1), in which the amino groups of naturally occurring aminoglycoside antibiotics were converted to guanidinium groups. These compounds exhibit high affinity and selectivity for RNA targets that are naturally recognized by Arg-rich domains (21). Guanidinoglycosides also display cellular uptake properties (22). Here, we explore the cellular requirement for uptake, as well as the delivery potential of guanidinoglycosides. We demonstrate that (i) the cellular binding and uptake of guanidinoneomycin at low concentration depends exclusively on heparan sulfate; (ii) in contrast, the uptake of arginine-rich peptides in the same concentration range follows both heparan sulfate-dependent and -independent pathways; (iii) guanidinoneomycin will transport high molecular mass and bioactive cargo into cells at low concentration in a completely proteoglycan-dependent manner; and (iv) effective guanidinoneomycin-mediated delivery can be achieved with little or no cellular toxicity.

Cell Culture—Chinese hamster ovary cells (CHO-K1)[3] (ATCC CCL-61) and Lec 2 (ATCC CRL-1736) were obtained from the American Type Culture Collection (Rockville, Md.). Mutants pgsA745 and pgsG224 were described previously (23, 24). All cell lines were grown under an atmosphere of 5% $CO_2$ in air and 100% relative humidity in F12 growth medium supplemented with 7.5% (v/v) fetal bovine serum, 100 μg/ml of streptomycin sulfate, and 100 units/ml of penicillin G.

Synthesis of Guanidinoneomycin-Biotin, Neomycin-Biotin, and $Arg_9$-Biotin—Synthesis of guanidinoneomycin-biotin and neomycin-biotin is described in the supporting information. $Arg_9$-biotin and $Arg_9$-BODIPY were synthesized using standard Fmoc (N-(9-fluorenyl)methoxycarbonyl)/HBTU (O-(1H-benzotriazole-1-yl)-N,N,N',N'--tetramethyluronium hexafluorophosphate) chemistry as described in the supporting information.

Inhibition Experiments—Wild-type CHO cells were grown to confluence on 6-well tissue culture plates, harvested with 10 mM EDTA (37° C., 10 min), washed with phosphate-buffered saline (PBS), and incubated in suspension with biotinylated FGF-2 (10 ng/ml) (25) in F12 medium for 1 h at 4° C. in the presence of increasing concentrations of guanidinoneomycin (100 nM to 1.8 mM). The cells were then stained with streptavidin-phycoerythrin-Cy5 (BD Biosciences) for 20 min, washed three times with PBS, and analyzed by flow cytometry. Cells were also incubated in F12 medium containing 0.5 μM $Arg_9$-BODIPY and increasing concentrations of guanidinoneomycin (1-300 μM) for 1 h at 37° C. and analyzed by flow cytometry.

Preparation of Fluorescently Tagged Guanidinoneomycin-Biotin, Neomycin-Biotin, and $Arg_9$-Biotin and Cell Uptake Studies—Biotinylated compounds were stored in water at −20° C. After thawing at room temperature, compounds were diluted into F12 medium to 1 μM. To this solution, streptavidin-PE-Cy5 (BD Biosciences) was added in a 1:1000 dilution to achieve a ratio of 1:3 of fluorophore to biotin. To ensure completion of the biotin-streptavidin reaction, the solution was gently mixed and allowed to incubate at room temperature, shielded from light for 30 min. Following this incubation, compounds were diluted to the desired concentration in growth medium. For experiments done at 4° C. solutions were incubated on ice for 30 min.

Wild-type and mutant CHO cells were grown to confluency on 6-well tissue culture plates. After washing with PBS, cells were incubated with the fluorescent-tagged guanidinoneomycin-, neomycin-, or $Arg_9$-biotin for 1 h at 37° C. under an atmosphere of 5% $CO_2$. Cells were washed with PBS, released with EDTA, and analyzed by flow cytometry.

Microscopy—Cells were cultured on Lab-Tek chambered coverglass slides (Electron Microscopy Sciences) in F12 medium. After washing with PBS, cells were incubated for 1 h in 1 ml of 60 nM guanidinoneomycin coupled to streptavidin-Alexa-488 (Molecular Probes) at 37° C. Guanidinoneomycin-A488 was prepared by incubating 1 μM guanidinoneomycinbiotin with 6 μg of streptavidin-Alexa-488 in 1 ml of medium. Hoechst 33342 (2 μg/ml; Molecular Probes) was added to cells for the last 20 min of incubation. Cells were washed three times with F12 medium before live cell imaging. Microscopic images were acquired on an Olympus IX70 DeltaVision Spectris Image Deconvolution system, equipped with a temperature and atmospherically controlled stage. Images were deconvolved (10 cycles) using SoftWoRx Explorer Suite software.

Saporin Delivery—A conjugate of saporin and biotinylated guanidinoneomycin was prepared by mixing streptavidinylated saporin (Advanced Targeting Systems) with biotinylated compound in 1:4 ratio. Wild-type CHO and pgsA cells were incubated with guanidinoneomycin-biotin, guanidinoneomycin-biotin and saporin or the conjugate of guanidinoneomycin-biotin and streptavidinylated saporin in complete growth medium for 4 days at 37° C. CellTiter-Blue (Promega) was added to the medium and cells were incubated for an additional 4 h to measure viability.

Uptake of Guanidinoneomycin Depends on Heparan Sulfate—Neomycin is a member of a family of aminoglycoside antibiotics that inhibit protein synthesis in bacteria (26). Conversion of the amino groups to guanidinium groups alters the properties of the glycoside, allowing it to interact with cell surface heparan sulfate. To study its interactions with cells, we synthesized biotinylated guanidinoneomycin, as well as biotinylated neomycin and biotinylated $Arg_9$ for comparison (FIG. 1). Biotinylation facilitates conjugation of the carriers to fluorophores and its versatility allows for the preparation and testing of a variety of analogs in different assays.

Fluorescent streptavidin-phycoerythrin-cychrome (streptavidin-PE-Cy5) conjugates of biotinylated guanidinoneomycin, neomycin, and $Arg_9$ were incubated with CHO cells and uptake was measured by flow cytometry. As described below, these measurements reflect both binding and internalization of the conjugates but are referred to as "uptake" for the sake of clarity. Uptake of the fluorescent guanidinoneomycin conjugate occurred at concentrations as low as 10 nM and proportionately increased up to a concentration of 1 μM, the highest concentration tested (FIG. 2, upper panels, blue lines). Cells also took up the neomycin conjugate but much less efficiently than the guanidinylated derivative (middle panel, blue lines). Uptake of the $Arg_9$ peptide occurred in a more complex manner, exhibiting two classes of receptors expressed by different cells in the population (lower panel, blue lines).

Incubation with heparin at concentrations as low as 100 ng/ml blocked uptake of the fluorescent guanidinoneomycin conjugate (FIG. 3), suggesting a high affinity of the compound for the negatively charged residues in heparin. These data also suggested the possibility that cell surface heparan sulfate proteoglycans might represent one class of receptors that mediate binding and uptake. To test this idea, the fluorescent guanidinoneomycin conjugate was incubated with pgsA cells, a mutant that makes <2% of the wild-type level of chondroitin sulfate and heparan sulfate chains (Table 1) (23). Guanidinoneomycin uptake in pgsA cells was barely detectable up to concentrations of 100 nM and was over 20-fold lower than that observed with wild-type cells, even at 1 μM (FIG. 2, upper panels, green lines). At higher concentrations, a second, glycosaminoglycan-independent mode of uptake began to emerge. The same trend was observed for the fluorescently tagged neomycin, with internalization being more efficient in wild-type cells than pgsA cells (FIG. 2, middle panels, green lines). The signal from pgsA cells was not affected by trypsin, indicating interactions with a non-proteinaceous receptor.

Whereas the uptake of guanidinoneomycin was strongly dependent on cell surface glycosaminoglycans, fluorescently labeled $Arg_9$ exhibited multiple modes of uptake in pgsA cells even at low concentrations (FIG. 2, lower panels, green lines). Multiple populations of cells exhibiting differential binding or uptake capacity were observed in pgsA cells and in wild-type cells. These data suggest that the internalization of $Arg_9$ follows both glycosaminoglycan-dependent and -independent pathways. Analysis of the mean fluorescence values showed that uptake of the compounds occurred in proportion to concentration, but did not saturate (FIG. 2b). Because of this, no further experiments to measure affinity were attempted.

To further study the uptake of guanidinoglycosides, other mutant CHO cells were examined (Table 1, FIG. 3). pgsG cells, mutants lacking all glycosaminoglycans due to a deficiency in glucuronyltransferase I (24), showed a reduction in binding and uptake similar to pgsA cells. Reintroduction of the gene for glucuronosyltransferase I (pgsG+ GlcATI) restored binding and uptake, demonstrating their dependence on glycosaminoglycans. Cells selectively lacking heparan sulfate (pgsD) 27) also exhibited dramatically reduced binding and uptake of fluorescent guanidinoneomycin. Because pgsD cells express higher than normal levels of chondroitin sulfate on the cell surface, these findings demonstrate the specificity of binding and uptake for heparan sulfate. Examination of Lec2 cells, which lack sialic acid residues, excluded participation of sialylated glycoproteins and glycolipids (data not shown).

To test the dependence of guanidinoglycoside uptake on heparan sulfate in other cells, we incubated human HeLa ovarian carcinoma cells with fluorescent guanidinoneomycin. A robust signal was obtained, and treatment of the cells with heparin lyases reduced uptake (FIG. 3). The extent of reduction was not as great by enzymatic treatment as by genetic inactivation of heparan sulfate formation in CHO cells, presumably due to incomplete digestion of heparan sulfate chains. Similar results were also obtained for STO mouse fibroblast cells (data not shown), indicating that heparan sulfate on other cells can also mediate uptake of guanidinoneomycin.

To distinguish between cell surface binding and internalization, wild-type CHO cells were incubated with the fluorescent guanidinoneomycin conjugate at 4° C., where only surface binding occurs. The extent of labeling at 4° C. was reduced by ~6-fold compared with incubations performed at 37° C. (FIG. 4, inset), suggesting that ~85% of the fluorescence signal at 37° C. was due to internalization. Binding at 4° C. was sensitive to trypsin and heparinase treatment, consistent with binding to membrane proteoglycans. Incubation of pgsA cells showed that at low concentrations binding was entirely dependent on expression of glycosaminoglycans. At higher concentrations, a second class of binding sites was detected that did not show saturability (FIG. 4). Binding to wild-type cells at higher concentrations represents the sum of both classes of binding sites. Subtraction of the fluorescent values obtained from the mutant (pink line) from those obtained from the wild-type (blue line) yielded a binding curve (green line) that presumably reflects the contribution of the proteoglycans (FIG. 4).

Guanidinoneomycin Inhibition of FGF-2 and $Arg_9$ Binding to Cell Surface Heparan Sulfate—The binding and uptake studies described above predicted that guanidinoneomycin would inhibit binding of ligands that are known to interact with heparan sulfate, such as basic fibroblast growth factor (FGF-2) (29, 30). Prior studies have shown that biotinylated FGF-2 will bind to wild-type CHO cells in a heparan sulfate-dependent manner (24). When mixed with increasing concentrations of guanidinoneomycin, binding was inhibited, with an $IC_{50}$ value of ~20 μM (FIG. 5a). In contrast, neomycin, the parent aminoglycoside, did not inhibit binding of FGF-2, which is consistent with its reduced affinity for heparan sulfate (data not shown). Guanidinoneomycin also blocked fluorescent-$Arg_9$ binding and uptake (FIG. 5h). However, inhibition of $Arg_9$ was incomplete, saturating at the same level of fluorescence intensity as observed when fluorescent $Arg_9$ was incubated with pgsA cells (FIG. 5h, inset). These data show that $Arg_9$ and guanidinoneomycin bind to a common set of glycosaminoglycan-dependent sites and support the idea that $Arg_9$ also has one or more glycosaminoglycan-independent mechanisms of uptake.

Guanidinoneomycin Internalization and Cytoplasmic Delivery of Cargo—To study uptake of guanidinoneomycin in live cells, wild-type and glycosaminoglycan-deficient pgsA cells were incubated with a conjugate prepared from guanidinoneomycin-biotin and streptavidin-Alexa-488. Deconvolution fluorescence microscopy demonstrated uptake into punctate vesicles (FIG. 6a), whereas uptake was not observed in pgsA cells (FIG. 6b). Inclusion of heparin (50 μg/ml) in the incubation medium completely abolished uptake in wild-type cells (data not shown), but washing the cells with heparin (350 μg/ml) after incubation with the fluorescent guanidinoglycoside conjugate had little effect on vesicle fluorescence, consistent with the idea that the punctate structures were intracellular. With longer incubation, more diffuse cytoplasmic staining was observed as well (data not shown).

To probe the mechanism of uptake, wild-type cells were incubated with the fluorescent guanidinoneomycin conjugate in the presence of sucrose, which has been shown to inhibit clathrin-mediated endocytosis through dissociation of the clathrin lattice (31), and amiloride, which specifically blocks macropinocytosis through inhibition of $Na^+/H^+$ exchange (23, 32). Cells treated with sucrose showed a marked decrease in internalization of guanidinoneomycin, whereas amiloride had no effect (FIG. 6c). These data indicate that guanidinoneomycin is likely internalized into cells via clathrin-dependent endocytosis, consistent with other studies indicating that proteoglycans undergo constitutive internalization (33).

These findings suggested that much of the internalized fluorescent guanidinoneomycin was present in endocytic vesicles or lysosomes but with time some will appear in the cytoplasm. To examine whether guanidinoneomycin could deliver large cargo into the cytoplasm, streptavidinylated saporin was conjugated to guanidinoneomycin-biotin. Saporin, a Type I ribosome-inactivating toxin from *Saponaria officinalis* seeds, does not kill cells due to lack of cell surface receptors (34). However, conjugation of saporin to a ligand for which receptors exist leads to cell death (34). As shown in FIG. 7, the guanidinoneomycin-saporin complex killed wild-type CHO cells with an $LD_{50}$ of ~2 nM. No cell toxicity was observed for unconjugated guanidinoneomycin-biotin or for free saporin at concentrations up to 100 nM. Mutant pgsA cells were resistant to toxin within this range of concentration but succumbed at higher concentrations, similarly to cells treated with neomycin-saporin or unconjugated saporin at high concentration. Taken together, these data show that guanidinoneomycin can deliver at very low concentrations large, bioactive cargo into the cytoplasm in a heparan sulfate-dependent manner.

Cationic transduction domains, such as the Arg-rich Tat peptide, have been demonstrated to effectively cross lipid bilayers and enter cells (7). Importantly, such relatively short peptides have also been shown to facilitate the uptake of diverse molecular cargos, from small molecules to oligonucleotides and proteins. These observations support the notion that such molecular transporting vehicles can eventually be used to facilitate cellular delivery of impermeable therapeutic agents. A natural peptidic backbone (or sequence) is unnecessary for delivery, because several guanidinium-containing derivatives have been shown to function in a similar manner to Arg-rich peptides. Here, we have evaluated the cell surface requirements for the uptake of guanidinoneomycin, a carbohydrate-based, nonoligomeric guanidinium-rich derivative of the naturally occurring aminoglycoside antibiotic. Like their oligo-arginine counterparts, guanidinoneomycin can deliver high molecular mass cargos, but with much greater selectivity for cell surface heparan sulfate. Thus, guanidinylated glycosides such as guanidinoneomycin may provide the opportunity to develop cell-selective delivery tools, exploiting the differences in proteoglycan expression among different cell types (35).

A universal feature of cell transduction domains, independent of backbone structure, is the presence of a number of guanidinium groups. Bearing a fixed positive charge, these groups can readily form charge-charge interactions with negatively charged groups present in macromolecules, such as phosphate groups in nucleic acids, sulfate and carboxyl groups in glycosaminoglycans, and polar head groups of acidic phospholipids enriched in the outer leaflet of the plasma membrane. The guanidinoglycosides bind more avidly than the corresponding aminoglycosides, presumably due to the higher basicity of the guanidinium groups and their ability to form charged, paired hydrogen bonds with sulfate groups. Apparently, net charge plays a key role in efficacy, as cell transduction domains typically contain between 5 and 11 clustered guanidino groups (3, 9, 22). The studies reported here also demonstrate that the three-dimensional distribution and density of guanidinium groups confer preferred interactions. Thus, exogenously supplied guanidinoneomycin preferentially interacts with heparan sulfate chains associated with cell surface proteoglycans, and not with other acidic glycans, such as chondroitin sulfate, which actually has a higher average charge density per unit length compared with heparan sulfate. Guanidinoneomycin can also bind to a second class of lower affinity receptors when added at higher concentrations. While the proteoglycan-dependent receptors became saturated at low micromolar concentrations of guanidinoneomycin, the binding to this second, non-heparansulfate-dependent class of receptors did not plateau. This finding indicates that these receptors are abundant and may constitute a major part of the cell surface, such as the polar heads of the phospholipids (15). The ability to alter the number and spatial distribution of guanidinium groups on glycoside-based scaffolds may aid in the design of even more specific derivatives.

A major finding reported here is the use of guanidinoglycosides to facilitate the cytoplasmic delivery of bioactive cargo, such as streptavidinylated saporin (~130 kDa) and phycoerythrin (~300 kDa). The use of saporin as a probe of cytoplasmic delivery has several advantages, including greater sensitivity and the capacity to kill cells by inhibition of protein synthesis. The dependence of cytoplasmic delivery on heparan sulfate and its sensitivity to sucrose suggests that the guanidinoneomycin conjugates may bind to membrane proteoglycans and "piggy-back" into the cell during clathrin-dependent endocytosis. A portion of membrane proteoglycans undergoes constitutive internalization and degradation in lysosomes (33). Although it is tempting to speculate that the punctate structures labeled by fluorescent guanidinoneomycin represent a pool from which saporin complexes escape or are transported into the cytosol, further studies are needed to determine the actual compartment from which cytosolic cargo originates.

Guanidinoglycosides present several advantages over peptide/oligomer-based transport vehicles: 1) The mechanism of uptake and delivery of polyarginine appears to be more complicated, because both heparan sulfate-dependent and -independent pathways exist; 2) Non-peptidic and non-oligomeric structures may display enhanced in vivo stability; 3) Aminoglycoside-degrading enzymes, and by inference enzymes that degrade guanidinoglycosides, have not yet been described in animal cells, whereas multiple proteases exist that can degrade arginine-rich peptides; 4) Guanidinoglycosides may offer greater flexibility in conjugation chemistry as compared with peptide-based delivery agents; 5) The chemical synthesis of guanidinoglycosides allows for divergent synthesis of multiple conjugates; and 6) The use of cleavable linkers might further facilitate the delivery of small and large molecules and their release within the cytoplasm.

In summary, we have shown the capacity of guanidinoglycosides to deliver high molecular mass, bioactive cargos into cells. At low concentration, cellular uptake occurs exclusively by heparan sulfate-dependent receptors. This behavior may provide a window of opportunity to exploit differences in expression of cell surface proteoglycans for the development of more effective and selective cellular delivery vehicles.

TABLE 1 Glycan-deficient cell lines CHO, Chinese hamster ovary cells.

FIG. 1. Molecules utilized. a, guanidinoneomycin. b, a hexasaccharide fragment of heparan sulfate. Interactions between the negatively charged sulfate groups on the heparan sulfate chain and positively charged guanidinium groups on the guanidinoglycoside are likely key for recognition. c, biotinylated guanidinoneomycin and biotinylated neomycin. d, biotinylated $Arg_9$. Details for the synthesis of the biotinylated derivates can be found in the supplemental materials.

FIG. 2. Uptake of fluorescent carriers in CHO cells. a, biotinylated guanidinoneomycin (G-Neo), biotinylated neomycin (Neo), and biotinylated $Arg_9$ ($Arg_9$) were conjugated to streptavidin-PE-Cy5 (~300 kDa). Wild-type (blue) and heparan/chondroitin sulfate-deficient pgsA cells (green) were incubated with the different conjugates at concentrations from 10 to 1000 nM for 1 h at 37° C. After washing the cells, they were released with EDTA and analyzed by flow cytometry. Cells incubated with streptavidin-PE-Cy5 alone are shown in red. b, mean fluorescence values show that both guanidinoneomycin and neomycin display glycosaminoglycan-dependent uptake; however, guanidinoneomycin has a considerably higher uptake efficiency than neomycin. The uptake of $Arg_9$ does not appear to depend exclusively on heparan/chondroitin sulfate glycosaminoglycans.

FIG. 3. Binding and uptake of guanidinoneomycin by CHO cells and mutants. Guanidinoneomycin-biotin streptavidin-PE-Cy5 conjugates were incubated with wild-type and mutant CHO cells at 60 nM for 1 h at 37° C. under the indicated conditions. Binding and uptake was analyzed by flow cytometry, and the mean fluorescence values were determined These data show that the cellular uptake of guanidinoneomycin depends on the presence of cell surface heparan sulfate.

FIG. 4. CHO cell binding of guanidinoneomycin at 4° C. Guanidinoneomycin-biotin streptavidin-PE-Cy5 conjugates were incubated with wild-type (blue) and pgsA (pink) cells at concentrations from 10 nM to 30 μM at 4° C. Binding was analyzed by flow cytometry, and the mean fluorescence values were determined. The difference between mean values (green) shows that proteoglycan-dependent binding sites for guanidinoneomycin start to become saturated at low to mid micromolar concentrations. The inset shows relative mean fluorescence values for untreated wild-type cells and wild-type cells treated with guanidinoneomycin at 37 and 4° C.

Figure 5:
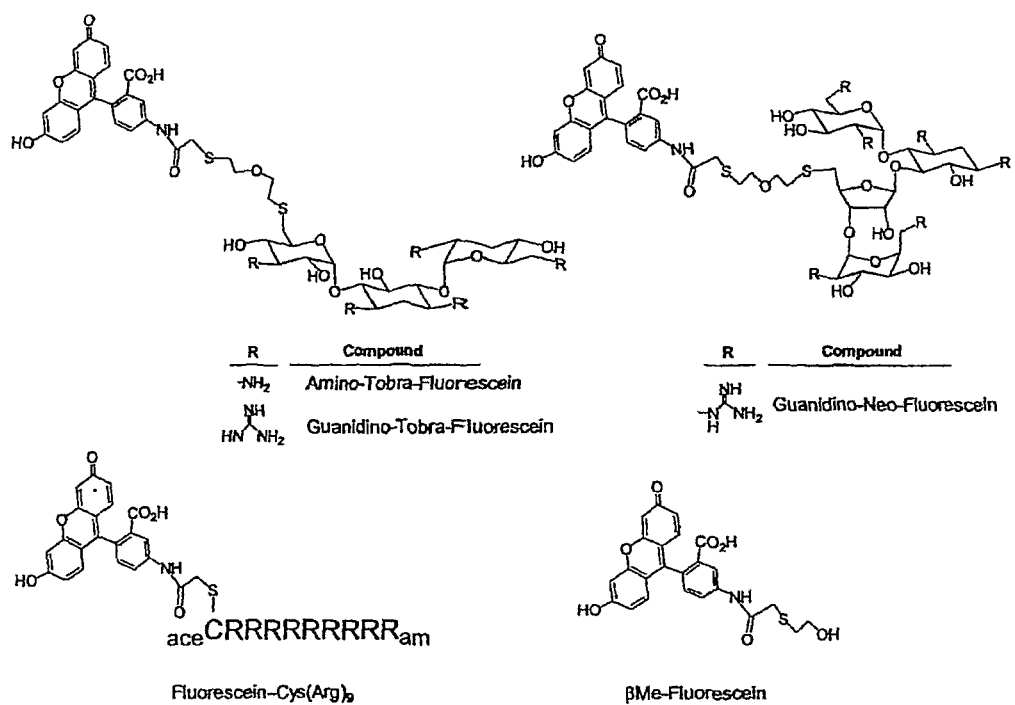
FIG. 5 illustrates structures of fluorescein-containing compounds.

FIG. 5. Inhibition of FGF and $Arg_9$ binding by guanidinoneomycin. a, wild-type CHO cells were incubated with biotinylated FGF-2 (10 ng/ml) for 1 h in the presence of increasing concentrations of guanidinoneomycin. Cells were then stained with streptavidin-phycoerythrin-cychrome and analyzed by flow cytometry. Guanidinoneomycin inhibited FGF-2 binding to cells with an $IC_{50}$ of ~20 μM. b, wild-type and pgsA cells were incubated with 0.5 mM $Arg_9$-BODIPY and increasing concentrations of guanidinoneomycin. After 1 h the cells were analyzed by flow cytometry. Guanidinoneomycin is able to partially block $Arg_9$ binding to the surface of cells. The signal saturates once it reaches that of pgsA cells incubated with the fluorescent peptide. Inset, relative fluorescence of untreated wild-type cells (a), wild-type cells treated with fluorescent $Arg_9$ (b), pgsA cells treated with $Arg_9$ (c), and wild-type cells treated with $Arg_9$ and 1 μM (d) or 300 μM guanidinoneomycin (e).

FIG. 6. Visualization of guanidinoneomycin uptake in CHO cells. a, wild-type cells were incubated with a conjugate of biotinylated guanidinoneomycin and streptavidinylated Alexa-488 for 1 h at 37° C. An overlay of the 4',6-diamidino-2-phenylindole nuclear stain (blue) and fluorescent guanidinoneomycin conjugate (green) shows internalization in punctate vesicular structures. When the same experiment was performed with heparan/chondroitin sulfate-deficient pgsA cells (b), no cell-associated guanidinoglycoside fluorescence was observed. c, incubation of wild-type cells with 0.4 M sucrose inhibited uptake, whereas incubation with 5 mM amiloride had no effect.

FIG. 7. Guanidinoneomycin can efficiently deliver large, bioactive cargo into the cell in a heparan/chondroitin sulfate-dependent manner. Various combinations of guanidinoneomycin, saporin, and streptavidinylated saporin (~130 kDa) were added to cells. After 4 days, the number of viable cells was estimated using CellTiter assay ("Experimental Procedures"), where the emission at 575 nm corresponds to the relative number of viable cells. Guanidinoneomycin-biotin does not display cell lysis activity on wild-type (black) or pgsA (pink) cells up to the highest concentration examined (84 nM). Little to no cell death was observed in both wild-type (blue) and pgsA (gray) cells when incubated with a mixture of non-streptavidinylated saporin and guanidinoneomycin-biotin. Cell toxicity was observed when wild-type cells were incubated with guanidinoneomycin conjugated to saporin through biotin-streptavidin (red) with an $LD_{50}$ of ~2 nM. pgsA cells were relatively resistant to the guanidinoglycoside-toxin conjugate (green).

References:
1. Ryser, H. J.-P. (1968) Science 159, 390-396
2. Dietz, G. P., and Bahr, M. (2004) Mol. Cell. Neurosci. 27, 85-131
3. Wadia, J. S., and Dowdy, S. F. (2005) Adv. Drug Del. Rev. 57, 579-596
4. Frankel, A. D., and Pabo, C. O. (1988) Cell 55, 1189-1193
5. Green, M., and Loewenstein, P. M. (1988) Cell 55, 1179-1188
6. Futaki, S. (2005) Adv. Drug Deliv. Rev. 57, 547-558
7. Futaki, S. (2006) Biopolymers Pept. Sci. 84, 241-249
8. Futaki, S., Nakase, I., Suzuki, T., Zhang, Y., and Sugiura, Y. (2002) Biochemistry 41, 7925-7930
9. Wender, P. A., Mitchell, D. J., Pattabiraman, K., Pelkey, E. T., Steinman, L., and Rothbard, J. B. (2000) Proc. Natl. Acad. Sci. 97, 13003-13008
10. Umezawa, N., Gelman, M. A., Haigis, M. C., Raines, R. T., and Gellman, S. H. (2002) J. Am. Chem. Soc. 124, 368-369
11. Fillon, Y. A., Anderson, J. P., and Chmielewski, J. (2005) J. Am. Chem. Soc. 127, 11798-11803
12. Chung, H. H., Harms, G., Seong, C. M., Choi, B. H., Min, C., Taulane, J. P., and Goodman, M. (2004) Biopolymers 76, 83-96
13. Fernandez-Carneado, J., Van Gool, M., Martos, V., Castel, S., Prados, P., de Mendoza, J., and Giralt, E. (2005) J. Am. Chem. Soc. 127, 869-874
14. Rothbard, J. B., Jessop, T. C., and Wender, P. A. (2005) Adv. Drug. Deliv. Rev. 57, 495-504
15. Rothbard, J. B., Jessop, T. C., Lewis, R. S., Murray, B. A., and Wender, P. A. (2004) J. Am. Chem. Soc. 126, 9506-9507
16. Caesar, C. E. B., Esbjorner, E. K., Lincoln, P., and Norden, B. (2006) Biochemistry 45, 7682-7692
17. Hitz, T., Iten, R., Gardiner, J., Namoto, K., Walde, P., and Seebach, D. (2006) Biochemistry 45, 5817-5829
18. Tyagi, M., Rusnati, M., Presta, M., and Giacca, M. (2001) J. Biol. Chem. 276, 3254-3261
19. Fuchs, S. M., and Raines, R. T. (2004) Biochemistry 43, 2438-2444 10. Richard, J. P., Melikov, K., Brooks, H., Prevot, P., Lebleu, B., and Chemomordik, L. V. (2005) J. Biol. Chem. 280, 15300-15306
21. Luedtke, N. W., Baker, T. J., Goodman, M., and Tor, Y. (2000) J. Am. Chem. Soc. 122, 12035-12036
22. Luedtke, N. W., Carmichael, P., and Tor, Y. (2003) J. Am. Chem. Soc. 125, 12374-12375
23. Esko, J. D., Stewart, T. E., and Taylor, W. H. (1985) Proc. Natl. Acad. Sci. U.S.A. 82, 3197-3201
24. Bai, X. M., Wei, G., Sinha, A., and Esko, J. D. (1999) J. Biol. Chem. 274, 13017-13024
25. Wei, G., Bai, X., Sarkar, A. K., and Esko, J. D. (1999) J. Biol. Chem. 274, 7857-7864
26. Chambers, H. F. (2006) in Goodman & Gilman's The Pharmacological Basis of Therapeutics (Brunton, L. L., Lazo, J. S., and Parker, K. L., eds) 11th Ed., pp. 1155-1171, McGraw-Hill, New York
27. Lidholt, K., Weinke, J. L., Kiser, C. S., Lugemwa, F. N., Bame, K. J., Cheifetz, S., Massaguo, J., Lindahl, U., and Esko, J. D. (1992) Proc. Natl. Acad. Sci. U.S.A. 89, 2267-2271
28. Deutscher, S. L., Nuwayhid, N., Stanley, P., Briles, E. I., and Hirschberg, C. B. (1984) Cell 39, 295-299

29. Yayon, A., Klagsbrun, M., Esko, J. D., Leder, P., and Ornitz, D. M. (1991) *Cell* 64, 841-848
30. Rapraeger, A. C., Krufka, A., and Olwin, B. B. (1991) *Science* 252, 1705-1708
31. Lamaze, C., and Schmid, S. L. (1995) *Curr. Opin. Cell Biol.* 7, 573-580
32. Kaplan, I. M., Wadia, J. S., and Dowdy, S. F. (2005) *J. Controlled Release* 102, 247-253
33. Williams, K. J., and Fuki, I. V. (1997) Curr. Opin. Lipidol. 8, 253-262 34. Flavell, D. J. (1998) *Curr. Top Microbiol. Immunol.* 234, 57-61
35. Esko, J. D., and Selleck, S. B. (2002) *Annu. Rev. Biochem.* 71, 435-471

Example 13

General Synthesis of an N-Hydroxysuccinimide (NHS) Activated Ester of Guanidinylated Neomycin (GNeo)

All reagents were obtained with the highest available purity and purchased from the Aldrich-Sigma Chemical Company. Proton and carbon NMR were recorded at 500 MHz and 125 MHz, respectively, using an ECA-500 Joel spectrophotometer. The proton and carbon assignments were based on COSY, TOCSY, and HSQC experiments. Electrospray ionization (ESI) mass spectrometry was conducted employing a ThermoFinnigan LCQDECA-MS spectrometer Infra red spectroscopy was recorded in a JASCO FT/1R-4100 spectrophotometer. See Sarrazin, S. et al., *Molecular Therapy* 18(7): 1268-1274 (2010) which is incorporated by reference in its entirety.
Scheme 1 illustrates the synthesis of NHS-GNeo.

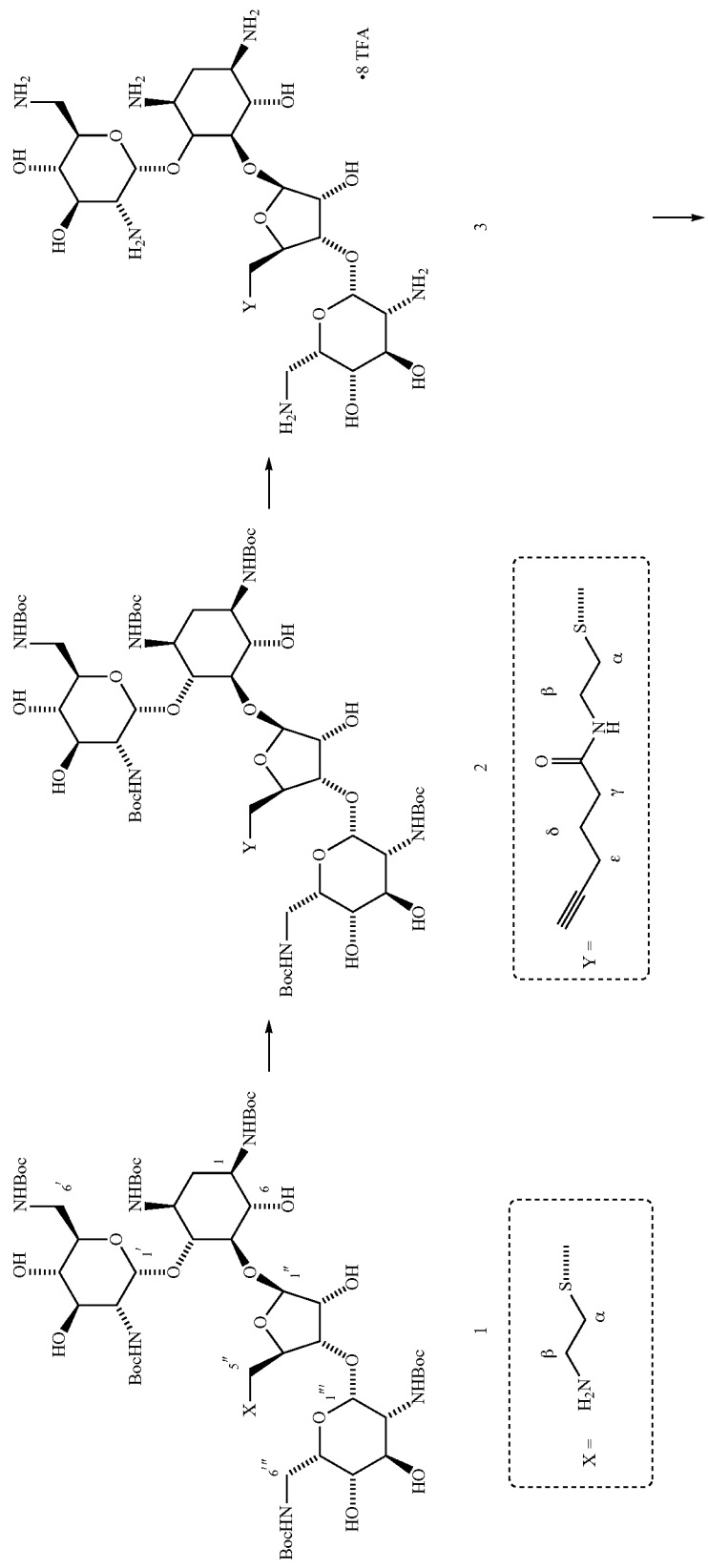

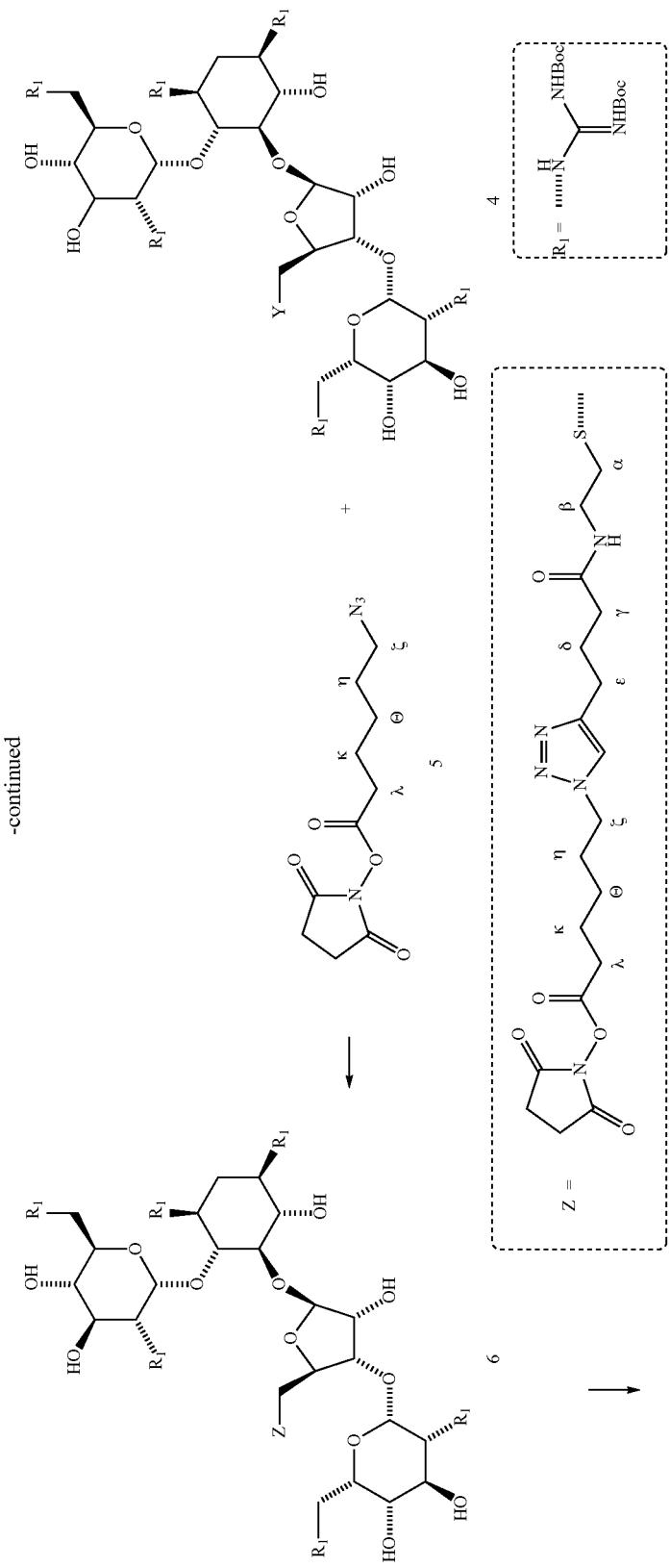

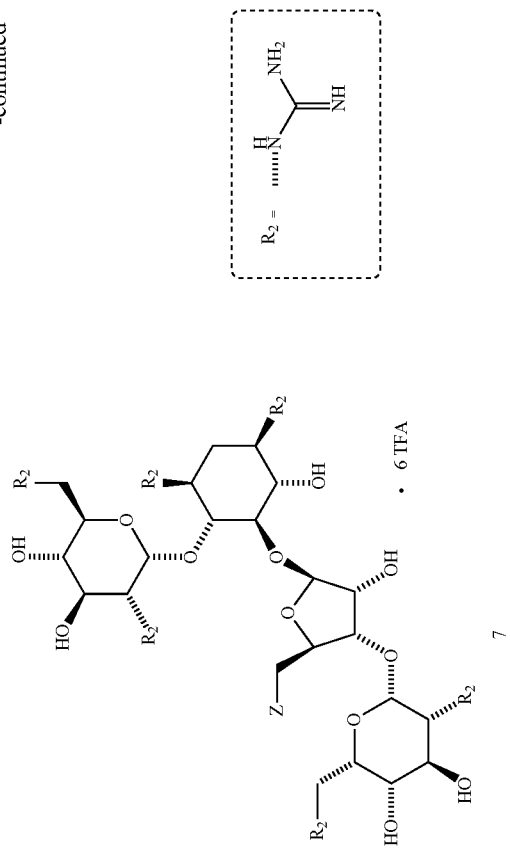

Compound 1 was prepared as previously reported (Kirk, S. R, Luedtke, N. W. and Tor, Y. *J. Am. Chem. Soc.* 2000, 122, 980-981.

Compound 2. To a solution of 6-hexynoic acid (26 μL, 0.236 mmol) in 400 μL of $CH_2Cl_2$ was added 1-ethyl-3-(3'-dimethylaminopropyl)carbodiimide hydrochloride (45 mg, 0.234 mmol). After 10 min, compound 1 (260 mg, 0.204 mmol) dissolved in 500 μL of $CH_2Cl_2$ and N,N'-diisopropylamine (81 μL, 0.468 mmol) were added. The reaction mixture was stirred at room temperature for 8 h. The reaction mixture was diluted in 200 mL of $CH_2Cl_2$ and extracted with water (2×50 mL). The organic layer was washed with brine (50 mL), dried over sodium sulfate, and concentrated in vacuo. The reaction products were purified via flash chromatography using silica gel and (0-4% $CH_3OH$ in $CH_2Cl_2$) as eluent to afford a white solid (200 mg, 72%). $R_f$=0.43 (10% $CH_3OH$ in $CH_2Cl_2$, ninhydrin stain). The compound was characterized by $^1H$ NMR ($CD_3OD$) and $^{13}C$ NMR ($CD_3OD$). LRMS (ESI): calculated for $C_{61}H_{105}N_7O_{25}S$ $[M+H]^+$ 1367.7, found 1368.3.

Compound 3. To a solution of 2 (200 mg, 0.146 mmol) in 2 mL of $CH_2Cl_2$ were added triisopropylsilane (20 μL, 0.50% v/v) and trifluoroacetic acid (2 mL). The reaction mixture was stirred at room temperature for 2 h. Then, the reaction mixture was concentrated in vacuo (2× using toluene to azeotrope the trifluoroacetic acid) and the residue obtained was dissolved in water (20 mL) and extracted with $CH_2Cl_2$ (100 mL). The aqueous solution was filtered and lyophilized to afford a white solid (205 mg, 97%). The compound was characterized using $^1H$ NMR ($D_2O$) and $^{13}C$ NMR ($CD_3OD$). LRMS (ESI): calculated for $C_{31}H_{57}N_7O_{13}S$ $[M+H]^+$ 767.4, found 768.3.

Compound 4. A solution of 3 (150 mg, 0.104 mmol) in 200 μL of $CH_3OH$ was treated with triethylamine (200 μL, 1.44 mmol) and N,N'-diBoc-N''-triflylguanidine (Baker, T. J., Luedtke, N. W., Tor, Y. and Goodman, M. *J. Org. Chem.* 2000, 65, 9054-9058.) (563 mg, 1.44 mmol) dissolved in 800 μL of $CH_2Cl_2$. The reaction mixture was stirred under argon at room temperature for 36 h. Then, the reaction mixture was concentrated in vacuo and the residue obtained was diluted with $CH_2Cl_2$ (200 mL) and extracted with 5% aqueous $NaHCO_3$ solution (2×50 mL). The $CH_2Cl_2$ solution was washed with brine (50 mL), dried over sodium sulfate, and concentrated in vacuo. The product was purified via flash chromatography using silica gel and (0-2% $CH_3OH$ in $CH_2Cl_2$) as eluent to afford a white solid (140 mg, 61%). $R_f$=0.54 (5% $CH_3OH$ in $CH_2Cl_2$, ninhydrin stain). The compound was characterized using $^1H$ NMR ($CD_3OD$) and $^{13}C$ NMR ($CD_3OD$). LRMS (ESI): calculated for $C_{97}H_{165}N_{19}O_{37}S$ $[M+2H]^{2+}$ 2220.1, found 1110.9.

Compound 5 (over two steps). A stirred solution of 6-bromohexanoic acid (1.00 g, 5.15 mmol) in DMF (5 mL) was treated with sodium azide (5.05 g, 7.78 mmol) and heated to 85° C. for 3 h. The reaction mixture was concentrated in vacuo and the crude obtained was diluted in 300 mL of $CH_2Cl_2$ and washed with 0.1N aqueous HCl. The $CH_2Cl_2$ solution was washed with brine (50 mL), dried over sodium sulfate, and concentrated in vacuo to yield an oil (6-aziodohexanoic acid, 730 mg, 90%) that was used in the next step without any further purification. The 6-azidohexanoic acid (500 mg, 3.18 mmol) and N-hydroxysuccinimide (366 mg, 3.18 mmol) were dissolved in ($CH_2Cl_2$/DMF 9:1 v/v) 10 mL and treated with 1-ethyl-3-(3'-dimethylaminopropyl)carbodiimide hydrochloride (610 mg, 3.18 mmol). The reaction mixture was stirred at room temperature overnight. The solvent was concentrated in vacuo, the residue was diluted with 300 mL of $CH_2Cl_2$ and washed with water (2×50 mL). The organic layer was washed with brine (50 mL), dried over sodium sulfate, and concentrated in vacuo. The product was purified via flash chromatography using silica gel and (100% $CH_2Cl_2$) as eluent to afford a dark-yellow oil (650 mg, 80%). $R_f$=0.46 (5% $CH_3OH$ in $CH_2Cl_2$, bromocresol stain). The compound was characterized using $^1H$ NMR (DMSO-$d_6$) and $^{13}C$ NMR (DMSO-$d_6$). LRMS (ESI): calculated for $C_{10}H_{14}N_4O_4[M+H]^+$ 254.1, found 255.0.

Compound 6. Compounds 4 (100 mg, 0.045 mmol) and 5 (17 mg, 0.067 mmol) were dissolved in 100 μL of acetonitrile and treated with 10 mol % CuBr (56 μL, 0.080 M solution in acetonitrile) and 10 mol % (56 μL, 0.080 M solution in acetonitrile) of tris[(1-benzyl-1H-1,2,3-triazol-4-yl)methyl]amine (ligand) in acetonitrile. The reaction was allowed to stir at room temperature under an argon atmosphere. After 8 hr, an additional 10 mol % of each CuBr and ligand were added. The reaction mixture was reacted for 24 h, after which flash chromatography using silica gel and (2% $CH_3OH$ in $CH_2Cl_2$) as eluent afforded a white solid (81 mg, 73%). $R_f$=0.44 (5% $CH_3OH$ in $CH_2Cl_2$, ninhydrin stain). The compound was characterized using $^1H$ NMR (DMSO-$d_6$) and $^{13}C$ NMR (DMSO-$d_6$). LRMS (ESI): calculated for $C_{107}H_{179}N_{23}O_{41}S$ $[M+2Na]^{2+}$2474.2, found 1260.3.

Compound 7. To a solution of 6 (81 mg, 0.033 mmol) in 2 mL of $CH_2Cl_2$ were added triisopropylsilane (20 μL, 0.50% v/v) and trifluoroacetic acid (2 mL). The reaction mixture was stirred at room temperature for 2 h. Then the reaction mixture was concentrated in vacuo (2× using toluene to azeotrope the trifluoroacetic acid) and the residue obtained was dissolved in cold water (5 mL) and filtered. The aqueous solution was filtered and lyophilized to afford a white solid (60 mg, 94%). The compound was characterized using $^1H$ NMR (DMSO-$d_6$) and $^{13}C$ NMR (DMSO-$d_6$). LRMS (ESI): calculated for $C_{47}H_{83}N_{23}O_{17}S$ $[M+H]^+$ 1273.6, found 1274.4.

Example 14

Uptake of a Biotinylated Guanidinylated Neomycin (GNeo)—Streptavidin-Coated Quantum Dots (QD325) in Chinese Hamster Ovary (CHO) Cells GNeo-biotin (12 μmol/l) was added to 300 nmol/l Streptavidin-QD525 (Invitrogen, 5-10 streptavidin/quantum dot) in Hank's balanced salt solution for 30 minutes at room temperature. Under these conditions, the conjugate contains up to 40 GNeo moieties. The GNeo-QD525 preparation was then diluted in normal growth medium to 5 nmol/l of quantum dots. Flow cytometry experiments were performed after incubation of cells for 1 hour with GNeo-QD525 under otherwise normal growth conditions. After uptake, cells were lifted using 10× trypsin/EDTA (0.5%/4.8 mmol/L, Invitrogen) for 15 minutes and rinsed twice in phosphate-buffered saline (PBS) before being analyzed by FACS. Unconjugated streptavidin-QD525 was used as a negative control. For fluorescent microscopy imaging, cells were incubated with GNeo-QD525 for 30 minutes. After three washes in medium, fresh medium was added to the cells. After 2.5 hours, cells were rinsed in Hank's balanced salt solution, labeled with Hoechst and LysoTracker Red following instructions provided by the manufacturer (Invitrogen). Images were captured with a DeltaVision Restoration system (Applied Precision, Issaquah, Wash.) seated on an Olympus IX70 microscope (Olympus, Center Valley, Pa.). Optical sections were acquired in 0.2 μm steps in the z axis using a ×100 Nikon (NA 1.3) oil immersion objective (Nikon, Melville, N.Y.). Images were deconvolved on a softWoRx workstation (Applied Precision) and reconstituted in three dimensions using Volocity software (PerkinElmer, Waltham, Mass.).

Figure 12:
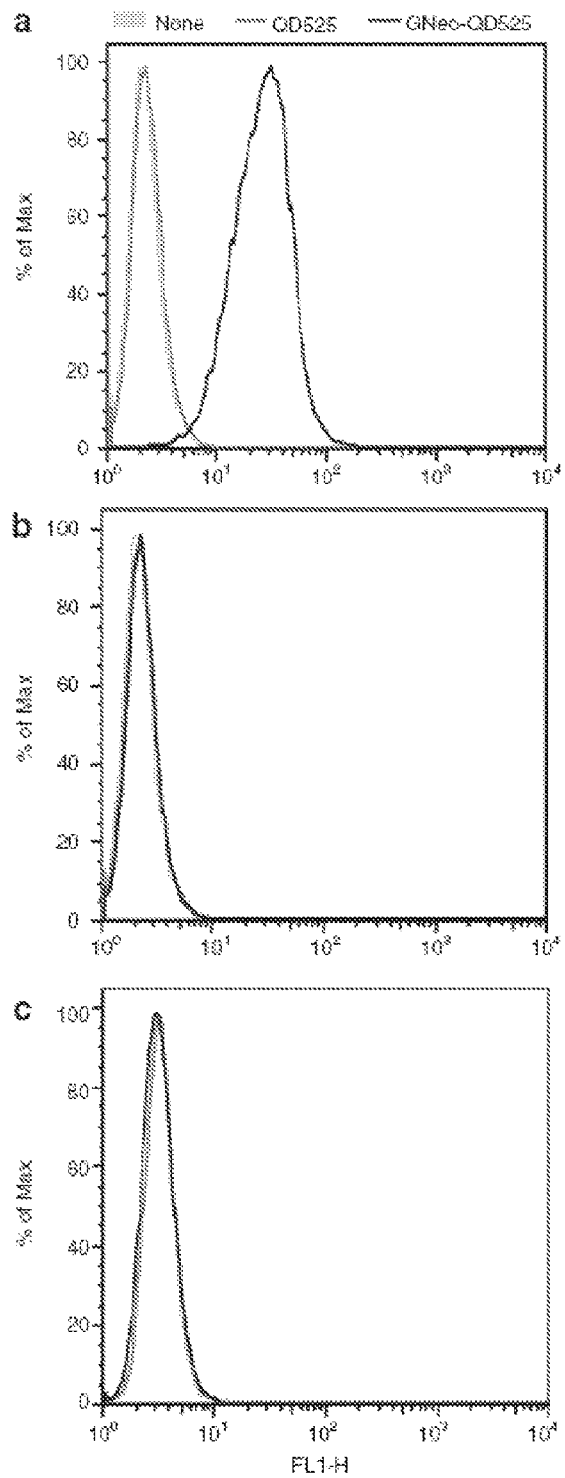
FIG. 12 shows the dependency of GNeo-QD525 uptake on heparan sulfate. (a) Wildtype Chinese hamster ovary cells, (b) mutant pgsA-745 deficient in heparan sulfate and chondroitin sulfate, and (c) mutant pgsD-677 deficient in heparan sulfate were incubated with 5 nmol/l GNeo-QD525 (black), QD525 (dark gray), or untreated (none, light gray area) for 2 hours under normal growth conditions. The cells were rinsed twice and lifted with trypsin/EDTA before being analyzed by flow cytometry.
Figure 13:
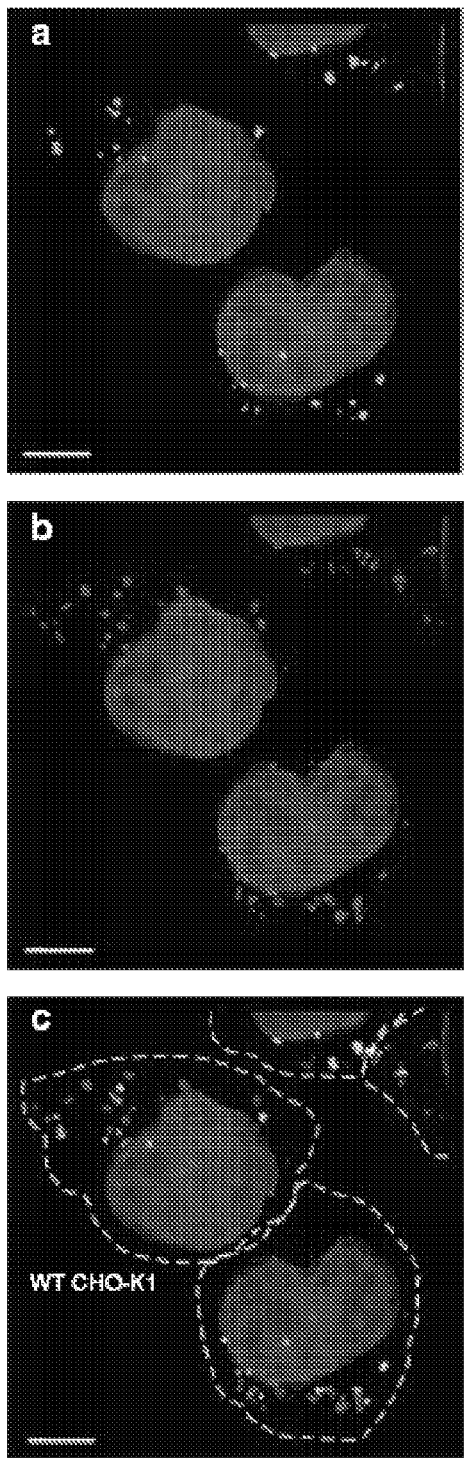
FIG. 13 shows GNeo-QD525 colocalizes in lysosomes. Images were captured with a DeltaVision Restoration microscope system and were deconvolved to show the localization of (a) GNeo-QD525, (b) lysosomes in a single Z-stack plane. The merged images from a and b are shown in c with the outline of cells (hatched line) drawn based on a phase contrast micrograph. Bar=5 μm.

Incubation of wild-type CHO cells with 5 nmol/l GNeo-QD525 led to fluorescent labeling of the cells, which was quantified by flow cytometry (FIG. 12*a*, black line). Significant fluorescence was observed compared to controls in which the quantum dots were not added to the cells (shaded area in FIG. 12a) or in cells incubated with quantum dots not derivatized with GNeo (QD525, gray line). Under these conditions, the majority of the fluorescence signal was due to uptake of GNeo-QD525 because the cells were treated with trypsin prior to flow cytometry. Control experiments in which cells were incubated with GNeo-QD525 at 4° C. showed that nearly all of the cell-associated material was released by trypsin treatment at low temperature. In contrast, at 37° C. about 20% of GNeo-QD525 was resistant to trypsin treatment, a value that increased with time. Uptake was completely dependent on glycosaminoglycans because pgsA-745 cells lacking both heparan sulfate and chondroitin sulfate did not show a significant signal by flow cytometry (FIG. 12b). Similar results were obtained in pgsD-677 cells, which lack heparin sulfate and make about two- to threefold more chondroitin/dermatan sulfate (FIG. 12c). Thus, GNeo-conjugated quantum dots behaved much like GNeo-streptavidin-Alexa488 and GNeostreptavidin-phycoerythrin-Cy5 conjugates described previously in terms of their high selectivity for heparan sulfate. Imaging of the cells by deconvolution fluorescence microscopy showed that GNeo-QD525 was present in punctate structures (FIG. 13a, light colored spots). Uptake was a relatively slow process because GNeo-QD525 did not appear inside the cells for ~45 minutes. Many of the punctate structures containing GNeo-QD525 at 37° C. also co-stained with LysoTracker (darker spots) (FIGS. 13b,c). These findings indicated that GNeo could deliver very high molecular weight cargo (estimated size of the streptavidinylated quantum dots >107 Da) to lysosomes by way of cell surface heparan sulfate proteoglycans.

Example 15

Conjugation of Guanidinylated Neomycin (GNeo) to Enzymes described in Example 13) was empirically determined based on the binding of the conjugated enzyme to heparin-Sepharose. Thus, the conjugation of the GNeo-NHS to GUS and α-1-iduronidase was performed at 4° C. using 50 and 100 molar excess ratio, respectively, of GNeo-NHS (5.56 μmol/l GUS with 278 μmol/L GNeo-NHS, 5 μmol/l α-1-iduronidase with 500 μmol/l GNeo-NHS) in PBS (pH 7.4). After 2 hours, excess GNeo-NHS was removed by desalting on a Zeba Desalting Column (Pierce). Conjugated enzyme was purified by heparin affinity chromatography (Hi-Trap Heparin-HP 1 ml; GE Biosciences, Piscataway, N.J.). The column was equilibrated in PBS, and samples were loaded onto the column and incubated for 10 minutes at room temperature. Nonbound material was removed with 3 ml of PBS (FT1). A second washing step was performed (FT2) before elution using 3 ml each of 0.3, 0.6, 0.9, 1.2, and 2 mol/l NaCl. Each fraction was desalted on Zeba column, and the protein concentration was measured. The majority of conjugated enzyme was eluted with 0.6 mol/l NaCl.

Figure 14:
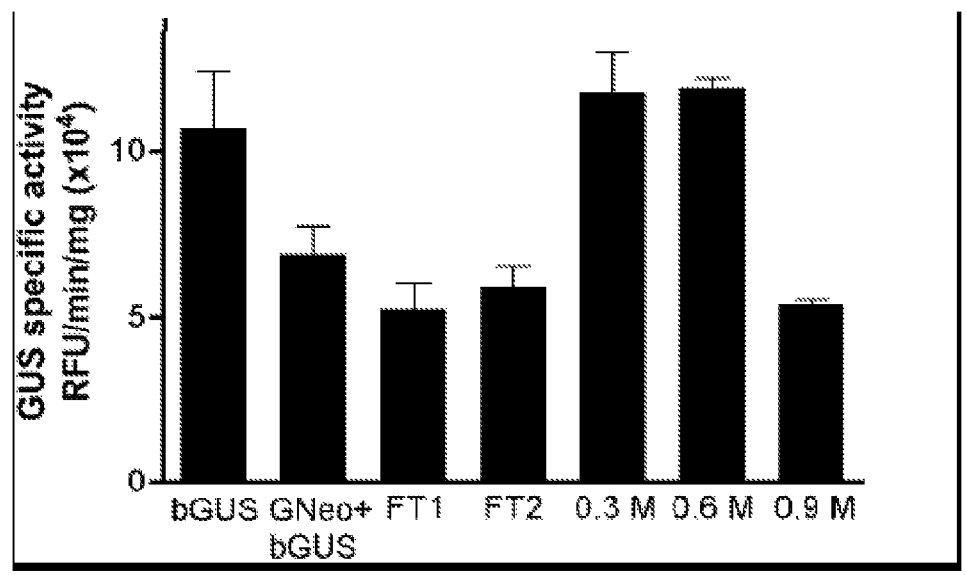
FIG. 14 shows the enzyme activity of bGus before and after conjugation to GNeo and after purification on heparin-Sepharose.

Enzyme activity was assayed using the method described in Example 16 before and after conjugation with GNeo-NHS and in the various fractions collected by heparin sepharose chromatography. As shown in FIG. 14, the addition of GNeo had at most only a minor effect on enzyme specific activity (~30% in the unfractionated preparation, but no effect on the modified enzyme that eluted at 0.3 and 0.6 mol/L NaCl).

Example 16

Enzyme Activity Assays

GUS activity was measured by assaying the conversion of 4-methylumbelliferyl β-d-glucuronide (MUG; Sigma) into the fluorochrome 4-methylumbelliferone. The assay was performed in 96-well plates, using 100 μl of reaction buffer containing 50 mmol/L sodium acetate (pH 5.2), 10 mmol/L

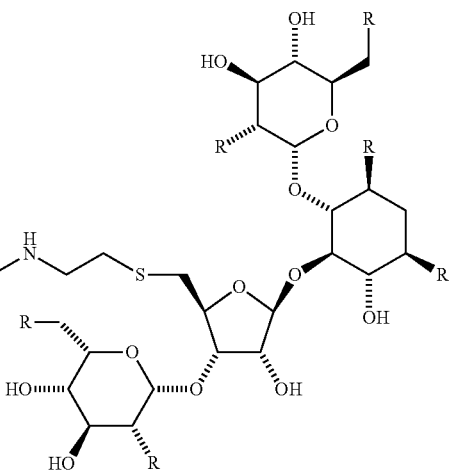

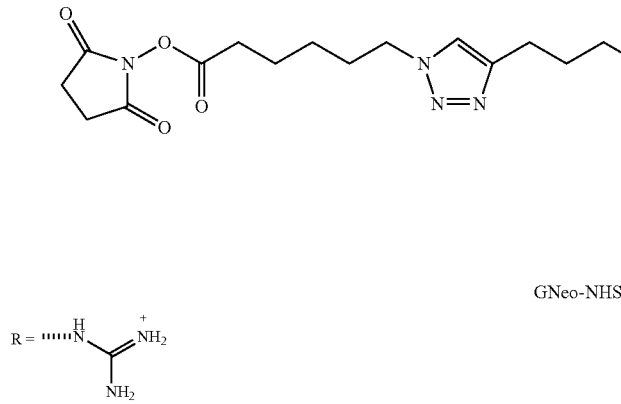

GNeo-NHS

Bovine β-D-glucuronidase (bGUS) was dissolved in 50 mmol/L sodium acetate buffer (pH 5.2), and protein concentration was estimated by BCA assay (Pierce, Rockford, Ill.). The optimal concentration of GNeo-NHS (prepared as EDTA, 0.01% bovine serum albumin, 0.1% Triton X-100, 14.3 mg of MUG, and enzyme. After 1 hour at 37° C., fluorescent product was measured by fluorimetry (excitation at 360 nm, emission at 460 nm) and quantified using a standard curve of 4-methylumbelliferone. One unit (U) of activity is defined as the liberation of 1 mg of 4-methylumbelliferone per hour at pH 5.2, 37° C. α-1-iduronidase activity was measured in a similar way using 4-methylumbelliferyl α-1-iduronide (Glycosynth, Warrington, UK) as substrate. The assay was performed in 10 µl of 50 mmol/L sodium formate (pH 3) buffer containing 10 mmol/L NaCl, 0.1 mg/ml bovine serum albumin, 50 µmol/l substrate, and 2 µl of enzyme.

The 6-O-phosphate group on the M6P recognition site of GUS or α-1-iduronidase was removed with 250 U of AP (Sigma) per mg of protein (5 hours, 37° C. in a 25 mmol/L Tris/HCl buffer (pH 8) containing 140 mmol/L NaCl).

Example 17

Uptake of GNeo-Gus by Fibroblasts

Figure 15:
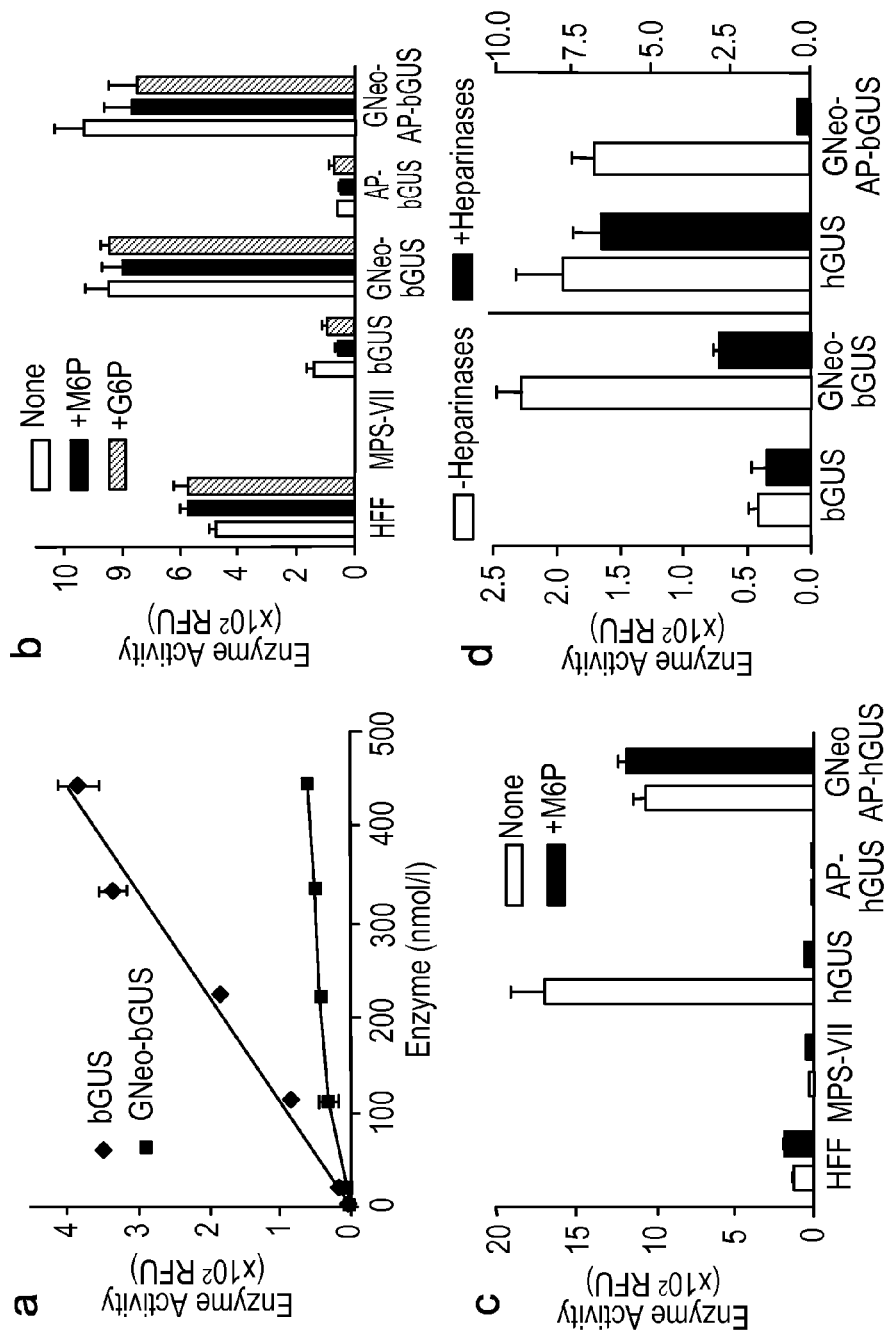
FIG. 15 shows GNeo delivery of GUS is M6P-independent. (a) MPS VII fibroblasts were treated with the indicated concentration of bGUS or GNeo-bGUS for 2 hours and subsequently assayed for β-glucuronidase activity. (b) MPS VII cells were treated with 5 nmol/l of the indicated bovine enzyme preparations in growth medium in the absence (open bars) or in the presence of 5 mmol/l mannose-6-phosphate (filled bars) or glucose-6-phosphate (gray bars), and assayed for β-glucuronidase activity. (c) MPS VII cells were treated with 1 nmol/l of the indicated human enzymes in the presence (filled bars) and absence (open bars) of 5 mmol/l mannose-6-phosphate and assayed for β-glucuronidase activity. (d) MPS VII cells were treated with medium in the absence (open bars) or with a mixture of heparin lyases (filled bars) 15 minutes prior to addition of 5 nmol/l bGUS or GNeo-bGUS or 1 nmol/l hGUS or GNeo-AP-hGUS.

To test whether GNeo-bGus was taken up by GUS-deficient cells, enzyme activity was measured in MPR VII fibroblasts after 2-hour incubation with various concentrations of unmodified bGus and G-Neo-bGus (see FIG. 15a). Normal HFF, MPS VII, and MPS I fibroblasts were cultured in Earl's Minimal Essential Medium supplemented with 15% of fetal bovine serum and penicillin/streptomycin (Invitrogen). Approximately 8×104 cells in 0.4 ml of medium were seeded in each well of a 24-well plate. After 3 days, cells were incubated in fresh medium with and without 5 mmol/L of M6P or glucose 6-phosphate (G6P) (Sigma). After 10 minutes, enzymes were added to the well at the concentrations indicated in the figure legends. The cells were incubated for 2 hours at 37° C., washed twice with PBS, treated with trypsin/EDTA, and then combined with complete medium to inhibit the trypsin. Cells were sedimented by centrifugation, and then resuspended in 30 µl of lysis buffer [activity assay buffer containing 0.5% Triton X-100 and a mixture of protease inhibitors (Sigma)]. In some experiments, cells were treated 3 hours with recombinant heparin lyases I, II, and III (5 mU/ml) in serum-free medium, and uptake was measured as described above in medium containing heparinases. Enzyme activity in the cell extracts was measured in triplicate using 5 µg of total cell protein. All assays were performed in triplicate, and each experiment was repeated at least twice on difference occasions.

Poor uptake of bGUS occurred at all concentrations tested, whereas uptake of GNeo-bGUS was proportional to concentration up to 450 nmol/l, the highest concentration tested. When cells were incubated with 20 nmol/l of GNeo-bGUS for 2 hours, the cells took up 0.5% of the enzyme, whereas in the absence of GNeo conjugation, cells took up only 0.06% of the added enzyme. Neither bGUS nor GNeo-bGUS was degraded in cell-free extracts based on enzymatic activity assays, suggesting that incorporated enzyme was stable.

As shown in FIG. 15b, endogenous GUS activity in human foreskin fibroblasts (HFF) was not affected by mannose-6-phosphate (M6P) or glucose-6-phosphate (G6P). Uptake of bGUS was reduced by 50%, however, by 5 mmol/l M6P but not by G6P. Analysis of variance showed that these differences were significant (P=0.0104). Treatment of bGUS with alkaline phosphatase (AP), which removes the terminal 6-phosphate group necessary for recognition, reduced uptake by ~50% as well, and the residual uptake was insensitive to M6P, consistent with the presence of a M6P-independent receptor on fibroblasts. In comparison, uptake of human recombinant GUS (hGUS) was robust (FIG. 15c), and the addition of M6P or treatment with AP-hGUS greatly inhibited uptake.

To test whether GNeo could confer high-uptake properties to GUS isoforms, conjugates of bGUS, AP-bGUS, or AP-hGUS were generated and added to human fibroblasts. The addition of GNeo dramatically increased enzyme uptake compared to the unmodified enzymes, exceeding the endogenous activity observed in untreated cells (FIGS. 15b,c). Free M6P had little, if any, effect on uptake, suggesting that the conjugated enzymes were not internalized via the CI-MPR pathway. Instead, uptake of the GNeo-conjugated enzymes depended on heparan sulfate, based on loss of uptake by prior treatment of the cells with heparin lyases, which depolymerizes the heparan sulfate chains on the surface of the cell. The incomplete inhibition of uptake of GNeo-bGUS by heparinase to the level observed with unmodified bGUS probably reflects incomplete digestion of heparan sulfate in this experiment and the presence of M6P-modified enzyme. The greater sensitivity of GNeo-AP-hGUS to heparinase probably reflects the lack of any M6P targeting signals in this preparation and the lower concentration of enzyme compared to bGUS (1 nmol/l versus 5 nmol/l, respectively). Uptake of unconjugated bGUS and hGUS was insensitive to treatment with heparin lyases.

Example 18

Internalized Enzymes Restore Normal Gag Turnover

To test whether internalized GUS was functionally localized in lysosomes, a label-chase format was used in which cells were incubated with $^{35}$S-labeled sulfate for 24 hours to radiolabel the sulfated glycosaminoglycans. The medium was changed, and after 24 hours, the amount of [$^{35}$S] glycosaminoglycans that remained associated with the cells was quantitated. Normal and MPS fibroblasts were incubated in DMEM/F12 medium supplemented with 10% dialyzed fetal bovine serum in order to increase the radiospecific activity of added $^{35}$S$_4$. Cells were seeded in a 12-well plate, and at confluence, 50 µCi of Na[$^{35}$S]O$_4$ (PerkinElmer) was added in 1 ml of fresh medium. After 24 hours, the cells were rinsed twice with PBS, exposed to GUS or α-iduronidase for 2 hours, rinsed twice, and then chased for 24 hours in complete growth medium. The cells were harvested with trypsin, centrifuged (500 g, 5 minutes), and washed once. The sedimented cells were then resuspended in 100 µl of RIPA buffer (Sigma) and counted by liquid scintillation spectrometry using Scintillator Ultima Gold XR (PerkinElmer).

Figure 16:
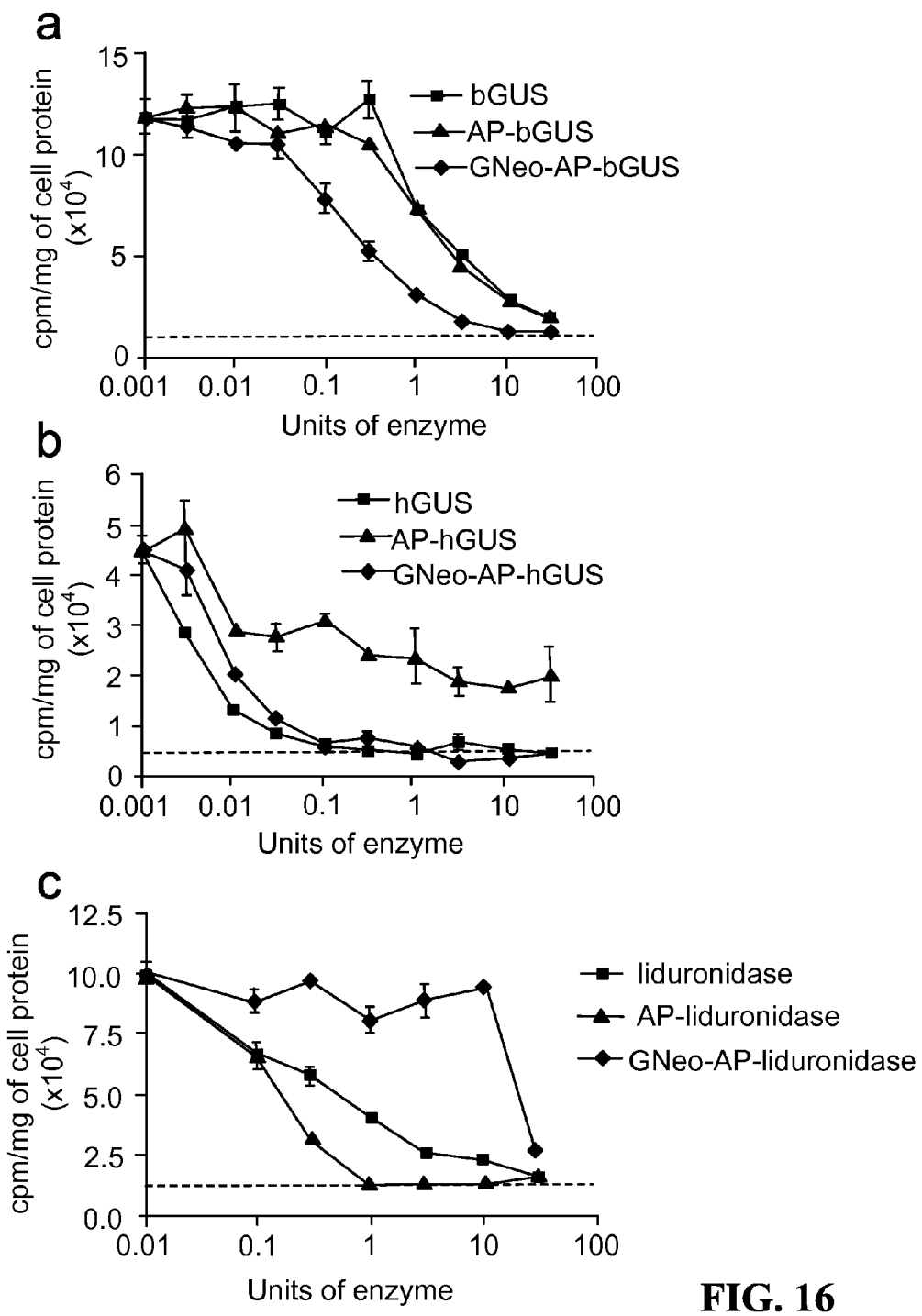
FIG. 16 shows GNeo delivery of lysosomal enzymes enhanced turnover of glycosaminoglycans in mucopolysaccharidosis (MPS) fibroblasts. (a,b) Normal and MPS VII or (c) MPS I fibroblasts were radiolabeled with $^{35}SO_4$ and chased for 24 hours with the indicated concentration of bovine βl-glucuronidases (a), human β-glucuronidases (b), and human α-L-iduronidase (c).

Under the conditions described above, MPS VII fibroblasts retained about tenfold more [$^{35}$S]glycosaminoglycans than normal HFF (FIG. 16a). Incubation of the cells with GNeo-AP-bGUS induced turnover, with an ED50 value of 150 mU of enzyme activity (FIG. 16a). bGUS and AP-bGUS also enhanced the turnover of the [$^{35}$S]glycosaminoglycans, but the ED50 values were tenfold higher, 1,500 mU (FIG. 16a). The uptake mechanism of AP-bGUS has not been well characterized, and may involve other receptors or fluid-phase pinocytosis. Recombinant hGUS, which is extensively modified with M6P, stimulated [$^{35}$S]glycosaminoglycans turnover with a low ED50 (~3 mU) and treatment with AP reduced its potency (ED50~300 mU)

(FIG. 5b). The addition of GNeo to AP-hGUS restored its efficacy to a level comparable to hGUS (ED50~10 mU) and with a similar dose-response curve.

To demonstrate the general utility of GNeo as a transporter, the same coupling method was applied to α-1-iduronidase, a lysosomal enzyme missing in MPS I patients (Hurler, Hurler-Scheie, and Scheie syndromes). Like MPS VII cells, MPS I fibroblasts also stored [$^{35}$S]glycosaminoglycans compared to wild-type HFF (FIG. 16c). As expected, recombinant therapeutic α-1-iduronidase (Aldurazyme) restored turnover, whereas AP-α-1-iduronidase was comparatively ineffective (ED50=1 U versus 30 U, respectively). Conjugating GNeo to AP-α-1-iduronidase enhanced its uptake, shifting the ED50 to 0.2 units, making it as effective or better than native Aldurazyme in restoring [$^{35}$S]glycosaminoglycan turnover.

Example 19

Synthesis of a Bifunctional Linkers

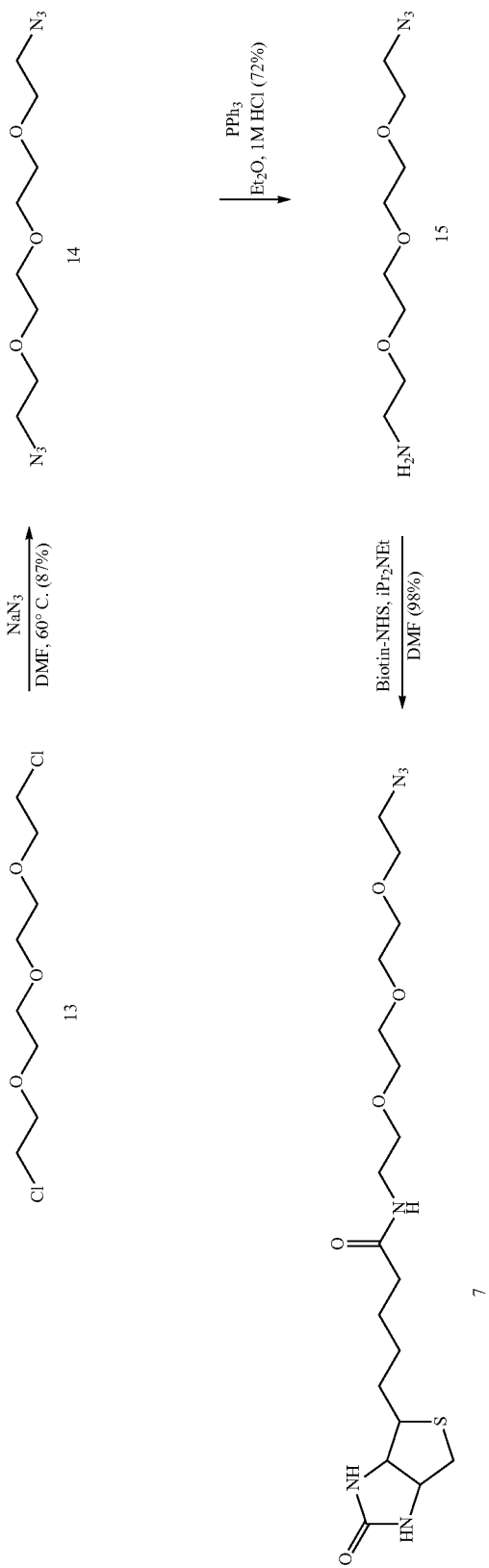

Synthesis of the Biotin-NHS ester and the sub-stoichiometric Stuadinger reduction were preformed according to literature procedures. See T. Mayer, M. E. Maier, *Eur. J. Org. Chem.* 2007, 28, 4711-4720; E. Klein, S. DeBonis, B. Thiede, D. A. Skoufias, F. Kozielskib, L. Lebeaua, *Bioorg. Med. Chem.* 2007, 15, 6474-6488; and A. W. Schwabacher, J. W. Lane, M. W. Schiesher, K. M. Leigh, C. W. Johnson, *J. Org. Chem.* 1998, 63, 1727-1729.

Compound 14. Bis[2-(2-chloroethoxy)ethyl]ether (0.711 g, 3.08 mmol) was diluted into N,N-dimethylformamide (12 mL) and treated with an excess of sodium azide (1.01 g, 15.4 mmol) at 60° C. for 4 h. The solvent was removed under reduced pressure and the resulting mixture was diluted into ether and filtered. The filtrate was again concentrated under reduced pressure, diluted into ether, and filtered. The final filtrate was concentrated under reduced pressure and used without further purification (0.645 g, 2.68 mmol, 87% yield).

Compound 15. 14 (0.381 g, 1.56 mmol) and triphenylphosphine (0.328 g, 1.25 mmol) were treated with diethyl ether (1.5 mL). To this, 1N HCl (1.5 mL) was added and the reaction was stirred vigorously for 12 h at RT. The reaction was diluted with ethyl ether (10 mL) and washed with 1N HCl. The combined aqueous layers were then washed with ether and turned basic using NaOH pellets. The basic aqueous layer was washed with ether. The combined organic phases were concentrated under reduced pressure to yield the product as an oil (0.246 mg, 1.13 mmol, 72% yield).

Compound 7. N,N-dimethylformamide (400 µL), Biotin NHS (72 mg, 0.211 mmol), and N,N-diisopropylethylamine (33 mg, 0.25 mmol) were added to 15 (42 mg, 0.19 mmol) for 12 h at RT. The reaction was concentrated under reduced pressure and purified on silica gel using flash chromatography (2-5% methanol in $CH_2Cl_2$) to afford the product as an oil (84 mg, 0.189 mmol, 98% yield).

Example 20

Synthesis of a Dimeric Linker

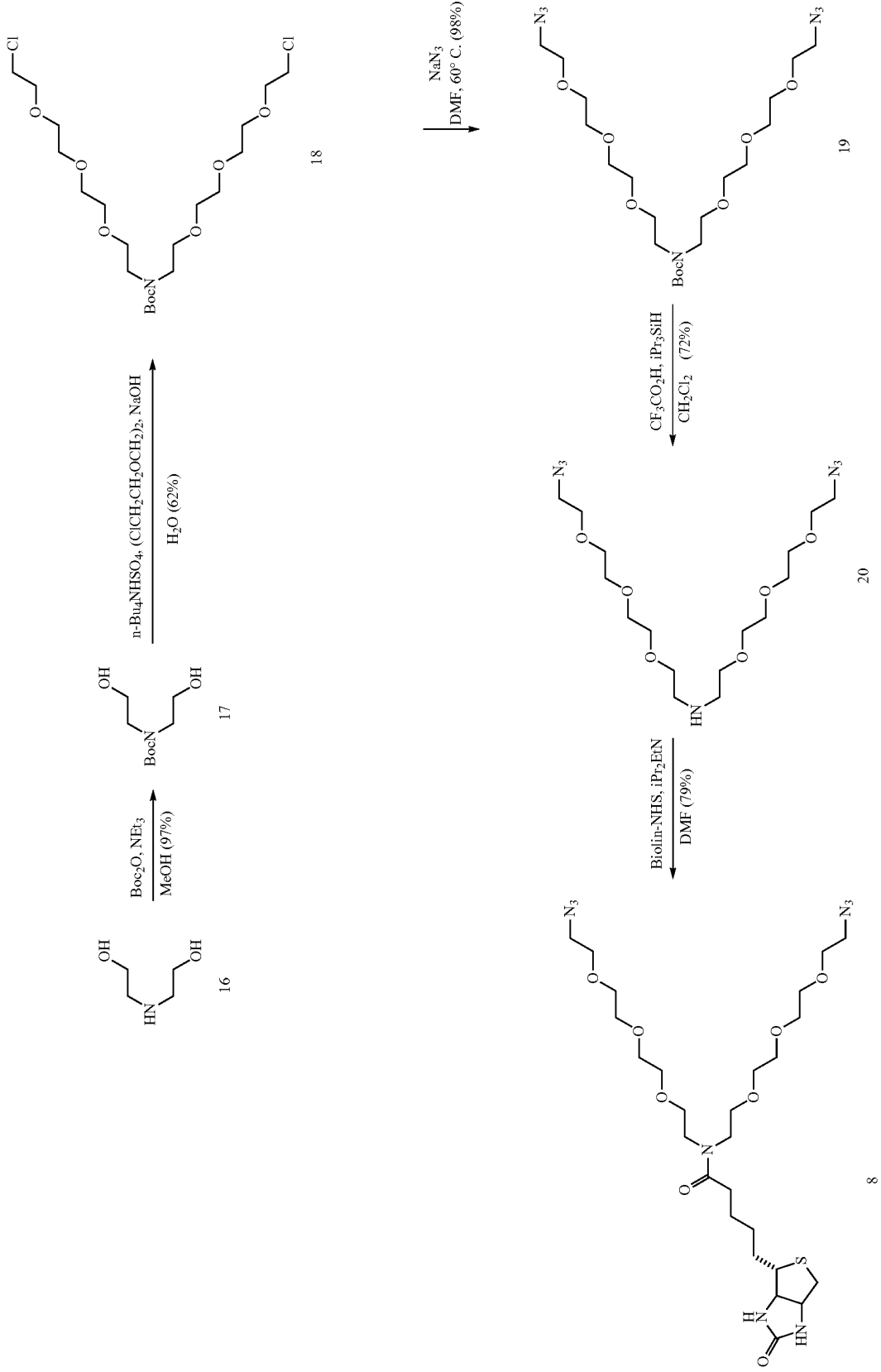

Precursors were prepared according to literature procedures. See C. P. Mandl, B. Konig, *Synthetic Commun.* 2004, 19, 3573-2578.

Compound 19. 18 (0.236 g, 0.466 mmol) was diluted into at 1:1 mixture of water and N,Ndimethylformamide (2 mL) and treated with sodium azide (0.242 g, 3.73 mmol) at 60° C. for 4 h. The solvent was removed under reduced pressure and the resulting mixture was diluted into ether and filtered. The filtrate was again concentrated under reduced pressure, diluted into ether, and filtered. The final filtrate was concentrated under reduced pressure and used without further purification (0.194 g, 0.374 mmol, 80% yield).

Compound 8. 19 (75 mg, 0.18 mmol) was diluted with $CHCl_3$ (6 mL) and treated with triisopropylsilane (200 µL), and trifluoroacetic acid (6 mL) for 15 min at RT. The reaction was diluted into toluene (30 mL) and concentrated under reduced pressure. The resulting oil was used without further purification, and was diluted with N,N-dimethylformamide (200 µL) and treated with Biotin NHS (95 mg, 0.28 mmol) and N,N-diisopropylethylamine (15 mg, 120 µmol) for 12 h at RT. The reaction was concentrated under reduced pressure and purified on silica gel using flash chromatography (2-5% methanol in $CH_2Cl_2$) to afford the product as an oil (51 mg, 0.079 mmol, 80% yield).

Example 21

Synthesis of Nomomeric and Dimeric Guanidinoneomycin Conjugates

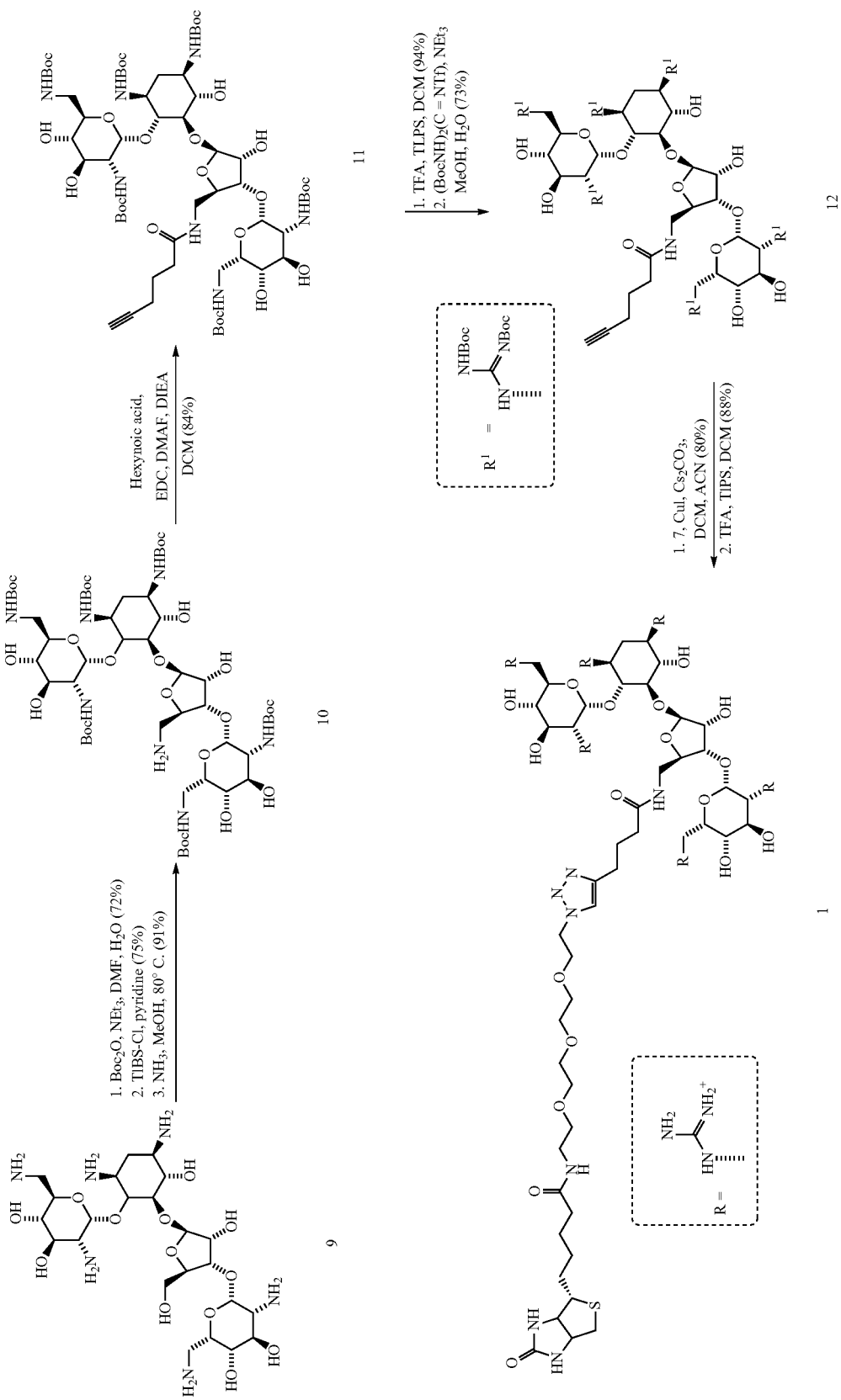

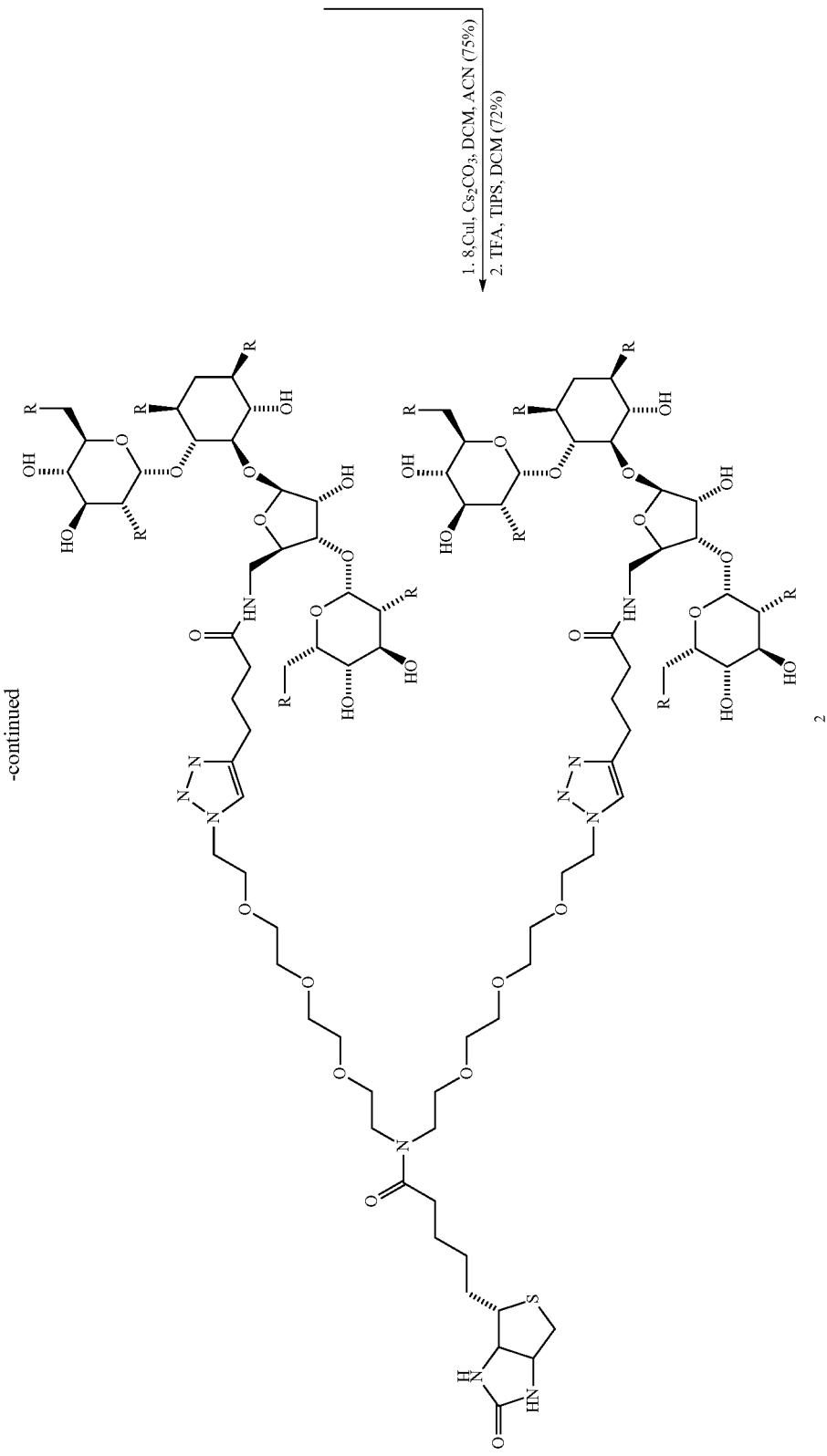

Precursors to compound 10 were prepared according to literature procedures. See L. Elson-Schwab, O. B. Garner, M. Schuksz, B. E. Crawford, J. D. Esko, Y. Tor, *Biol. Chem.* 2007, 282, 13585-13591; and N. X. Wang, A. G. Yu, G. X. Wang, X. H. Zhang, Q. S. Li, Z. Li, *Synthesis* 2007, 1154-1158.

Compound 11. 10 (290 mg, 0.24 mmol) was dissolved in $CH_2Cl_2$ (200 μL) and treated with hexynoic acid (40 mg, 0.35 mmol), N-(3-Dimethylaminopropyl)-N'-ethylcarbodiimide hydrochloride (54 mg, 0.28 mmol), and N,N-diisopropylethylamine (67 mg, 0.52 mmol) for 12 h at RT. The reaction was diluted into ethyl acetate (15 mL) and washed with water (3×15 mL), brine (15 mL), and dried over sodium sulfate. The combined organic layers were concentrated under reduced pressure and further purified on silica gel using flash chromatography (0-5% methanol in $CH_2Cl_2$) to afford the product as an off-white solid (260 mg, 0.20 mmol, 84% yield).

Compound 12. 11 (260 mg, 0.20 mmol) was dissolved in $CH_2Cl_2$ (4 mL), and treated with triisopropylsilane (200 μL) and trifluoroacetic acid (4 mL) for 15 min at RT. The reaction was diluted into toluene (30 mL) and concentrated under reduced pressure. The solid was then dissolved in water (10 mL) and washed with $CH_2Cl_2$ (3×15 mL). The aqueous phase was then reduced to a solid under reduced pressure. The crude product was dissolved in methanol (200 μL) and treated with a solution of N,N'-di-tertbutoxycarbonyl-N''-triflylguanidine (2.70 g, 6.80 mmol) and triethylamine (220 mg, 2.2 mmol) in $CH_2Cl_2$ (2 mL) for 36 h at RT. The reaction was then diluted into $CH_2Cl_2$ (15 mL), washed with water (3×10 mL), brine (10 mL), and dried over sodium sulfate. The combined organic layer were concentrated under reduced pressure and further purified by flash chromatography (0-3% methanol in $CH_2Cl_2$) to afford the product as an off-white solid (290 mg, 0.14 mmol, 69% yield over two steps).

Compound 1. 12 (25 mg, 12 mmol) and 7 (11 mg, 24 mmol) were dissolved in $CH_2Cl_2$ (800 μl) and treated with $Cs_2CO_3$ (400 μg, 1.2 mmol) and a 0.04 M solution of CuI in acetonitrile (40 μl) for 12 h at RT. The reaction was then diluted into ethyl acetate (10 mL) and washed with water (3×10 mL), brine (10 mL), and dried over sodium sulfate. The combined organic layers were concentrated under reduced pressure and used without further purification. The crude product was dissolved in $CH_2Cl_2$ (2 mL) and treated with triisopropylsilane (20 μL, mmol) and trifluoroacetic acid (2 mL) for 1 h at RT. The reaction was diluted into toluene (5 mL) and concentrated under reduced pressure. The solid was then dissolved in water (5 mL) and washed with $CH_2Cl_2$ (3×5 mL). The aqueous phase was reduced to a solid under reduced pressure and purified on a C-18 reverse phase HPLC column using a gradient of 5-20% acetonitrile (0.1% TFA) in water (0.1% TFA) over 20 minutes (3 mL/min) The compound eluted as a TFA salt at 16.6 min (13 mg, 11 μmol, 88% yield).

Compound 2. 12 (39 mg, 19 μmol) and 8 (5.4 mg, 8.4 μmol) were dissolved in $CH_2Cl_2$ (1.0 mL) and treated with $Cs_2CO_3$ (600 mg, 1.9 mmol), and a 0.04 M solution of CuI in acetonitrile (40 μl) for 12 h at RT. The reaction was then diluted into ethyl acetate (10 mL) and washed with water (3×10 mL), brine (10 mL), and dried over sodium sulfate. The combined organic layers were concentrated under reduced pressure. The crude product was dissolved in $CH_2Cl_2$ (2 mL) and treated with triisopropylsilane (20 μL) and trifluoroacetic acid (2 mL) for 1 h at RT. The reaction was diluted into toluene (5 mL) and concentrated under reduced pressure. The solid was then dissolved in water (5 mL) and washed with $CH_2Cl_2$ (3×5 mL). The aqueous phase was then reduced to a solid under reduced pressure and purified on a C-18 reverse phase HPLC column using a gradient of 5-20% acetonitrile (0.1% TFA) in water (0.1% TFA) over 20 minutes (3 mL/min). The compound eluted at 18.7 min as a TFA salt (11 mg, 14 μmol, 76% yield).

Example 22

Synthesis of Monomeric and Dimeric Guanidinoparomomycin Conjugates

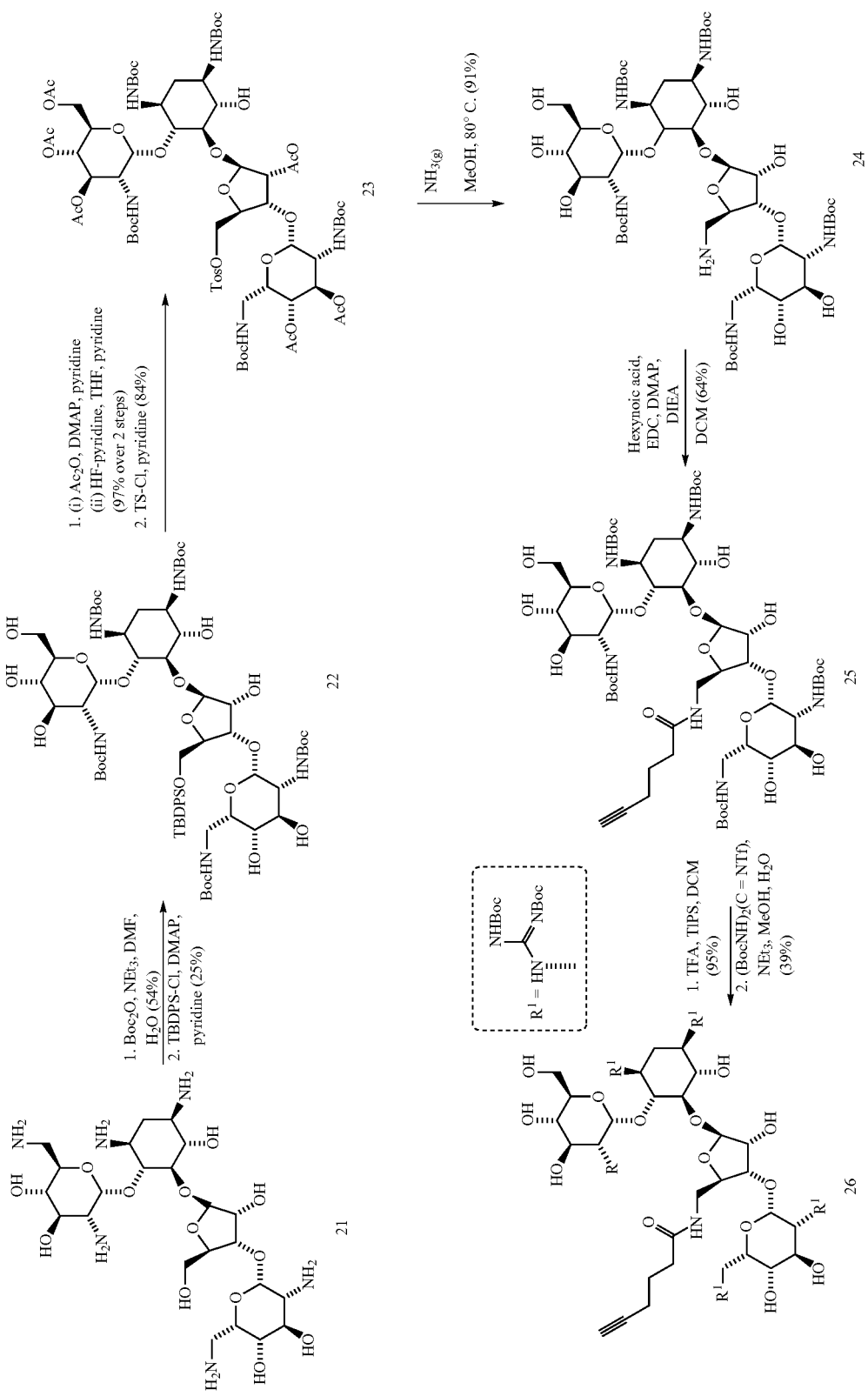

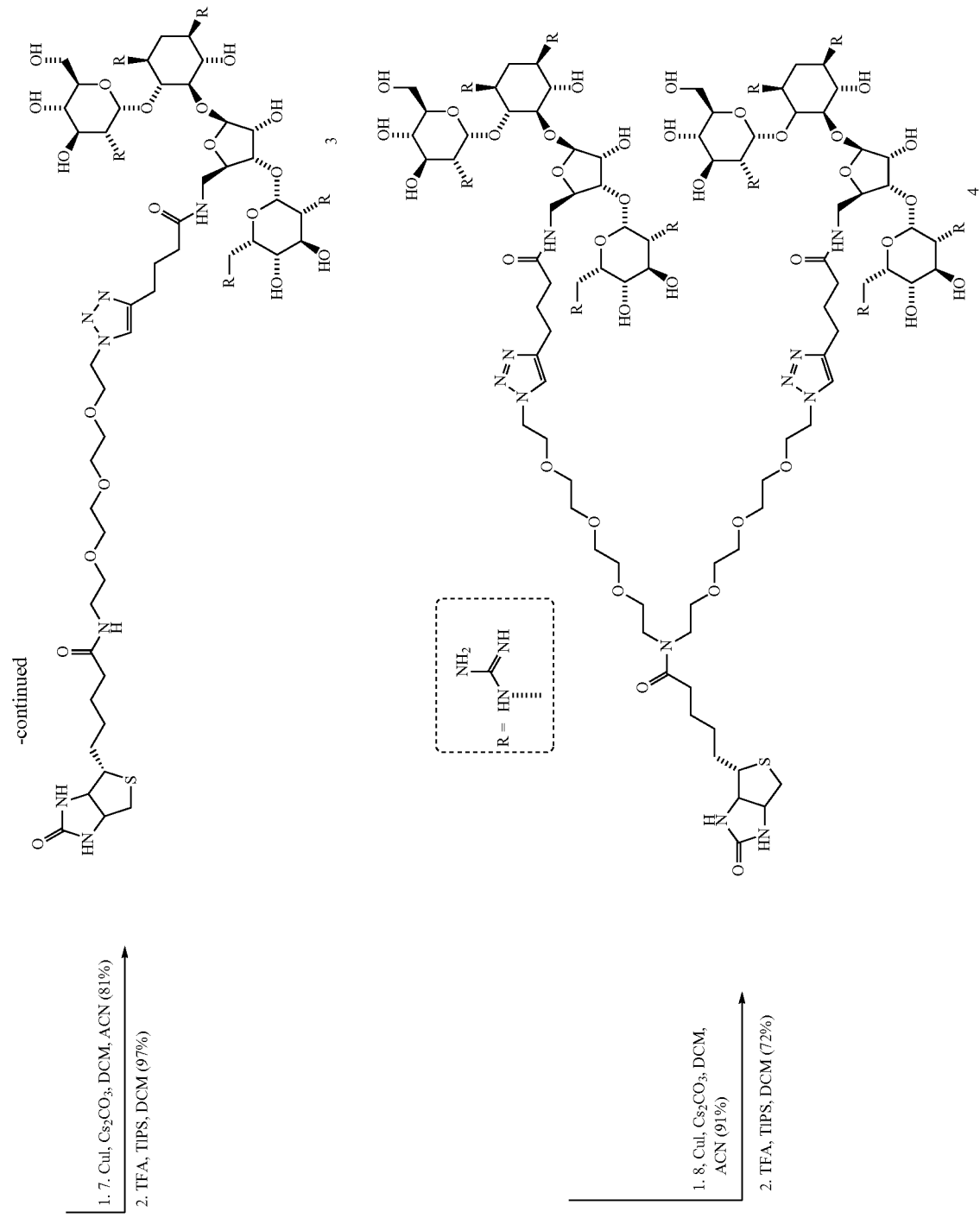

Precursors to compound 24 were prepared according to literature procedures. K. Michael, H. Wang, Y. Tor, *Bioorg. Med. Chem.* 1999, 7, 1361-1371; K. F. Blount, Y. Tor, *Chembiochem* 2006, 7, 1612-1621; and K. J. Bame, L. J. Zhang, G. David, J. D. Esko, *Biochemical J.* 1994, 303, 81-87.

Compound 26. 25 (65 mg, 0.054 mmol) was dissolved in $CH_2Cl_2$ (3 mL), and treated with triisopropylsilane (30 μL) and trifluoroacetic acid (3 mL) for 1 h at RT. The reaction was diluted into toluene (30 mL) and concentrated under reduced pressure. The solid was then dissolved in water (10 mL) and washed with $CH_2Cl_2$ (3×15 mL). The aqueous phase was then reduced to a solid under reduced pressure. The crude product was dissolved in methanol (500 μL) and treated with a solution of N,N'-di-tertbutoxycarbonyl-N"-triflylguanidine (650 mg, 1.66 mmol) and triethylamine (160 μL, 1.15 mmol) in $CHCl_3$ (2 mL) for 36 h at RT under argon. The reaction was then diluted into $CH_2Cl_2$ (15 mL), washed with water (3×10 mL), brine (10 mL), and dried over sodium sulfate. The combined organic layer were concentrated under reduced pressure and further purified by flash chromatography (2% methanol in $CH_2Cl_2$) to afford the product as an off-white solid (34 mg, 0.018 mmol, 39% yield).

Compound 3. 26 (16 mg, 8.7 μmol) and 7 (30 mg, 16 μmol) were dissolved in $CH_2Cl_2$ (600 μl) and treated with $Cs_2CO_3$ (300 mg, 1 μmol) and a 0.04 M solution of CuI in acetonitrile (40 μl) for 12 h at RT. The solvents were removed under reduced pressure and the residue was redissolved in $CH_2Cl_2$ (2 mL) and treated with triisopropylsilane (20 μL, mmol) and trifluoroacetic acid (2 mL) for 1 h at RT. The reaction was diluted into toluene and (5 mL) and concentrated under reduced pressure. The solid was then dissolved in water (5 mL) and washed with $CH_2Cl_2$ (3×5 mL). The aqueous phase was reduced to a solid under reduced pressure and purified on a C-18 reverse phase HPLC column using a gradient of 10-50% acetonitrile (0.1% TFA) in water (0.1% TFA) over 30 minutes (3 mL/min). The compound eluted at 10.1 min (5 mg, 4 μmol, 56%).

Compound 4. 26 (20 mg, 10 μmol) and 8 (3.0 mg, 4.0 μmol) were dissolved in $CH_2Cl_2$ (400 μL) and treated with $Cs_2CO_3$ (300 μg, 1 μmol), and a 0.04 M solution of CuI in acetonitrile (50 μl) for 12 h at RT. The solvents were removed under reduced pressure and the residue was redissolved in $CH_2Cl_2$ (1 mL) and treated with triisopropylsilane (10 μL) and trifluoroacetic acid (1 mL) for 1 h at RT. The reaction was diluted into toluene and (5 mL) and concentrated under reduced pressure. The solid was then dissolved in water (5 mL) and washed with $CH_2Cl_2$ (3×5 mL). The aqueous phase was then reduced to a solid under reduced pressure and purified on a C-18 reverse phase HPLC column using a gradient of 30-60% acetonitrile (0.1% TFA) in water (0.1% TFA) over 8 minutes (3 mL/min). The compound eluted at 4.5 min (17 mg, 6 μmol, 66% yield).

Example 23

Synthesis of Monomeric and Dimeric Guanidinotobramycin

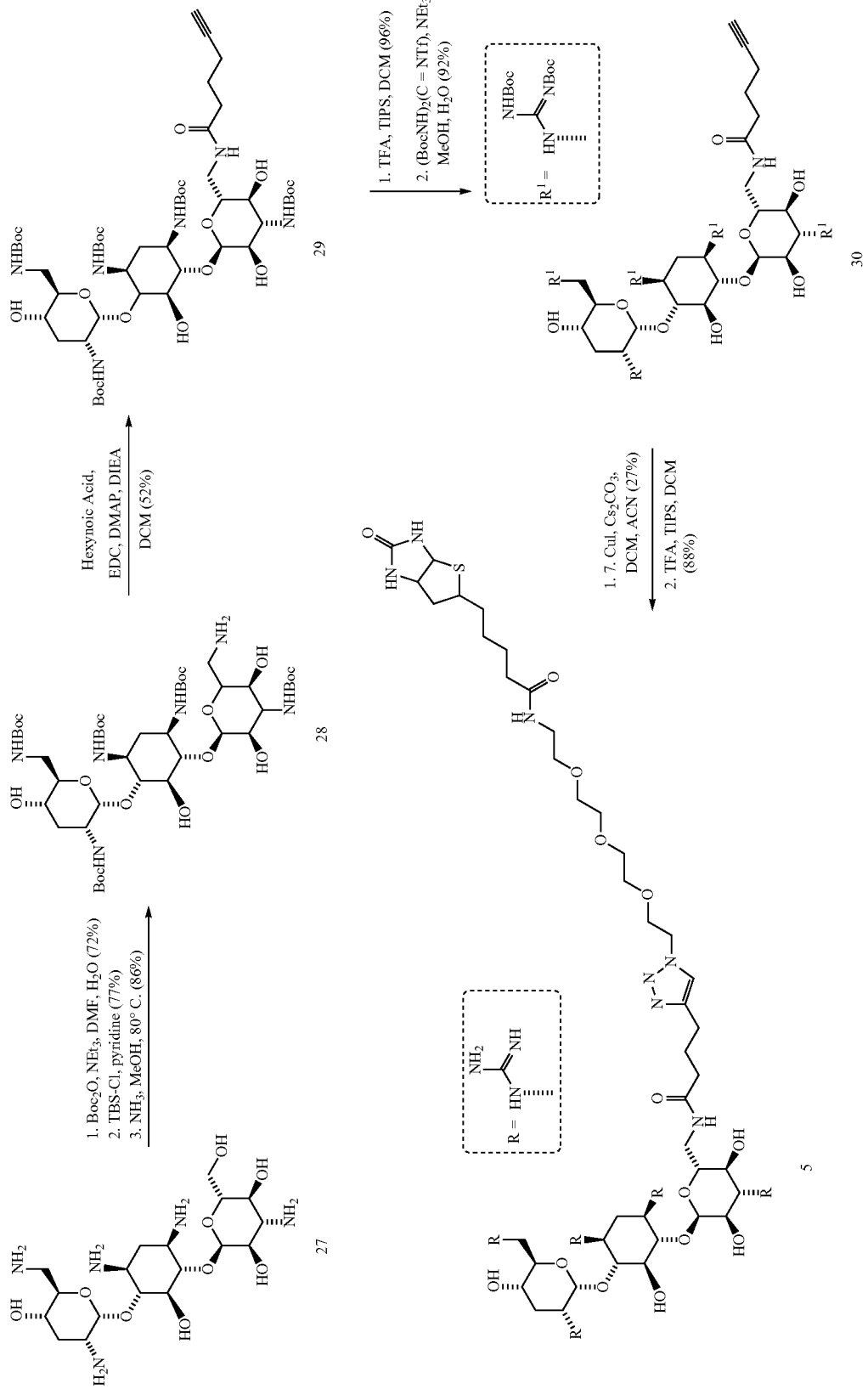

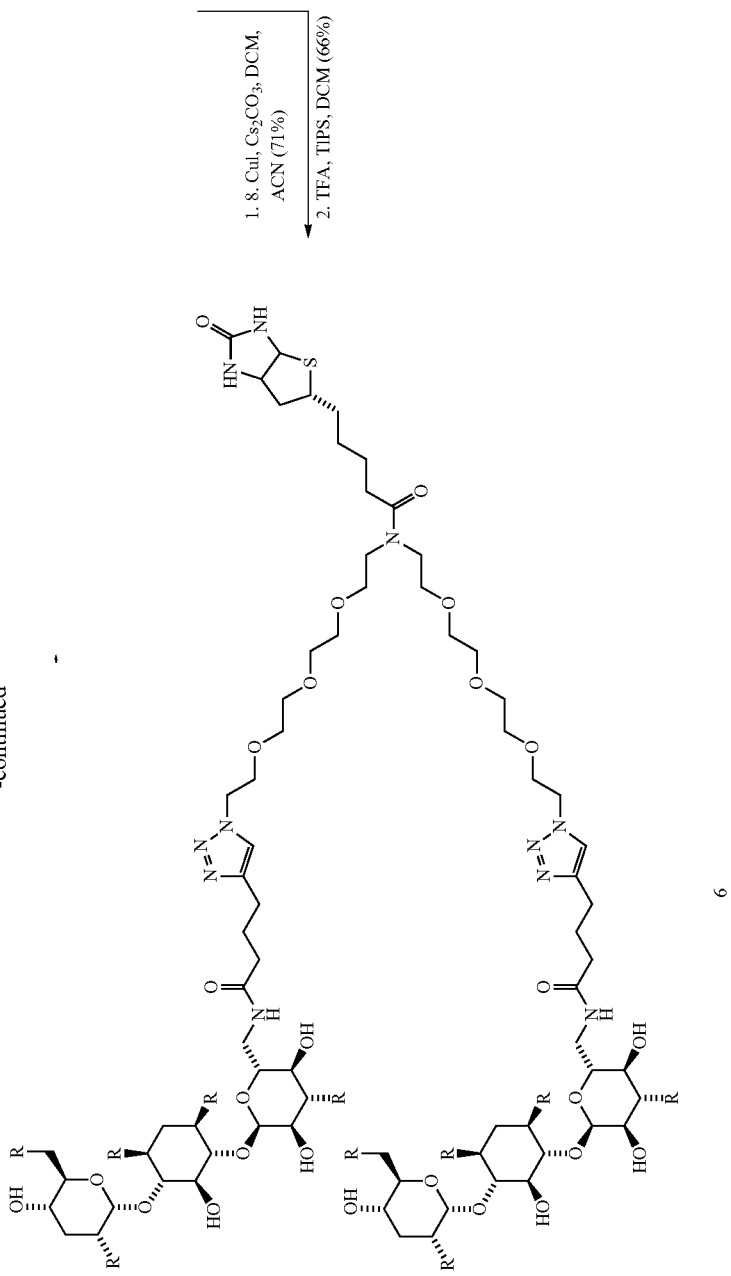

Precursors to compound 28 were prepared according to literature procedures. See K. Michael, H. Wang, Y. Tor, *Bioorg. Med. Chem.* 1999, 7, 1361-1371; K. F. Blount, Y. Tor, *Chembiochem* 2006, 7, 1612-1621; and K. J. Bame, L. J. Zhang, G. David, J. D. Esko, *Biochemical J.* 1994, 303, 81-87.

Compound 30. 29 (210 mg, 0.20 mmol) was dissolved in $CH_2Cl_2$ (5 mL), and treated with triisopropylsilane (50 μL) and trifluoroacetic acid (5 mL) for 1 h at RT. The reaction was diluted into toluene (30 mL) and concentrated under reduced pressure. The solid was then dissolved in water (10 mL) and washed with $CH_2Cl_2$ (3×15 mL). The aqueous phase was then reduced to a solid under reduced pressure. The crude product was dissolved in methanol (2 mL) and treated with a solution of N,N'-di-tertbutoxycarbonyl-N''-triflylguanidine (1.88 g, 4.81 mmol) and triethylamine (644 μL, 4.620 mmol) in $CHCl_3$ (8 mL) for 36 h at RT under argon. The reaction was then diluted into $CH_2Cl_2$ (15 mL), washed with water (3×10 mL), brine (10 mL), and dried over sodium sulfate. The combined organic layer were concentrated under reduced pressure and further purified by flash chromatography (2% methanol in $CH_2Cl_2$) to afford the product as an off-white solid (300 mg, 180 mmol, 92% yield).

Compound 5. 30 (28 mg, 16 μmol) and 7 (7 mg, 24 μmol) were dissolved in $CH_2Cl_2$ (600 μl) and treated with $Cs_2CO_3$ (300 mg, 1 μmol) and a 0.04 M solution of CuI in acetonitrile (40 μl) for 12 h at RT. The solvents were removed under reduced pressure and the crude product was dissolved in $CH_2Cl_2$ (4 mL) and treated with triisopropylsilane (40 μL, mmol) and trifluoroacetic acid (4 mL) for 1 h at RT. The reaction was diluted into toluene and (5 mL) and concentrated under reduced pressure. The solid was then dissolved in water (5 mL) and washed with $CH_2Cl_2$ (3×5 mL). The aqueous phase was reduced to a solid under reduced pressure and purified on a C-18 reverse phase HPLC column using a gradient of 20-40% acetonitrile (0.1% TFA) in water (0.1% TFA) over 15 minutes (3 mL/min). The compound eluted at 9.0 min (22 mg, 14 μmol, 88% yield).

Compound 6. 30 (30 mg, 17 μmol) and 8 (4.4 mg, 6.8 μmol) were dissolved in $CH_2Cl_2$ (400 μL) and treated with $Cs_2CO_3$ (1.7 mmol), and a 0.04 M solution of CuI (0.1 eq) in acetonitrile (85 μl) for 12 h at RT. The solvents were removed under reduced pressure and the crude product was dissolved in $CH_2Cl_2$ (2 mL) and treated with triisopropylsilane (10 μL, mmol) and trifluoroacetic acid (2 mL) for 1 h at RT. The reaction was diluted into toluene and (5 mL) and concentrated under reduced pressure. The solid was then dissolved in water (5 mL) and washed with $CH_2Cl_2$ (3×5 mL). The aqueous phase was then reduced to a solid under reduced pressure and purified on a C-18 reverse phase HPLC column using a gradient of 10-60% acetonitrile (0.1% TFA) in water (0.1% TFA) over 15 minutes (3 mL/min). The compound eluted at 8.7 min (6 mg, 7.5 μmol, 44% yield).

Example 24

Quantifying Cellular Uptake

The guanidinoglycoside derivatives described in Examples 21-23 were dissolved into HBSS and treated with fluorescently labeled streptavidin (ST-PE-Cy5) in a 10:1 molar ratio. After 15 minutes, the unbound biotinylated-guanidinoglycoside conjugates were removed using a desalting spin column (Amicon Ultra-4 Centrifugal Filter with a 10 KDa threshold from Millipore), leaving only the guanidinoglycoside-streptavidin conjugate in the column. The purified conjugates were diluted into media to form 10, 25, 50, 100, 150, and 200 nM solutions. The media used in these experiments was treated with 10% fetal bovine serum (FBS).

150,000 cells were counted using a hemocytometer for each of the cell lines examined (CHO mutants pgsA, pgsD, pgsE, and pgsF) and transferred to 24-well plates, and incubated in 300 μL of media (with a 1% solution of penicillin/streptomycin and 10% FBS) overnight at 37° C. The cells were then washed with PBS and treated with a 150 μL solution of the corresponding conjugate (in F-12 Media containing 10% FBS) and incubated for 2 hours. Following this, the cells were washed twice with PBS to remove any remaining extracellular conjugates. The cells were then detached with 50 μL trypsin/EDTA, diluted with 50 μL media and 200 μL FACS buffer, and analyzed using flow cytometry. Cellular uptake was quantified by the mean fluorescence intensity; the crude data was interpreted using FlowJo v8.8.6 wherein the median value was determined and later plotted and further analyzed using GraphPad Prism v5.0a.

Figure 17:
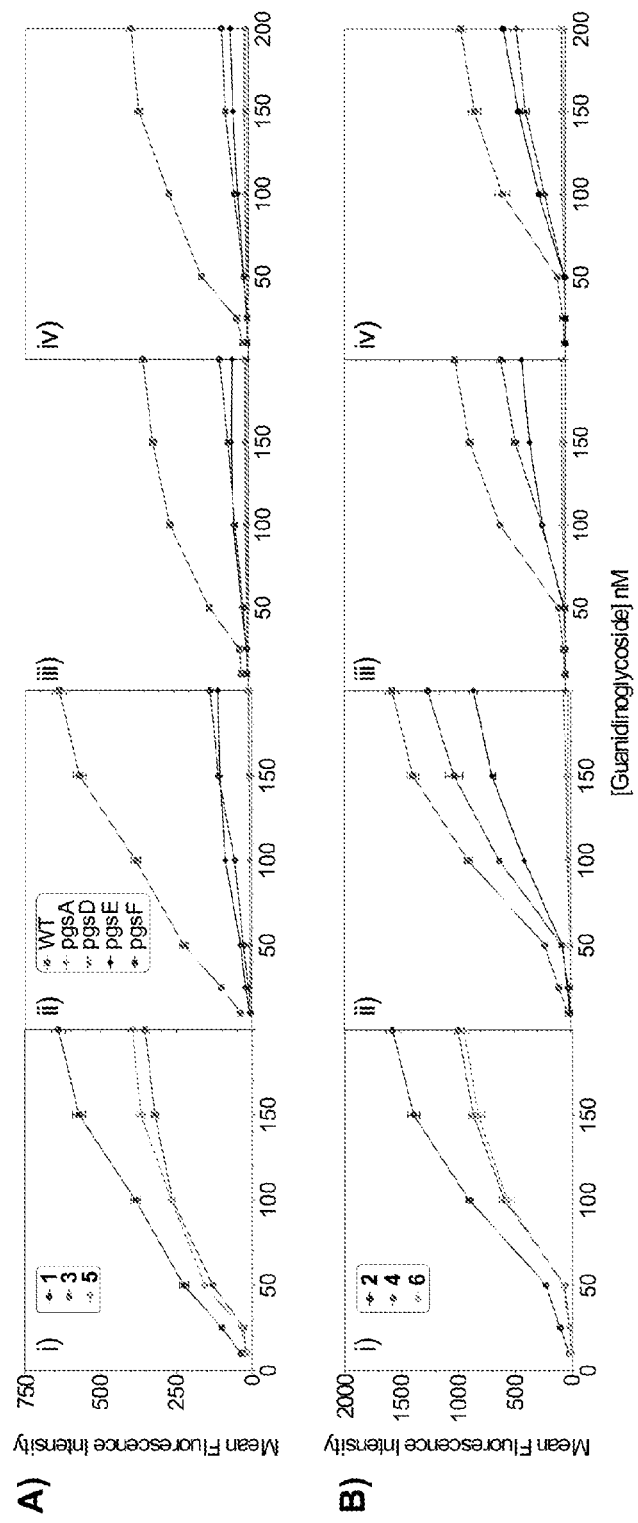
FIG. 17 compares the cellular uptake of (A) monomeric and (B) dimeric guanidinoglycoside constructs: i) CHO K1 (WT) cells, (ii) guanidinoneomycin, iii) guanidinoparomomycin, and iv) guanidinotobramycin against the cell lines tested.
Figure 18:
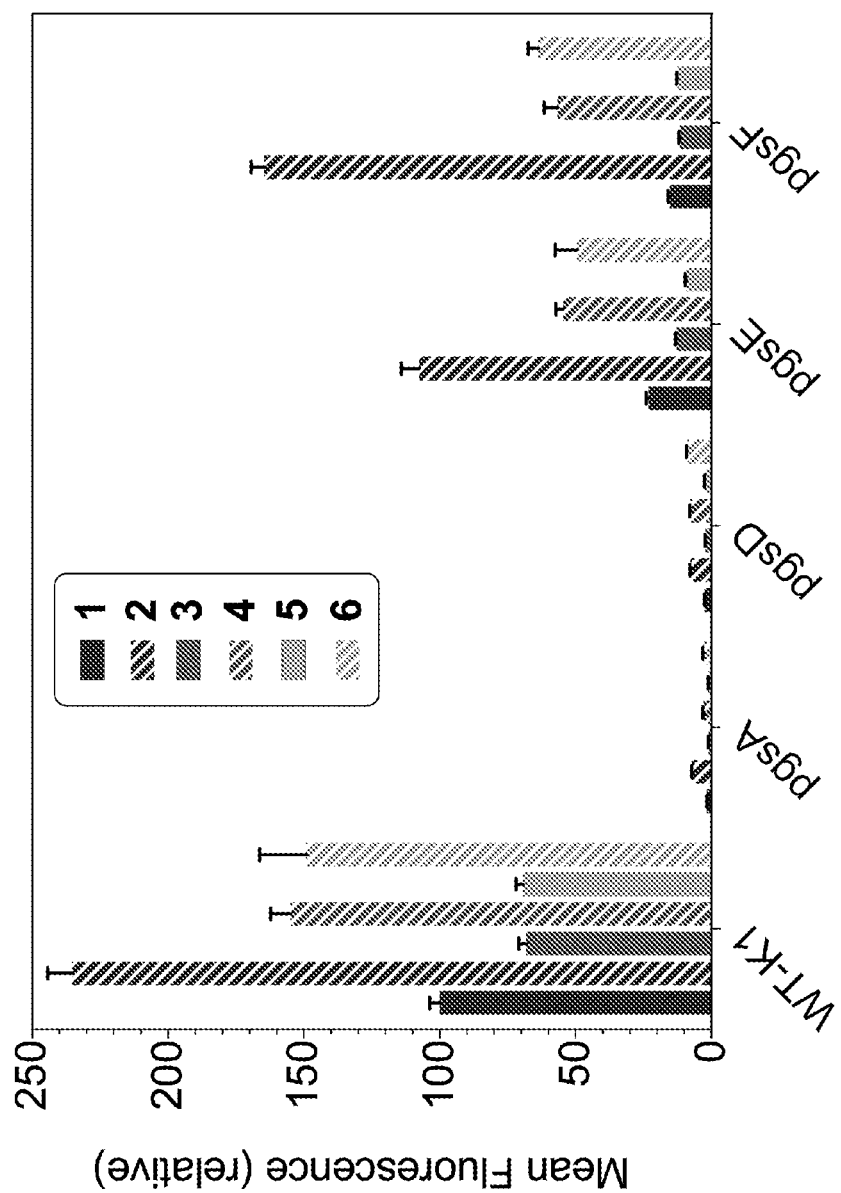
FIG. 18 shows normalized cellular uptake at 100 nM of the monomeric (solid) and dimeric (dashed) constructs with respect to the a) scaffold and b) various cell lines investigated.

FIG. 17 highlights the uptake data for the monomeric and dimeric constructs, while FIG. 18 summarizes the data at 100 nM carrier concentration.

Effect of number and distribution of guanidinium groups. Cellular internalization was found to be dependent on the number of guanidinium groups on the guanidinoglycoside scaffolds. For both the monomeric and dimeric constructs, the uptake of guanidinoneomycin (1/2) was 30% higher than that of guanidinoparomomycin (Compounds 3/4 of Example 22) and guanidinotobramycin (Compounds 5/6 of Example 23) (FIG. 17 Ai and Bi). This has been observed with other guanidinium containing transporters. See N. Sakai, T. Takeuchi, S. Futaki, S. Matile, Chembiochem 2005, 6, 114-122; and J. B. Rothbard, T. C. Jessop, R. S. Lewis, B. A. Murray, P. A. Wender *J. Am. Chem. Sci.* 2004, 126, 9506-9507. Additionally, the guanidinoparomomycin and guanidinotobramycin conjugates, for both the monomeric and dimeric constructs (compounds 3/5 and 4/6, respectively), demonstrated similar uptake behavior in all cell lines (FIG. 17). As both guanidinoglycoside scaffolds contain five guanidinium groups, this observation suggests that the 3-dimensional architecture of the guanidinium groups plays a limited role in cellular uptake. The inability of the cells, and more specifically cell surface glycans, to distinguish between the different arrangements suggests that the binding/recognition inherent to the uptake process could be quite plastic. Guanidinoglycosides, in contrast to linear guanidinium-rich carriers such as HIV TAT and poly-Arg, possess a high density of charged groups, and that the subtle differences in the architecture of these transporters might have been overshadowed by the inherent tetrameric nature of the streptavidin core.

Significance of glycan sulfation levels. Heparan sulfate deficient pgsA and pgsD mutant cells showed poor uptake, less than 5%, compared to uptake in wild type CHO cells (FIG. 17). This observation confirms the heparan sulfate-dependent nature of guanidinoglycoside cellular uptake observed before using different constructs, demonstrating that this is an inherent trait of the guanidinoglycoside scaffold and is not linker or construct dependent. For the monomeric constructs (FIG. 17A), uptake in the undersulfated pgsE and pgsF cells was reduced to less than 20% of that observed in the wild type cells. This behavior was not observed for the dimeric constructs (FIG. 17B), as high uptake levels, between 50-75% compared to the uptake seen in wild type cells, were observed in both pgsE and pgsF mutant cells. These trends were observed at all concentrations tested, and suggest that there is a significant relationship between glycan sulfation and either the level of guanidinylation or the carrier valency.

Dimeric constructs illicit cooperative response. Minimal internalization was observed at concentrations lower than 50 nM (particularly for the guanidinoparomomycin and guanidinotobramycin derivatives) suggesting a switch-like or cooperative mechanism (FIG. 17). This cooperative-like effect was accentuated in the dimeric constructs, consistent with the idea that the guanidinoglycosidic ligand induces clustering of heparan sulfate proteoglycans.

In wild type cells, all the dimeric constructs showed 2.5-fold enhanced uptake over the corresponding monomeric carriers, while a 5-fold increase was observed in the undersulfated cell lines pgsE and pgsF at 100 nM concentrations (FIG. 18). For the guanidinoneomycin constructs (Compounds 1 and 2 of Example 21), a 10-fold increase in uptake of the dimeric construct over monomeric was observed in pgsF cells at the same concentration (FIG. 18). This trend demonstrates that the dimeric constructs are increasingly able to overcome undersulfation and maintain high levels of cellular uptake. The dimeric constructs demonstrate a chelate-like effect enabling increased interactions between the carrier and cell surface glycans, thus facilitating effective uptake.

Example 25

Competition Experiments Using Model Oligomeric Glycans

To further assess the significance of glycan sulfation levels and support the observations described above in Example 24, the cellular uptake of the guanidinoneomycin constructs, compounds 1 and 2 (Example 21), was evaluated in the presence of competing model glycans derived from heparin. In this fashion, coloring of the results due to subtle variations between mutant cell lines, in addition to the specific glycosaminoglycan modification as described above, can be significantly reduced or eliminated.

50,000 WT CHO-K1 cells were counted using a hemocytometer, seeded onto 48-well plates, and incubated in 300 µL of media (with a 1% solution of penicillin/streptomycin and 10% FBS) overnight at 37° C. The cells were then washed with PBS and treated with a 75 µL solution (in media with 10% FBS) of the various glycans. Specifically, heparin, de 2-O sulfated heparin, de 6-O sulfated heparin, de O-sulfated heparin, N-desulfo-N-acetylated heparin, and heparin containing reduced uronic acids were tested.

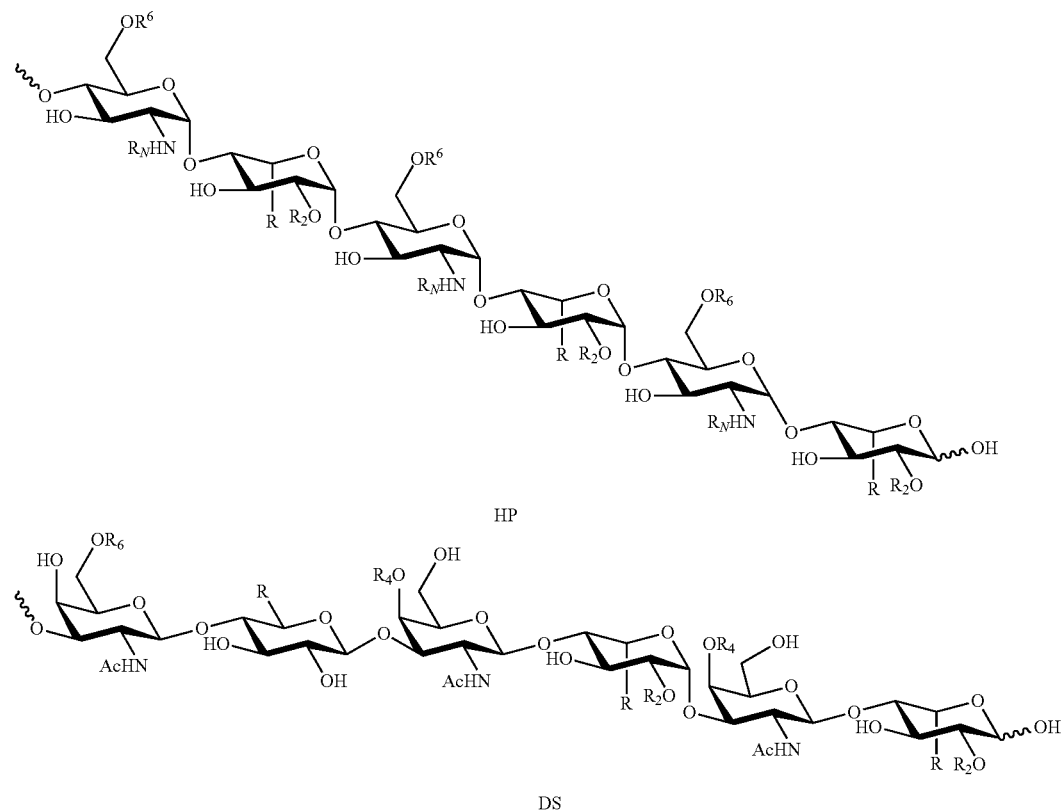

A) Heparin $R_2 = R_6 = R_N = SO_3^-$, $R = COO^-$
B) de 2-O $R_2 = H$, $R_6 = R_N = SO_3^-$, $R = COO^-$
C) de 6-O $R_2 = SO_3^-$, $R_6 = H$, $R_N = SO_3^-$, $R = COO^-$
D) de OS $R_2 = R_6 = H$, $R_N = SO_3^-$, $R = COO^-$
E) NAc $R_2 = SO_3^-$, $R_6 = H$, $R_N = Ac$, $R = COO^-$
F) CR $R_2 = R_6 = R_N = SO_3^-$, $R = OH$
G) DS $R_2 = R_4 = R_6 = SO_3^-$ $R = COO^-$ To each well, 75 uL of a 1.5 nM solution (in media with 10% FBS) of the guanidinoglycoside conjugates was added (note, the conjugates were prepared and purified in the same way as for the quantification study). The cells were then incubated for two hours, at which point they were washed twice with PBS and detached using 30 uL trypsin/EDTA. The lifted cells were diluted with 30 μL media and 200 μL of FACS buffer and analyzed by flow cytometry.

Figure 19:
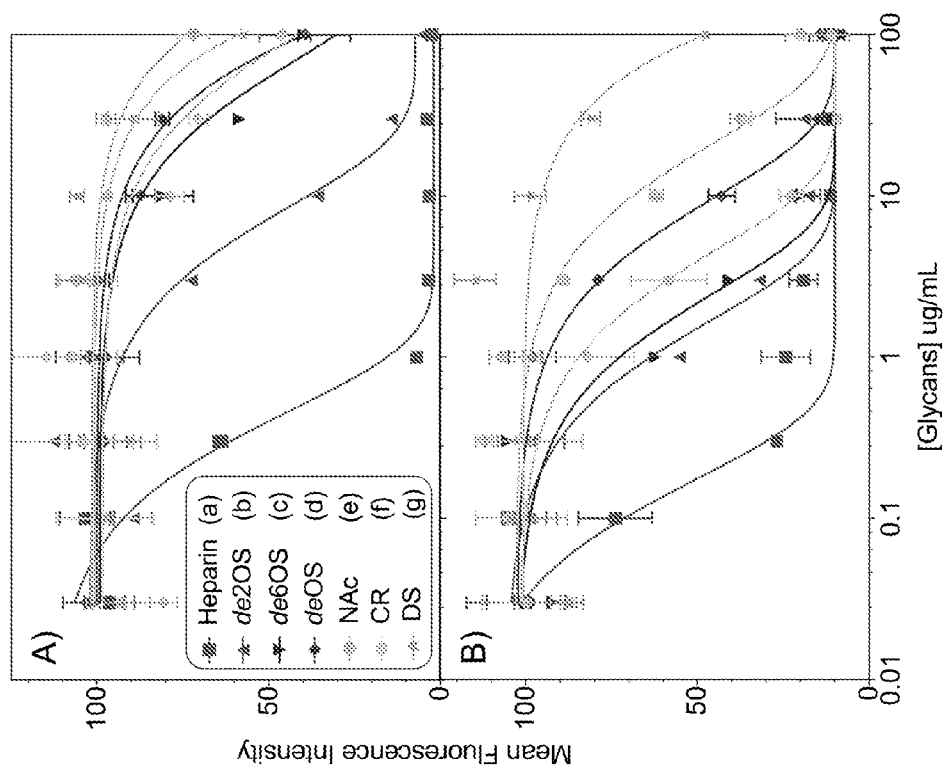
FIG. 19 shows normalized inhibition curves for A) monomeric guanidinoneomycin and B) dimeric guanidinoneomycin.

The mean fluorescence intensity was plotted against the concentration of the glycans utilized (FIG. 19), and $IC_{50}$ values were extracted (See Table).

| Glycan | 1 | 2 |
|---|---|---|
| Heparin (A) | 0.33 (±0.1) | 0.11 (±0.07) |
| de 2-O sulfate (B) | 6.3 (±3.5) | 0.94 (±0.8) |
| de 6-O sulfate (C) | >100 | 1.7 (±0.8) |
| de O sulfate (D) | >100 | 6.5 (±2) |
| N-Acetyl (E) | >100 | 11 (±10.5) |
| Carboxy reduced (F) | >100 | 3.2 (±3) |
| Dermatan sulfate, DS (G) | >100 | >100 |

Inhibition of guanidinoglycoside uptake with native heparin elicited the most pronounced inhibitory response (FIG. 19), highlighting a 3-fold increase of sensitivity of the dimeric over the monomeric construct. This appears intuitive as heparin contains the highest sulfation levels of the competing glycans, and mirrors the modest cooperative affect observed for cellular uptake in wild type cells. For monomeric guanidinoneomycin 1, only heparin and de 2-O sulfate heparin showed inhibition at the tested concentrations. For dimeric guanidinoneomycin 2, inhibition was observed for all the heparin derivatives. Dermatan sulfate failed to inhibit cellular uptake of either construct. The inhibition response from undersulfated heparin glycans demonstrated a dramatic 10-fold difference in efficiency between constructs. These observations parallel the uptake data of Example 24, which showed that the dimeric scaffold increases the ability of the guanidinoglycoside to interact with undersulfated cell surface glycans.

The $IC_{50}$ values obtained from the competition study indicate that all charged functional groups of the glycosaminoglycans are important for binding/recognition toward guanidinoglycosides. However, as indicated by the high level of inhibition maintained for de 2-O sulfate heparin (FIG. 19), some positions and functional groups may be more vital than others. This is likely the result of the overall structure and presentation of these charged groups. Additionally, dermatan sulfate displayed no significant inhibition, further supporting that there is little to no interaction between this glycan and guanidinoglycosides. This corroborates and complements the lack of uptake observed in the pgsD mutant cells, which over express an analogous glycan.

Although the disclosure has been described with reference to the above examples, it will be understood that modifications and variations are encompassed within the spirit and scope of the disclosure. Accordingly, the disclosure is limited only by the following claims.

What is claimed is:

1. A conjugate comprising a dimeric guanidinoglycoside and an enzyme useful for treating a lysosomal storage disease, the dimeric guanidinoglycoside is covalently bound to the enzyme, wherein the covalent bond is direct or optionally through a linker; and wherein each guanidinoglycoside of the dimeric guanidinoglycoside independently comprises an aminoglycoside antibiotic in which all of the ammonium groups have been converted into guanidinium groups.

2. The conjugate of claim 1, wherein the linker comprises an N-hydroxysuccinimide moiety.

3. The conjugate of claim 1, wherein the enzyme is selected from the group consisting of: α-D-mannosidase; N-aspartyl-β-glucosaminidase; acid lipase; hexosaminidase A; α-galactosidase A; β-galactosidase; ceramidase; fucosidase; β-glucosidase; N-acetylglucosamine-1-phosphotransferase; galactocerebrosidase; arylsulfatase A; N-acetylglucosamine-1-phosphotransferase; α-L-iduronidase; iduronate sulfatase; heparan sulfamidase; N-acetylglucosaminidase; acetyl-CoA: α-glucosaminide acetyltransferase; N-acetylglucosamine 6-sulfatase; N-acetylgalactosamine-6-sulfate sulfatase; N-acetylgalactosamine-4-sulfatase; β-glucuronidase; hyaluronidase; sialidase; sulfatase; sphingomyelinase; acid α-glucosidase; β-mannosidase; cathepsin K; β-hexosaminidase A; β-hexosaminidase B; α-N-acetylgalactosaminidase; sialin; and hexosaminidase A.

4. The conjugate of claim 3, wherein the enzyme is β-glucosidase or α-iduronidase.

5. The conjugate of claim 1, wherein the lysosomal storage disease is selected from the group consisting of: Activator Deficiency; Alpha-mannosidosis; Aspartylglucosaminuria; Cholesteryl ester storage disease; Chronic Hexosaminidase A Deficiency; Cystinosis; Danon disease; Fabry disease; Farber disease; Fucosidosis; Galactosialidosis; Gaucher disease; GM1 gangliosidosis; I-Cell disease; Infantile Free Sialic Acid Storage Disease; Juvenile Hexosaminidase A deficiency; Krabbe disease; Metachromatic Leukodystrophy; Mucopolysaccharidoses disorders; Multiple sulfatase deficiency; Niemann-Pick disease; Neuronal Ceroid Lipofuscinoses; Pompe disease; Pycnodysostosis; Sandhoff disease; Schindler disease; Salla disease; Tay-Sachs; and Wolman disease.

6. The conjugate of claim 5, wherein the Mucopolysaccharidoses disorders are selected from the group consisting of: Pseudo-Hurler polydystrophy; Hurler Syndrome; Scheie syndrome; Hurler-Scheie syndrome; Hunter syndrome; Sanfilippo syndrome type A; Sanfilippo syndrome type B; Sanfilippo syndrome type C; Sanfilippo syndrome type D; Morquio type A; Morquio type B; Maroteaux-Lamy; Sly syndrome; and Natowicz syndrome Hyaluronidase deficiency.

7. The conjugate of claim 5, wherein the Neuronal Ceroid Lipofuscinoses are selected from the group consisting of: CLN6 disease; Batten-Spielmeyer -Vogt/Juvenile NCL/CLN3 disease; Finnish Variant/Late Infantile CLN5; Jansky-Bielschowsky disease/Late infantile CLN2/TPP1 Disease; Kufs/Adult-onset NCL/CLN4 disease; Northern Epilepsy/variant Late Infantile CLN8; Santavuori-Haltia/Infantile CLN1/PPT disease; and β-mannosidosis.

8. The conjugate of claim 1, wherein each guanidinoglycoside is independently selected from the group consisting of guanidino-amikacin, guanidino-gentamicin, guanidino-kanamycin, guanidino-neomycin, guanidino-netilmicin, guanidino -paromomycin, guanidino-streptomycin, and guanidino-tobramycin.

9. The conjugate of claim 1, wherein the conjugate has the following structure:

wherein:
GG is a guanidinoglycoside comprising an aminoglycoside antibiotic in which all of the ammonium groups have been converted into guanidinium groups, where each GG is independently bound to the linker; and enzyme is an enzyme useful for the treatment of a lysosomal storage disease.

10. The conjugate of claim 9, wherein the enzyme is β-glucuronidase.

11. The conjugate of claim 9, wherein the dimeric guanidinoglycoside comprises guanidinylated neomycin.

12. A method for treating a lysosomal storage disease in a mammal, the method comprising administering to the mammal a therapeutically effective amount of a conjugate comprising a dimeric guanidinoglycoside and an enzyme useful for treating a lysosomal storage disease, wherein each guanidinoglycoside of the dimeric guanidinoglycoside independently comprises an aminoglycoside antibiotic in which all of the ammonium groups have been converted into guanidinium groups.

13. A method for increasing the cellular uptake of an enzyme useful for treating a lysosomal storage disease, the method comprising:
a) coupling the enzyme to a dimeric guanidinoglycoside to form a conjugate, wherein each guanidinoglycoside of the dimeric guanidinoglycoside independently comprises an aminoglycoside antibiotic in which all of the ammonium groups have been converted into guanidinium groups; and
b) delivering the conjugate to a cell.

14. A method for increasing the lysosomal uptake of an enzyme useful for treating a lysosomal storage disease, the method comprising:
a) coupling the enzyme to a dimeric guanidinoglycoside to form a conjugate, wherein each guanidinoglycoside of the dimeric guanidinoglycoside independently comprises an aminoglycoside antibiotic.in which all of the ammonium groups have been converted into guanidinium groups; and
b) delivering the conjugate to a lysosome.

15. The conjugate of claim 1, wherein the conjugate delivers the enzyme to a lysosome within a cell.

16. The conjugate of claim 1, wherein the conjugate localizes within a lysosome within a cell.

17. The conjugate of claim 1, wherein the uptake of the conjugate into the lysosome is greater than the uptake of the unconjugated enzyme.

18. The conjugate of claim 9, wherein the linker comprises an N-hydroxysuccinimide moiety.

19. The conjugate of claim 9, wherein the linker is covalently bound to the enzyme through a amide bond.

20. The conjugate of claim 1, wherein each guanidinoglycoside of the dimeric glycoside is the same.

21. The conjugate of claim 1, wherein each guanidinoglycoside is independently selected from the group consisting of guanidino-neomycin, guanidino -paromomycin, and guanidino-tobramycin.

22. The conjugate of claim 1, wherein each guanidinoglycoside is guanidino-neomycin.

* * * * *